US012644100B2

(12) United States Patent
Claussnitzer et al.

(10) Patent No.: US 12,644,100 B2
(45) Date of Patent: Jun. 2, 2026

(54) METHODS FOR TREATING METABOLIC DISORDERS BY TARGETING ADCY5

(71) Applicants: THE BROAD INSTITUTE, INC., Cambridge, MA (US); BETH ISRAEL DEACONESS MEDICAL CENTER, Boston, MA (US); HEBREW SENIORLIFE, INC., Boston, MA (US)

(72) Inventors: Melina Claussnitzer, Boston, MA (US); Nasa Sinnott-Armstrong, Cambridge, MA (US); Isabel Sousa, Cambridge, MA (US); Samantha Laber, Cambridge, MA (US); Douglas Kiel, Boston, MA (US); Eric S. Lander, Cambridge, MA (US)

(73) Assignees: THE BROAD INSTITUTE, INC., Cambridge, MA (US); BETH ISRAEL DEACONESS MEDICAL CENTER, Boston, MA (US); HEBREW SENIORLIFE, INC., Boston, MA (US)

( * ) Notice: Subject to any disclaimer, the term of this patent is extended or adjusted under 35 U.S.C. 154(b) by 1073 days.

(21) Appl. No.: 17/615,540

(22) PCT Filed: May 29, 2020

(86) PCT No.: PCT/US2020/035443
§ 371 (c)(1),
(2) Date: Nov. 30, 2021

(87) PCT Pub. No.: WO2020/243661
PCT Pub. Date: Dec. 3, 2020

(65) Prior Publication Data
US 2022/0243178 A1 Aug. 4, 2022

Related U.S. Application Data

(60) Provisional application No. 62/855,780, filed on May 31, 2019.

(51) Int. Cl.
| | |
|---|---|
| *C12N 5/077* | (2010.01) |
| *A61K 35/32* | (2015.01) |
| *A61K 35/35* | (2015.01) |
| *A61P 3/00* | (2006.01) |
| *A61P 19/00* | (2006.01) |
| *C12N 9/22* | (2006.01) |
| *C12N 15/11* | (2006.01) |
| *C12Q 1/6851* | (2018.01) |
| *C12Q 1/6883* | (2018.01) |

(52) U.S. Cl.
CPC ............ *C12N 5/0653* (2013.01); *A61K 35/32* (2013.01); *A61K 35/35* (2013.01); *A61P 3/00* (2018.01); *A61P 19/00* (2018.01); *C12N 5/0654* (2013.01); *C12N 9/22* (2013.01); *C12N 15/11* (2013.01); *C12Q 1/6883* (2013.01); *C12N 2310/20* (2017.05); *C12N*

2800/80 (2013.01); *C12Q 1/6851* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | | |
|---|---|---|---|---|
| 7,713,695 B2 * | 5/2010 | Liew | .................... | C12Q 1/6883 |
| | | | | 536/23.5 |
| 8,796,182 B2 * | 8/2014 | Steinthorsdottir | ... | C12Q 1/6883 |
| | | | | 506/7 |
| 9,101,645 B2 * | 8/2015 | Watts | ...................... | A61P 25/24 |

FOREIGN PATENT DOCUMENTS

| | | |
|---|---|---|
| WO | 2010039536 A2 | 4/2010 |
| WO | 2019005884 A1 | 1/2019 |
| WO | 2019005886 A1 | 1/2019 |
| WO | 2019060746 A1 | 3/2019 |
| WO | 2019071048 A1 | 4/2019 |
| WO | 2019084063 A1 | 5/2019 |
| WO | 2020028555 A2 | 2/2020 |

OTHER PUBLICATIONS

"Abstracts of the 49th Annual Meeting of the EASD", Diabetologia, vol. 56, No. SI, 332,, Sep. 1, 2013, pp. 1-566.

(Continued)

*Primary Examiner* — Blaine Lankford
(74) *Attorney, Agent, or Firm* — Greenberg Traurig, LLP; Melissa Hunter-Ensor; Leslie Serunian

(57) ABSTRACT

Provided herein is a method for controlling a rate of fatty acid oxidation in mesenchymal cells, comprising modulating the expression or activity of ADCY5. The rate of fatty acid oxidation may be decreased by reducing the expression or activity of ADCY5. The rate of fatty acid oxidation may be increased by increasing the expression or activity of ADCY5. In some embodiments, the mesenchymal cell may be a mesenchymal stem cell, an adipocyte, an osteoblast, a chondrocyte, or a myocyte. In some embodiments, controlling the rate of fatty acid oxidation in mesenchymal stem cells comprises inhibiting fatty acid oxidation. In some embodiments, inhibiting fatty acid oxidation prevents development of Type 2 Diabetes (T2D). In some embodiments, controlling the rate of fatty acid oxidation in mesenchymal stem cells may comprise increasing the rate of fatty acid oxidation. Increasing the rate of fatty acid oxidation may promote bone formation.

31 Claims, 19 Drawing Sheets
Specification includes a Sequence Listing.

(56)  References Cited

OTHER PUBLICATIONS

"Abstracts of the EASD, Vienna 2009", Diabetologia ; Clinical and Experimental Diabetes and Metabolism, Springer, Berlin, DE, vol. 52, No. 1, 75, Aug. 14, 2009, pp. 1-550.

"International Search Report and Written Opinion for PCT/US2020/035443", issued by the European Patent Office, as International Searching Authority, Aug. 31, 2020.

Abudayyeh, et al., "A Cytosine Deaminase for Programmable Single-base RNA Editing", Science, vol. 365, Issue 6451, Jul. 26, 2019, 8 pages.

Anzalone, et al., "Search-and-replace Genome Editing Without Double-Strand Breaks or Donor DNA", Nature, vol. 576, No. 7785, Dec. 5, 2019, 149-157.

Balasubramanian, et al., "A Novel De Novo 20Q13.32-Q13.33 Deletion In A 2-year-old Child With Poor Growth, Feeding Difficulties and Low Bone Mass", Journal of Human Genetics, vol. 60, Mar. 12, 2015, 313-317.

Binz, et al., "Engineering Novel Binding Proteins from Nonimmunoglobulin Domains", Nature Biotechnology, vol. 23, No. 10, Oct. 6, 2005, 1257-1268.

Blanchette, et al., "Aligning Multiple Genomic Sequences with the Threaded Blockset Aligner", Genome Research, vol. 14, Feb. 3, 2004, 708-715.

Buenrostro, et al., "ATAC-seq: A Method for Assaying Chromatin Accessibility Genome-Wide", Current Protocols in Molecular Biology, vol. 109, Jan. 2015, 10 pages.

Bulik-Sullivan, et al., "An Atlas of Genetic Correlations Across Human Diseases and Traits", Nature Genetics, vol. 47, No. 11, Nov. 2015, 22 pages.

Chen, et al., "A Powerful Variant-Set Association Test Based on Chi-Square Distribution", Genetics, vol. 207, No. 3, Nov. 2017, 903-910.

Chen, et al., "Identifying Pleiotropic Effects: A Two-Stage Approach Using Genome-Wide Association Meta-Analysis Data", doi: https://doi.org/10.1101/184895 Retrieved as on Apr. 14, 2020, Sep. 5, 2017, 36 pages.

Chu, et al., "Efficient Generation of Rosa26 Knock-in Mice using Crispr/cas9 in C57bl/6 Zygotes", BMC Biotechnology, vol. 16, No. 4, Jan. 16, 2016, 15 pages.

Claussnitzer, et al., "Leveraging Cross-Species Transcription Factor Binding Site Patterns: From Diabetes Risk Loci to Disease Mechanisms", Cell, vol. 156, Issues 1-2,, Jan. 16, 2014, 343-358.

Cowper-Sal Lari, et al., "Breast Cancer Risk-associated SNPs Modulate The Affinity Of Chromatin for Foxa 1 and Alter Gene Expression", Nature Genetics, vol. 44, No. 11, Nov. 2012, 23 pages.

Dankel, et al., "Switch from Stress Response to Homeobox Transcription Factors in Adipose Tissue after Profound Fat Loss", PLoS One, vol. 5, No. 6, Jun. 2010, 12 pages.

De Kok, et al., "Normalization of Gene Expression Measurements in Tumor Tissues: Comparison of 13 Endogenous Control Genes", Laboratory Investigation, vol. 85, 2005, 154-159.

Defer, et al., "Tissue Specificity and Physiological Relevance of Various Isoforms of Adenylyl Cyclase", The American Journal of Physiology, vol. 279, No. 3, Sep. 10, 2020, F400-F416.

Dixon, et al., "Chromatin Architecture Reorganization During Stem Cell Differentiation", Nature, vol. 518, No. 7539, Feb. 19, 2015, 23 pages.

Dupuis, et al., "New Genetic Loci Implicated in Fasting Glucose Homeostasis and their Impact on type 2 Diabetes Risk", Nature Genetics, vol. 42, No. 2, Feb. 2010, 30 pages.

Edwards, et al., "Regulation of Gene Expression by SREBP and SCAP", Biochimica et Biophysica Acta (BBA)—Molecular and Cell Biology of Lipids, vol. 1529, No. 1-3, Dec. 15, 2000, 103-113.

Ernst, et al., "ChromHMM: Automating Chromatin-state Discovery and Characterization", Nature Methods, vol. 9, Feb. 28, 2012, 3 pages.

Estrada, et al., "Genome-wide Meta-analysis Identifies 56 Bone Mineral Density Loci and Reveals 14 Loci Associated with Risk of Fracture", Nature Genetics, vol. 44, No. 5, Nov. 1, 2012, 28 pages.

Falconi, et al., "LIF Inhibits Osteoblast Differentiation at Least in Part by Regulation of HAS2 and Its Product Hyaluronan", Journal of Bone and Mineral Research, vol. 22, No. 8,, Apr. 23, 2007, 13 pages.

Farley, et al., "Monofluorophosphate is Hydrolyzed by Alkaline Phosphatase And Mimics The Actions of NAF On Skeletal Tissues, In Vitro", Calcified Tissue International, vol. 40, No. 1, Jan. 1987, 35-42.

Finucane, et al., "Partitioning Heritability by Functional Annotation using Genome-wide Association Summary Statistics", Nature Genetics, vol. 47, No. 11, Nov. 2015, 28 pages.

Fischer-Posovszky, et al., "Human SGBS Cells—a Unique Tool for Studies of Human Fat Cell Biology", Obesity Facts, vol. 1, No. 4, Aug. 14, 2008, 184-189.

Frey, et al., "Wnt-lrp5 Signaling Regulates Fatty Acid Metabolism in the Osteoblast", Molecular and Cellular Biology, vol. 35, No. 11, Jun. 2015, 1979-1991.

Fuchsberger, et al., "The Genetic Architecture of Type 2 Diabetes", Nature, vol. 536, Aug. 4, 2016, 29 pages.

Gebauer, et al., "Engineered Protein Scaffolds as next-Generation Antibody Therapeutics", Current Opinion in Chemical Biology, vol. 13, No. 3, Jun. 2009, 245-255.

Gill, et al., "Biopharmaceutical Drug Discovery Using Novel Protein Scaffolds", Current Opinion in Biotechnology, vol. 17, No. 6, Dec. 2006, 653-658.

Girousse, et al., "Partial Inhibition of Adipose Tissue Lipolysis Improves Glucose Metabolism and Insulin Sensitivity Without Alteration of Fat Mass", PLOS Biology, vol. 11, Issue 2, e1001485, Feb. 2013, pp. 1-19.

Guilherme, et al., "Adipocyte Dysfunctions Linking Obesity to Insulin Resistance and Type 2 Diabetes", Nature Reviews Molecular Cell Biology, vol. 9, No. 5, May 2008, 25 pages.

Guntur, et al., "Osteoblast Like Mc3T3-e1 Cells Prefer Glycolysis for ATP Production but Adipocyte Like 3T3-11 Cells Prefer Oxidative Phosphorylation", Journal of Bone and Mineral Research, vol. 33, No. 6, Jun. 2018, 24 pages.

Hodson, et al., "ADCY5 Couples Glucose To Insulin Secretion In Human Islets", Diabetes, vol. 63, No. 9, Sep. 2014, 3009-3021.

Hsu, et al., "An epigenetic switch confers pleiotrpoic risk for bone mineral density and hyperglycaemia", 2017 Annual Meeting of the American Society for Bone and Mineral Research, Sep. 8, 2017.

Imakaev, et al., "Iterative Correction Of Hi-C Data Reveals Hallmarks Of Chromosome Organization", Nature Methods, vol. 9, No. 10, Oct. 2012, 999-1003.

Kelley, et al., "Basset: Learning The Regulatory Code of The Accessible Genome with Deep Convolutional Neural Networks", Genome Research, vol. 26, Apr. 26, 2016, 990-999.

Kim, et al., "Highly Efficient Rna-guided Genome Editing in Human Cells via Delivery of Purified Cas9 Ribonucleoproteins", Genome Research, vol. 24, No. 6, Jun. 24, 2014, 1012-1019.

Koide, et al., "Monobodies: Antibody Mimics Based on the Scaffold of the Fibronectin Type III Domain", Methods in Molecular Biology, vol. 352, 2007, 95-109.

Kolmar, "Alternative Binding Proteins: Biological Activity And Therapeutic Potential Of Cystine-knot Miniproteins", The FEBS Journal, vol. 275, No. 11, Jun. 2008, 2684-2690.

Korhonen, et al., "MOODS: Fast Search for Position Weight Matrix Matches In DNA Sequences", Bioinformatics, vol. 25, Issue 23, Dec. 1, 2009, 3181-3182.

Lee, et al., "Simultaneous Targeting of Linked Loci In Mouse Embryos Using Base Editing", Scientific Reports, vol. 9, No. 1662, 2019, 8 pages.

Lee, et al., "Targeting Fidelity of Adenine and Cytosine Base Editors in Mouse Embryos", Nature Communications, vol. 9, No. 4804, 2018, 6 pages.

Leslie, et al., "Type 2 Diabetes And Bone", Journal of Bone and Mineral Research, vol. 27, No. 11, Nov. 2012, 2231-2237.

Mabbott, et al., "An Expression Atlas of Human Primary Cells: Inference of Gene Function from Coexpression Networks", BMC Genomics, vol. 14, No. 632,, 2013, 13 pages.

Macarthur, et al., "The New Nhgri-ebi Catalog of Published Genome-wide Association Studies (Gwas Catalog)", Nucleic Acids Research, vol. 45, Nov. 28, 2016, D896-D901.

(56) References Cited

OTHER PUBLICATIONS

Manning, et al., "A Genome-Wide Approach Accounting for Body Mass Index Identifies Genetic Variants Influencing Fasting Glycemic Traits and Insulin Resistance", Nature Genetics, vol. 44, No. 6, 2012, 26 pages.

Maurano, et al., "Large-scale Identification of Sequence Variants Influencing Human Transcription Factor Occupancy in Vivo", Nature Genetics, vol. 47, No. 12, Dec. 2015, 29 pages.

Mookerjee, et al., "Measurement and Analysis of Extracellular Acid Production to Determine Glycolytic Rate", Journal of Visualized Experiments, vol. 106. No. e53464, Dec. 2015, 9 pages.

Morris, et al., "An Atlas of Human and Murine Genetic Influences on Osteoporosis", Retrieved as on Sep. 14, 2020( https://doi.org/10.1101/338863), Jul. 27, 2018, 42 pages.

Muerdter, et al., "Resolving Systematic Errors in Widely used Enhancer Activity Assays in Human Cells", Nature Methods, vol. 15, No. 2, Feb. 2018, 28 pages.

Nixon, et al., "Engineered Protein Inhibitors of Proteases", Current Opinion in Drug Discovery and Development, vol. 9, No. 2, Apr. 2006 , 261-268.

Nygren, "Alternative Binding Proteins: Affibody Binding Proteins Developed From A Small Three-helix Bundle Scaffold", The FEBS Journal, vol. 275, No. 11, Jun. 2008, 2668-2676.

Paix, et al., "High Efficiency, Homology-Directed Genome Editing in Caenorhabditis Elegans using CRISPR-Cas9 Ribonucleoprotein Complexes", Genetics, vol. 201, No. 1, Sep. 2015, 47-54.

Park, et al., "Multivariate Analysis of Anthropometric Traits Using Summary Statistics of Genome-Wide Association Studies from GIANT Consortium", PLOS One, DOI:(10.1371/journal.pone.0163912), Oct. 4, 2016, 17 pages.

Pickrell, et al., "Detection and Interpretation of Shared Genetic Influences on 42 Human Traits", Nature Genetics, vol. 48, No. 7, Jul. 2016, 21 pages.

Rees, et al., "Base Editing: Precision Chemistry on The Genome and Transcriptome of Living Cells", Nature Reviews Genetics, vol. 19, No. 12, Dec. 2018, 770-788.

Ribarska, et al., "Native Chromatin Immunoprecipitation-Sequencing (ChIP-Seq) from Low Cell Numbers", Methods in Molecular Biology, vol. 1689, 2018, 157-166.

Richter, et al., "Phage-assisted Evolution of an Adenine Base Editor with Improved Cas Domain Compatibility and Activity", Nature Biotechnology, vol. 38, 2020, 18 pages.

Roman, et al., "A Type 2 Diabetes-Associated Functional Regulatory Variant in a Pancreatic Islet Enhancer at the ADCY5 Locus", Diabetes, vol. 66, No. 9, Sep. 2017, 2521-2530.

Saxena, et al., "Genetic Variation in GIPR Influences The Glucose and Insulin Responses to an Oral Glucose Challenge", Nature Genetics, vol. 42, No. 2, Feb. 2010, 16 pages.

Scharer, et al., "Plasma Cell Differentiation is Controlled by Multiple Cell Division-coupled Epigenetic Programs", Nature Communications, vol. 9, No. 1698, 2018, 14 pages.

Sebastian, et al., "Novel Role of FATP1 in Mitochondrial Fatty Acid Oxidation in Skeletal Muscle Cells", Journal of Lipid Research, vol. 50, No. 9, 2009, 1789-1799.

Shulman, "Ectopic Fat in Insulin Resistance, Dyslipidemia, and Cardiometabolic Disease", The New England Journal of Medicine, vol. 371, No. 12, Sep. 18, 2014, 1131-1141.

Silverman, et al., "Multivalent Avimer Proteins Evolved by Exon Shuffling of A Family of Human Receptor Domains", Nature Biotechnology, vol. 23, No. 12, Dec. 2005, 1556-1561.

Sinnott-Armstrong, et al., "American Society of Human Genetics 67th Annual Meeting", American Society of Human Genetics,, Oct. 17, 2017, p. 151.

Skerra, "Alternative Binding Proteins: Anticalins—Harnessing The Structural Plasticity of the Lipocalin Ligand Pocket to Engineer Novel Binding Activities", The FEBS Journal, vol. 275, No. 11, Jun. 2008, 2677-2683.

Skerra, "Alternative Non-Antibody Scaffolds for Molecular Recognition", Current Opinion in Biotechnology, vol. 18, Issue 4, Aug. 2007, 295-304.

Skerra, "Engineered Protein Scaffolds for Molecular Recognition", Journal of Molecular Recognition, vol. 13, No. 4, 2000, 167-187.

Song, et al., "Adenine Base Editing in an Adult Mouse Model of Tyrosinemia", Nature Biomedical Engineering, vol. 4, No. 1, Jan. 2020, 14 pages.

Stumpp, et al., "DARPins: A New Generation of Protein Therapeutics", Drug Discovery Today, vol. 13, No. 15-16, Aug. 2008, 695-701.

Thurner, et al., "Integration of Human Pancreatic Islet Genomic Data Refines Regulatory Mechanisms at Type 2 Diabetes Susceptibility Loci", eLife, vol. 7, No. 31977, 2018, 30 pages.

Thuronyi, et al., "Continuous Evolution of Base Editors with Expanded Target Compatibility and Improved Activity", Nature Biotechnology, vol. 37, No. 9, Sep. 2019, 30 pages.

Turley, et al., "Enteral Administration of Twice-Daily Dolutegravir and Rilpivirine as a Part of a Triple-Therapy Regimen in a Critically Ill Patient with HIV", Journal of the International Association of Providers of AIDS Care, vol. 16, No. 2, 2017, 117-119.

Turley, et al., "Multi-trait Analysis of Genome-wide Association Summary Statistics Using MTAG", Nature Genetics, vol. 50, No. 2, Feb. 2018, 33 pages.

Veum, et al., "The Nuclear Receptors Nur77, Nurr1 And Nor1 In Obesity and During Fat Loss", International Journal of Obesity, vol. 36, No. 9, Sep. 2012, 1195-1202.

Wang, et al., "One-Step Generation of Mice Carrying Mutations in Multiple Genes by CRISPR/Cas-Mediated Genome Engineering", Cell, vol. 153, No. 4, May 9, 2013, 13 pages.

Weirauch, et al., "Determination and Inference of Eukaryotic Transcription Factor Sequence Specificity", Cell, vol. 158, No. 6, Sep. 11, 2014, 26 pages.

Wende, et al., "PGC-1 Coactivates PDK4 Gene Expression via the Orphan Nuclear Receptor ERR: a Mechanism for Transcriptional Control of Muscle Glucose Metabolism", Molecular And Cellular Biology, vol. 25, No. 24, Dec. 2005, 10684-10694.

Xue, et al., "Clonal Analyses and Gene Profiling Identify Genetic Biomarkers of The Thermogenic Potential of Human Brown and White Preadipocytes", Nature Medicine, vol. 21, No. 7, Jul. 2015, 12 pages.

Zhou, et al., "The Human Epigenome Browser at Washington University", Nature Methods, vol. 8, No. 12, Jan. 23, 2015, 4 pages.

Zhu, et al., "Causal Associations between Risk Factors and Common Diseases Inferred from GWAS Summary Data", Nature Communications, vol. 9, No. 224, 2018, 12 pages.

* cited by examiner

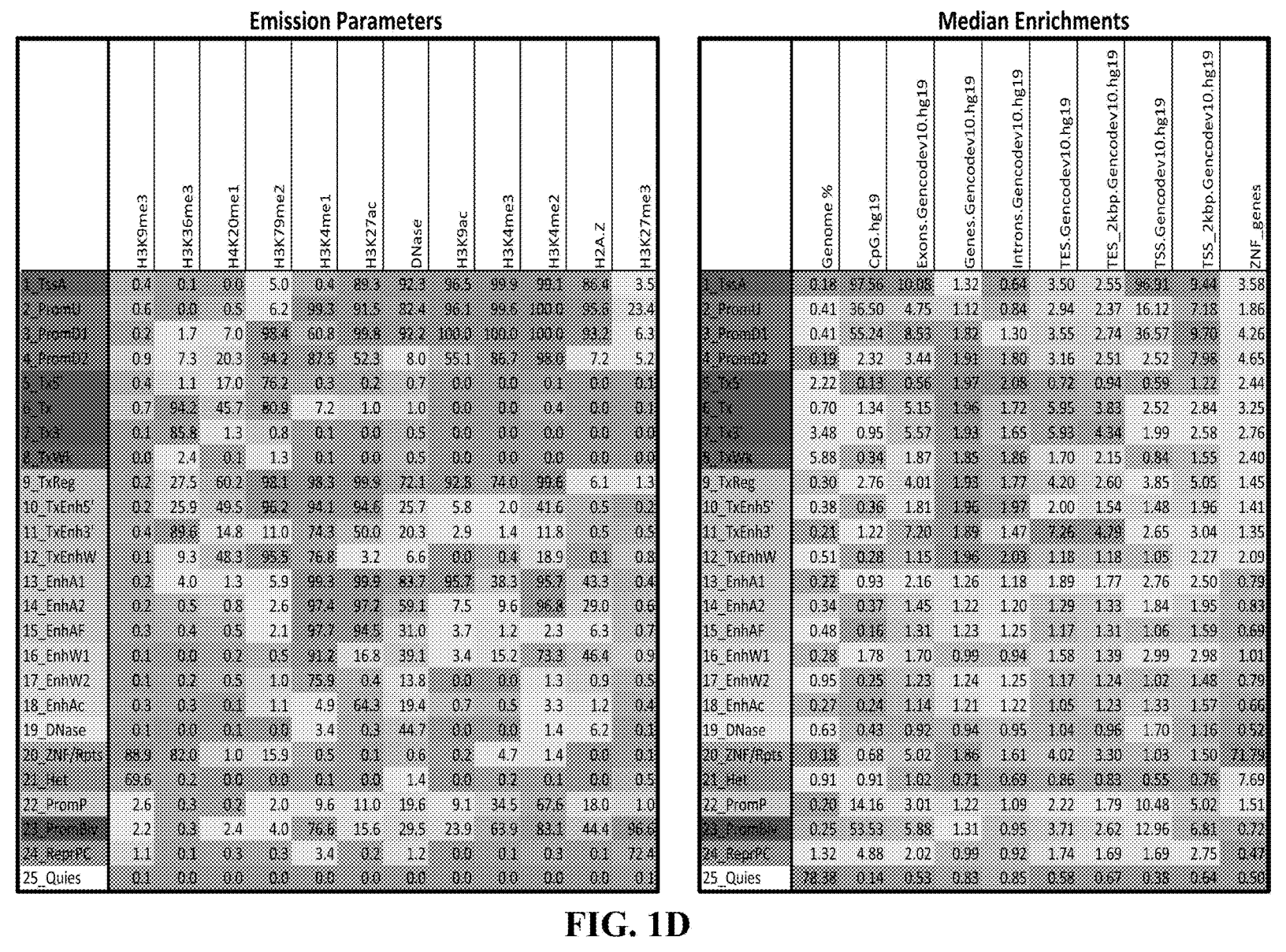

Median Enrichments

Column headers: ZNF_genes, TSS_2kbp.Gencodev10.hg19, TSS.Gencodev10.hg19, TES_2kbp.Gencodev10.hg19, TES.Gencodev10.hg19, Introns.Gencodev10.hg19, Genes.Gencodev10.hg19, Exons.Gencodev10.hg19, CpG.hg19, Genome %

Emission Parameters

Column headers: H3K27me3, H2A.Z, H3K4me2, H3K4me3, H3K9ac, DNase, H3K27ac, H3K4me1, H3K79me2, H4K20me1, H3K36me3, H3K9me3

Row labels (both panels): 1_TssA, 2_PromU, 3_PromD1, 4_PromD2, 5_Tx, 6_TxWk, 7_TxEnh, 8_TxEnhW, 9_TxReg, 10_TxEnhS, 11_TxEnh3, 12_TxEnhW, 13_EnhA1, 14_EnhA2, 15_EnhAF, 16_EnhW1, 17_EnhW2, 18_EnhAc, 19_DNase, 20_ZNF/Rpts, 21_Het, 22_PromP, 23_PromBiv, 24_ReprPC, 25_Quies

FIG. 1D

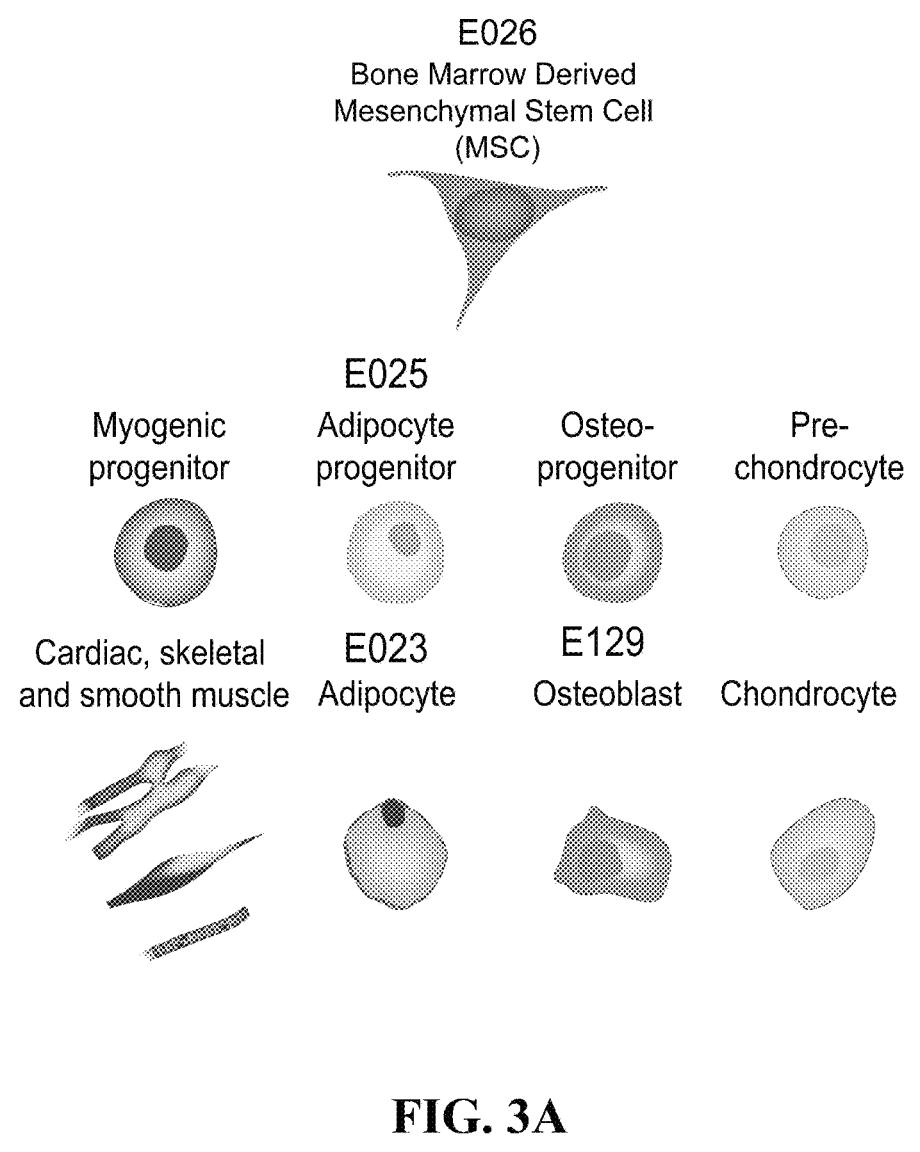

E026
Bone Marrow Derived
Mesenchymal Stem Cell
(MSC)

E025

| Myogenic progenitor | Adipocyte progenitor | Osteo-progenitor | Pre-chondrocyte |

| Cardiac, skeletal and smooth muscle | E023 Adipocyte | E129 Osteoblast | Chondrocyte |

FIG. 3A

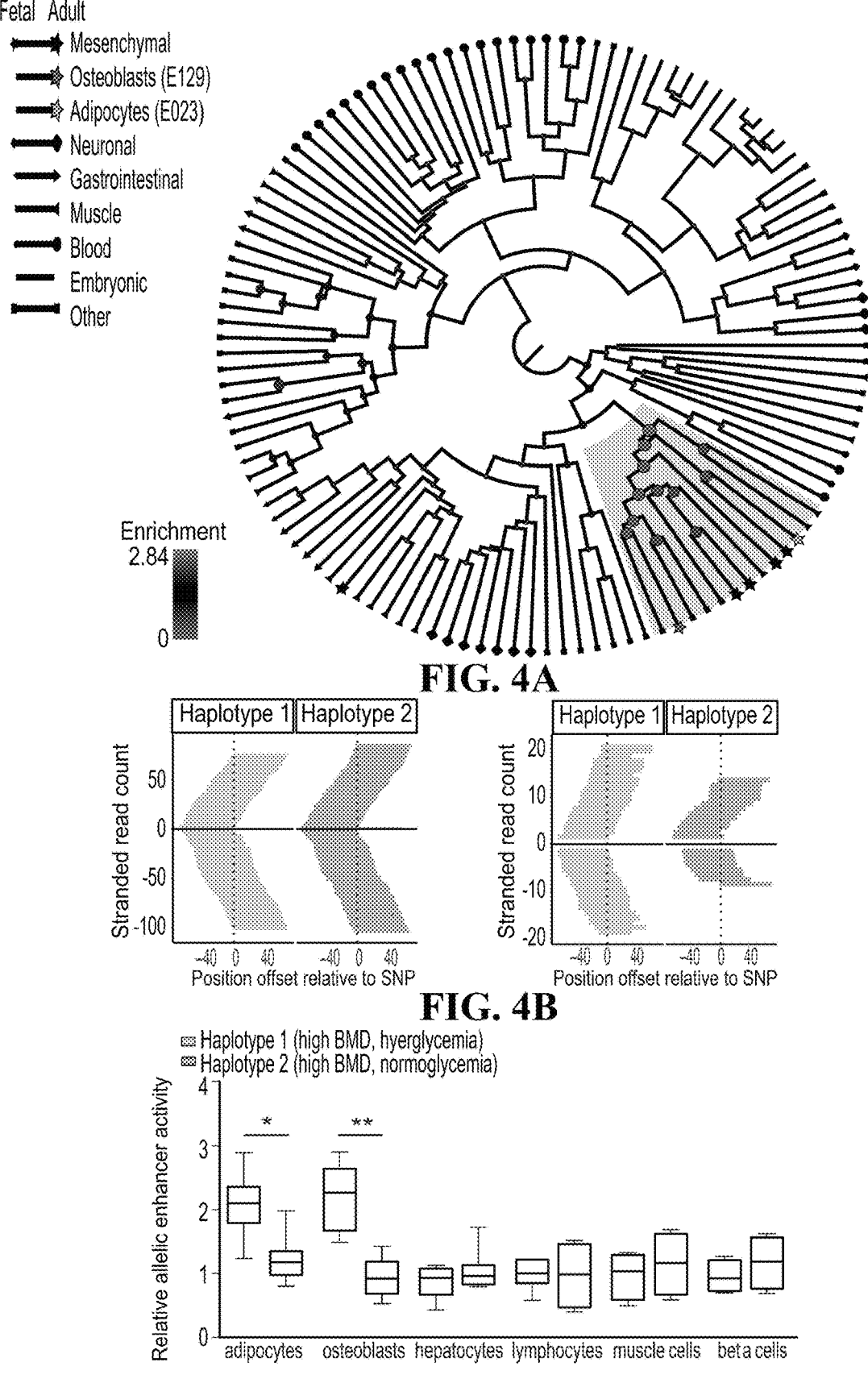

Fetal  Adult

Mesenchymal
Osteoblasts (E129)
Adipocytes (E023)
Neuronal
Gastrointestinal
Muscle
Blood
Embryonic
Other Enrichment
2.84

| Haplotype 1 | Haplotype 2 |

Stranded read count
50
0
-50
-100

-40  0  40    -40  0  40
Position offset relative to SNP

| Haplotype 1 | Haplotype 2 |

Stranded read count
20
10
0
-10
-20

-40  0  40    -40  0  40
Position offset relative to SNP

FIG. 4B

Haplotype 1 (high BMD, hyerglycemia)
Haplotype 2 (high BMD, normoglycemia)

Relative allelic enhancer activity
4
3
2
1
0

*        ** adipocytes  osteoblasts  hepatocytes  lymphocytes  muscle cells  beta cells

FIG. 4C

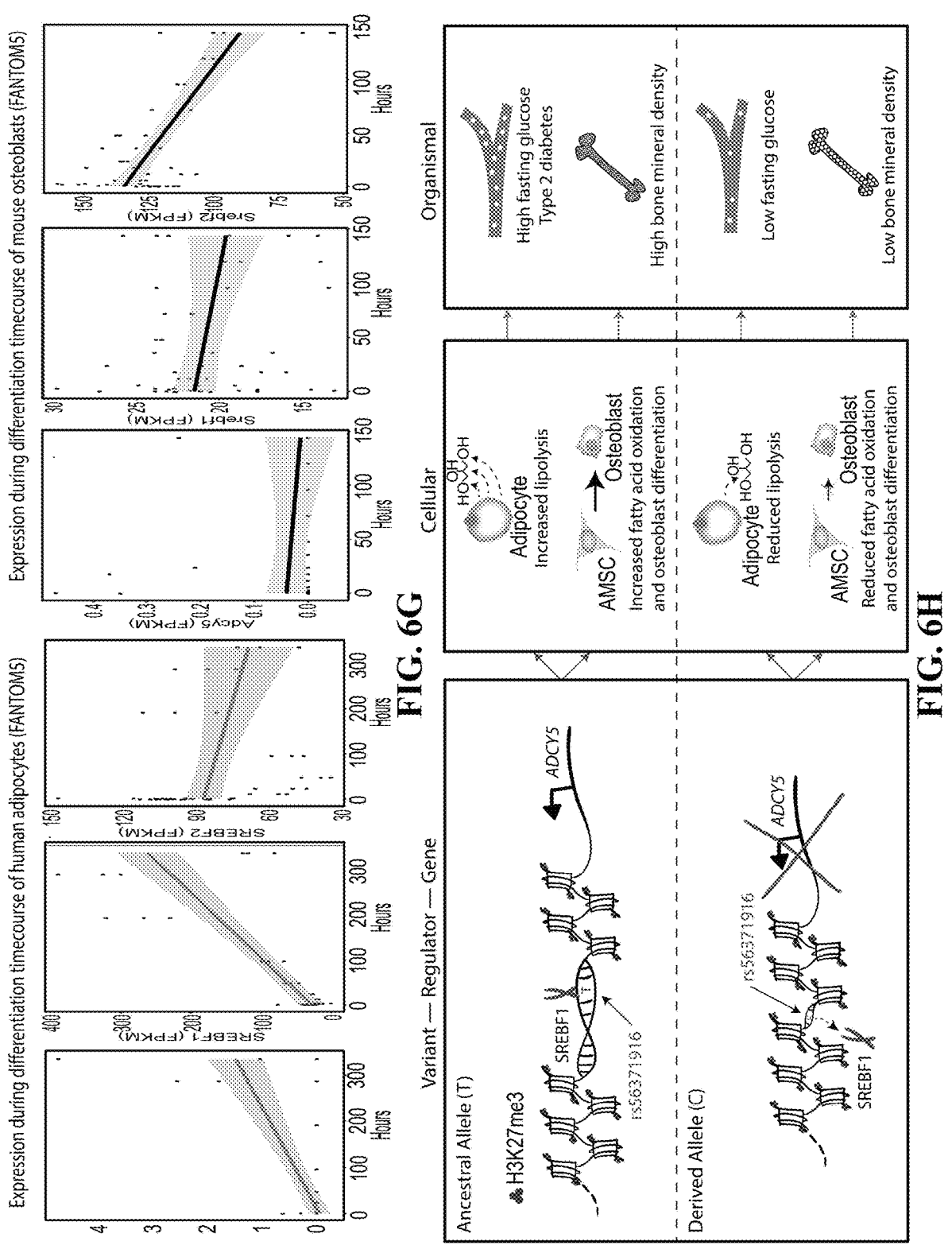

rs56371916 T allele (Haplotype 1), Day 0 rs56371916 T allele (Haplotype 1), Day 24 rs56371916 C allele (Haplotype 2), Day 24

SEQUENCE LISTING

```
<160> NUMBER OF SEQ ID NOS: 32

<210> SEQ ID NO 1
<211> LENGTH: 288
<212> TYPE: PRT
<213> ORGANISM: Artificial Sequence
<220> FEATURE:
<223> OTHER INFORMATION: Synthetic

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Pro Ala Pro Ser Pro Ala Phe
        50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
            115                 120                 125

Arg Pro Pro Arg Ala Lys Pro Ala Pro Arg Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
            195                 200                 205

Lys Tyr Gln Asp Met Ile Ala Ala Leu Pro Glu Ala Thr His Glu Ala
        210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285

<210> SEQ ID NO 2
<211> LENGTH: 183
<212> TYPE: PRT
<213> ORGANISM: Artificial Sequence
<220> FEATURE:
<223> OTHER INFORMATION: Synthetic
```

```
<400> SEQUENCE: 2

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
            35                  40                  45

Pro Ala Leu Ile Lys Arg Thr Asn Arg Arg Ile Pro Glu Arg Thr Ser
        50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
            115                 120                 125

Arg Trp Asp Arg Ile Leu Gln Ala Ser Gly Met Lys Arg Ala Lys Pro
        130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 20
<212> TYPE: DNA
<213> ORGANISM: Homo sapiens

<400> SEQUENCE: 3
ctgagtggaa atcaccgcca                                                    20

<210> SEQ ID NO 4
<211> LENGTH: 24
<212> TYPE: DNA
<213> ORGANISM: Homo sapiens

<400> SEQUENCE: 4
gtgaaaagta atcttcctgc ctgg                                               24

<210> SEQ ID NO 5
<211> LENGTH: 20
<212> TYPE: DNA
<213> ORGANISM: Homo sapiens

<400> SEQUENCE: 5
gtagtggcac tggaacttga                                                    20

<210> SEQ ID NO 6
<211> LENGTH: 20
<212> TYPE: DNA
<213> ORGANISM: Homo sapiens

<400> SEQUENCE: 6
gtgggtcagt cccaaatctt                                                    20
```

-continued

```
<210> SEQ ID NO 7
<211> LENGTH: 18
<212> TYPE: DNA
<213> ORGANISM: Homo sapiens

<400> SEQUENCE: 7
agtggaaatc accgccag                                                    18

<210> SEQ ID NO 8
<211> LENGTH: 20
<212> TYPE: DNA
<213> ORGANISM: Homo sapiens

<400> SEQUENCE: 8
agtggcactg gaacttgaac                                                  20

<210> SEQ ID NO 9
<211> LENGTH: 41
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Cy5-labeled DNA probe

<400> SEQUENCE: 9
tggccccaga gcagagtggc cggcgtgagt gaagatgatg a                          41

<210> SEQ ID NO 10
<211> LENGTH: 41
<212> TYPE: DNA
<213> ORGANISM: Homo sapiens

<400> SEQUENCE: 10
tcatcatctt cactcacgcc ggccactctg ctctggggcc a                         41

<210> SEQ ID NO 11
<211> LENGTH: 41
<212> TYPE: DNA
<213> ORGANISM: Homo sapiens
<220> FEATURE:
<221> NAME/KEY: misc_feature
<222> LOCATION: (1)..(1)
<223> OTHER INFORMATION: Cy5-labeled DNA probe

<400> SEQUENCE: 11
tggccccaga gcagagtggc tggcgtgagt gaagatgatg a                          41

<210> SEQ ID NO 12
<211> LENGTH: 41
<212> TYPE: DNA
<213> ORGANISM: Homo sapiens

<400> SEQUENCE: 12
tcatcatctt cactcacgcc agccactctg ctctggggcc a                         41

<210> SEQ ID NO 13
<211> LENGTH: 41
<212> TYPE: DNA
<213> ORGANISM: Homo sapiens

<400> SEQUENCE: 13
gtggccccag agcaggtggg gtgatgaaga tgatgaactg g                         41

<210> SEQ ID NO 14
```

```
<211> LENGTH: 41
<212> TYPE: DNA
<213> ORGANISM: Homo sapiens

<400> SEQUENCE: 14
ccagttcatc atcttcatca ccccacctgc tctggggcca c                          41

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tagaggtctc accccactca                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gaggggacac ctattcctag                                                  20

<210> SEQ ID NO 17
<211> LENGTH: 53
<212> TYPE: DNA
<213> ORGANISM: Homo sapiens

<400> SEQUENCE: 17
caagcagaag acggcatacg agataggagt ccgtctcgtg ggctcggaga tgt            53

<210> SEQ ID NO 18
<211> LENGTH: 53
<212> TYPE: DNA
<213> ORGANISM: Homo sapiens

<400> SEQUENCE: 18
caagcagaag acggcatacg agatcatgcc tagtctcgtg ggctcggaga tgt            53

<210> SEQ ID NO 19
<211> LENGTH: 53
<212> TYPE: DNA
<213> ORGANISM: Homo sapiens

<400> SEQUENCE: 19
caagcagaag acggcatacg agatgtagag aggtctcgtg ggctcggaga tgt            53

<210> SEQ ID NO 20
<211> LENGTH: 53
<212> TYPE: DNA
<213> ORGANISM: Homo sapiens

<400> SEQUENCE: 20
caagcagaag acggcatacg agatcctctc tggtctcgtg ggctcggaga tgt            53

<210> SEQ ID NO 21
<211> LENGTH: 53
<212> TYPE: DNA
<213> ORGANISM: Homo sapiens

<400> SEQUENCE: 21
```

-continued

```
caagcagaag acggcatacg agatagcgta gcgtctcgtg ggctcggaga tgt          53

<210> SEQ ID NO 22
<211> LENGTH: 53
<212> TYPE: DNA
<213> ORGANISM: Homo sapiens

<400> SEQUENCE: 22
caagcagaag acggcatacg agatcagcct cggtctcgtg ggctcggaga tgt          53

<210> SEQ ID NO 23
<211> LENGTH: 53
<212> TYPE: DNA
<213> ORGANISM: Homo sapiens

<400> SEQUENCE: 23
caagcagaag acggcatacg agatatcacg acgtctcgtg ggctcggaga tgt          53

<210> SEQ ID NO 24
<211> LENGTH: 53
<212> TYPE: DNA
<213> ORGANISM: Homo sapiens

<400> SEQUENCE: 24
caagcagaag acggcatacg agatacagtg gtgtctcgtg ggctcggaga tgt          53

<210> SEQ ID NO 25
<211> LENGTH: 53
<212> TYPE: DNA
<213> ORGANISM: Homo sapiens

<400> SEQUENCE: 25
caagcagaag acggcatacg agataggagt ccgtctcgtg ggctcggaga tgt          53

<210> SEQ ID NO 26
<211> LENGTH: 53
<212> TYPE: DNA
<213> ORGANISM: Homo sapiens

<400> SEQUENCE: 26
caagcagaag acggcatacg agatcatgcc tagtctcgtg ggctcggaga tgt          53

<210> SEQ ID NO 27
<211> LENGTH: 53
<212> TYPE: DNA
<213> ORGANISM: Homo sapiens

<400> SEQUENCE: 27
caagcagaag acggcatacg agatcctctc tggtctcgtg ggctcggaga tgt          53

<210> SEQ ID NO 28
<211> LENGTH: 53
<212> TYPE: DNA
<213> ORGANISM: Homo sapiens

<400> SEQUENCE: 28
caagcagaag acggcatacg agatagcgta gcgtctcgtg ggctcggaga tgt          53

<210> SEQ ID NO 29
<211> LENGTH: 53
<212> TYPE: DNA
<213> ORGANISM: Homo sapiens
```

-continued

```
<400> SEQUENCE: 29
caagcagaag acggcatacg agatcagcct cggtctcgtg ggctcggaga tgt          53

<210> SEQ ID NO 30
<211> LENGTH: 53
<212> TYPE: DNA
<213> ORGANISM: Homo sapiens

<400> SEQUENCE: 30
caagcagaag acggcatacg agattgcctc ttgtctcgtg ggctcggaga tgt          53

<210> SEQ ID NO 31
<211> LENGTH: 53
<212> TYPE: DNA
<213> ORGANISM: Homo sapiens

<400> SEQUENCE: 31
caagcagaag acggcatacg agattcctct acgtctcgtg ggctcggaga tgt          53

<210> SEQ ID NO 32
<211> LENGTH: 53
<212> TYPE: DNA
<213> ORGANISM: Homo sapiens

<400> SEQUENCE: 32
caagcagaag acggcatacg agatatcacg acgtctcgtg ggctcggaga tgt          53
```

METHODS FOR TREATING METABOLIC DISORDERS BY TARGETING ADCY5

CROSS-REFERENCE TO RELATED APPLICATIONS

This application claims the benefit of U.S. Provisional Application No. 62/855,780, filed May 31, 2019. The entire contents of the above-identified application are hereby fully incorporated herein by reference.

STATEMENT AS TO FEDERALLY FUNDED RESEARCH

This invention was made with government support under Grant No. R01 AR041398 awarded by the National Institutes of Health. The government has certain rights in the invention.

REFERENCE TO AN ELECTRONIC SEQUENCE LISTING

The contents of the electronic sequence listing (BROD_4070WP_ST25.txt; size is 9,361 bytes and it was created on May 18, 2020) is herein incorporated by reference in its entirety.

TECHNICAL FIELD

The subject matter disclosed herein is generally directed to treating metabolic disorders by modulating the activity or expression of a gene.

BACKGROUND

Patients with Type 2 Diabetes (T2D) have increased bone mineral density (BMD) yet greater susceptibility to fracture (Vestergaard 2007). This perplexing finding suggests an intimate link between skeletal and metabolic traits. While some have suggested that this observation implies shared genetic etiology between skeletal and metabolic traits in humans (Vestergaard 2007; Billings et al. 2012), the connection between the molecular and cellular mechanisms underlying T2D and BMD remains unknown, and no systematic studies of their shared genetics have been published. Large-effect genetic variants that alter both bone and glycemic traits could elucidate the mechanism by which the sharing occurs.

Genome wide association studies (GWAS) have identified tens of thousands of genomic loci underlying individual human traits, including BMD and T2D. However, these GWAS loci have only rarely been resolved into causal variants or mechanisms due to several challenges (Eichler et al. 2010). The vast majority of loci involve non-coding variants that likely act through regulatory changes (over 80% of loci contain no protein-altering common variants, even when considering all variants in linkage disequilibrium (LD) at r2≥0.8 (Hindorff et al. 2009), making it difficult to pinpoint the causal variants, regulatory circuits, relevant cell types and tissues, key developmental stages, and affected cellular functions (Cai et al. 2003; Claussnitzer et al. 2015; Steidl et al. 2007). Moreover, there is growing evidence of pervasive pleiotropy, with single genetic variants affecting two or more seemingly unrelated traits (Sivakumaran et al. 2011). In fact, hundreds of individual variants identified from GWAS are associated with multiple traits (Bulik-Sullivan et al. 2015), with effects in multiple cell types. New approaches to dissecting risk loci are needed. A systematic study of pleiotropic loci represents an opportunity to discover biological mechanisms underlying the individual traits and further mechanisms that link the individual traits.

SUMMARY

In one aspect, the invention provides a method for controlling a rate of fatty acid oxidation in mesenchymal cells, comprising modulating the expression or activity of ADCY5. The rate of fatty acid oxidation may be decreased by reducing the expression or activity of ADCY5. The rate of fatty acid oxidation may be increased by increasing the expression or activity of ADCY5.

In some embodiments, the mesenchymal cell may be a mesenchymal stem cell, an adipocyte, an osteoblast, a chondrocyte, or a myocyte.

In some embodiments, controlling the rate of fatty acid oxidation in mesenchymal stem cells comprises inhibiting fatty acid oxidation. In some embodiments, inhibiting fatty acid oxidation prevents development of Type 2 Diabetes (T2D).

In some embodiments, controlling the rate of fatty acid oxidation in mesenchymal stem cells may comprise increasing the rate of fatty acid oxidation. Increasing the rate of fatty acid oxidation may promote bone formation.

In another aspect, the invention provides a method of treating a metabolic disorder in a patient in need thereof comprising modulating the expression of ADCY5 in a cell.

In some embodiments, the cell may be an adipocyte, and modulating the expression or activity of ADCY5 may comprise increasing the expression or activity of ADCY5.

In some embodiments, the cell may be an osteoblast, and modulating the expression or activity of ADCY5 may comprise decreasing the expression or activity of ADCY5.

In some embodiments, the metabolic disorder may comprise high bone mineral density and hyperglycemia. In some embodiments, the metabolic disorder is Type 2 Diabetes.

In yet another aspect, the invention provides a method of regulating fasting glucose levels in a subject in need thereof by modulating the expression or activity of ADCY5 in adipocytes.

In some embodiments, modulating may comprise decreasing fasting glucose level by decreasing the expression or activity of ADCY5 in adipocytes.

In some embodiments, modulating may comprise increasing fasting glucose levels by increasing the expression or activity of ADCY5 in adipocytes.

In yet another aspect, the invention provides a method of regulating bone growth rates in a subject in need thereof by modulating the expression or activity of ADCY5 in osteoblasts.

In some embodiments, modulating may comprise promoting bone growth by increasing the expression or activity of ADCY5 in osteoblasts.

In some embodiments, modulating may comprise inhibiting or reducing a rate of bone growth by decreasing the expression or activity of ADCY5 in osteoblasts.

Reducing or inhibiting the activity of ADCY5 may be achieved using a modulating agent such as a therapeutic antibody, antibody fragment, antibody-like protein scaffold, aptamer, protein, CRISPR system or small molecule. In some embodiments, the small molecule is etomoxir.

In some embodiments, modulating may comprise administering one or more modulating agents that modulate the expression or activity of ADCY5.

In some embodiments, the one or more modulating agents comprises a therapeutic antibody, antibody fragment, antibody-like protein scaffold, aptamer, polypeptide, protein, genetic modifying agent, small molecule, small molecule degrader, or combination thereof.

In some embodiments, modulating may comprise introducing a mutation or base edit that modulates ADCY5 expression. The mutation or base edit may be introduced using a CRISPR-Cas system, RNAi system, a TALEN, a Zn-finger nuclease, or a meganuclease. The base edit may be made to genomic DNA or expressed RNA using a CRISPR-Cas system.

The mutation or base edit may change a C to T at rs5637196 to increase ADCY5 expression or it may change a T to C at rs5637196 to decrease ADCY5 expression.

Modulating may be done either in vivo or ex vivo.

In yet another aspect, the invention provides a method of producing a population of cells comprising an engineered mutation in the SNP variant rs56371916.

The mutation may be engineered using genome editing methods or by use of a CRISPR-Cas system, an inactivated CRISPR-Cas system, a Cas protein, a zinc finger protein (ZFP), a zinc finger nuclease (ZFN), a transcription activator-like effector (TALE), a transcription activator-like effector nuclease (TALEN), or a meganuclease.

The engineered mutation may effect a reduction or inhibition of the expression or activity of ADCY5. In some embodiments, the mutation may comprise a T to C single nucleotide substitution. In some embodiments, the engineered mutation may increase the expression or activity of ADCY5.

In yet another aspect, the invention provides a population of cells produced by the method described above.

In some embodiments, the engineered mutation may lead to increased fatty acid metabolism. In some embodiments, the engineered mutation may lead to decreased fatty acid metabolism.

In yet another aspect, the invention provides a method of treating a metabolic disorder in a patient in need thereof comprising determining the patient's haplotype at the 3q21.1 locus and administering a therapeutically effective amount of an agent capable of modulating the expression or activity of ADCY5 if the patient is homozygous for a haplotype characteristic of high bone mineral density and increased hyperglycemia.

In yet another aspect, the invention provides a kit comprising reagents to determine the haplotype according to the above described method.

The kit may comprise primers and/or probes for quantitative RT-PCR or fluorescently bar-coded oligonucleotide probes for hybridization to RNA.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1A-1E—(1A) Manhattan plot of genome-wide association results for bone density and glycemic traits using CP-ASSOC. Bivariate associations were computed for two bone density traits (FNBMD and LSBMD) and four glycemic traits (HOMA-IR, HOMA-B, fasting glucose levels, and fasting insulin levels). The x-axis is chromosomal position, and the y-axis is the significance on a −log 10 scale. The dashed red line marks the threshold for declaring genome-wide suggestive significance (pp=$5 \times 10^{-6}$). (1B) Heritability partitioning across the entire bivariate GWAS to find enriched cell type groups. In the category 'other' three of the top individual cell types are adipose nuclei. The category 'Mesenchymal' comprises an additional category above the standard ten (Finucane et al. 2015): bone marrow derived stem cells, adipose-derived mesenchymal stem cells, adipocytes, osteoblasts, chondrocytes, and skeletal myocytes. Error bars represent jackknife standard errors. The black dotted line at −log 10(P)=3.25 is the cutoff for Bonferroni significance. (1C) Heritability partitioning for mesenchymal versus non-mesenchymal cell type groups for diverse histone marks. All mesenchymal annotations (described above) versus the non-mesenchymal annotations for each histone modification are compared. In all cases, the mesenchymal cell type annotations are significantly more enriched for heritability than non-mesenchymal cell type annotations, particularly for H3K4me1 and H3K27ac. (1D) The annotation panel for the twenty-five state chromatin model. Rows represent states and columns are emission parameters (left table) and enrichments of relevant genomic annotations (right panel). (1E) Allele-specific DNase I hypersensitivity analyses in skeletal muscle derived MSCs heterozygous for haplotype 1, focusing on a 10 kb region containing the SNPs in tightest LD with rs2124500. Plots depict the estimated allelic proportion of DNase-Seq reads originating from each allele. Allelic imbalance of chromatin accessibility was assessed in skeletal muscle-derived MSCs (Maurano et al. 2015) from a single individual heterozygous for rs2124500 and SNPs in tightest LD. Number of reads covering each allele were counted (71 vs 37 reads) and a binomial test comparing the observed proportion of reference allele counts with the expected proportion was calculated (p=0.0014).

FIG. 3A-3B—(3A) Lineage relationships of mesenchymal stem cells (MSCs) and MSC-derived lineages, including adipocytes involved in hyperglycemia and osteoblasts involved in bone formation. Epigenome identity (EID) numbers correspond to Roadmap Epigenomics numbering of reference epigenomes. E114-E129 correspond to ENCODE project reference epigenomes. (3B) Morphological changes of primary human AMSCs during differentiation into mature adipocytes and osteoblasts, respectively. Unstained bright field microscopy-based pictures are shown as well as Oil-Red-O based lipid staining for adipocyte differentiation and Alkaline Phosphatase Staining as well as Alizarin Red staining for osteoblast differentiation.

FIG. 4A-4G—ADCY5 expression differences between haplotypes in adipocytes and osteoblasts. (4A) H3K27me3 enrichment analysis at 3q21.1. Observed H3K27me3 fold enrichment tracks from Roadmap were averaged around rs56371916 T/C for each non-cancer/transformed uniformly processed epigenome. Using the H3K27me3 derived clustering from Roadmap, enrichments were plotted, in each clade, for average signal within that clade versus average signal for all other epigenomes. Node size and color are proportional to the enrichment, and the highlighted clade contains the mesenchymal-derived cell lineages. (4B) Allelic imbalance in H3K27me3 ChIP-Seq reads and ATAC-Seq reads in AMSCs from a heterozygote for haplotype 1, focusing on a 10 kb region containing the SNPs in tightest LD with rs2124500 (r2>0.9). Plots depict the estimated allelic proportion of ChIP-seq and ATAC-seq reads originating from each allele. Number of reads covering each allele were counted for ChIP (129129 vs 147 reads) and ATAC (3737 vs 19 reads) and a binomial test comparing the observed proportion of reference allele counts with the expected proportion was calculated (p=0.31 for ChIP, p=0.02 for ATAC). (4C) Luciferase assays for 10 kb fragments containing 10 candidate regulatory SNPs in tightest LD with rs2124500 (r2>0.9) in adipocytes, osteoblasts, hepatocytes, lymphocytes, differentiated muscle cells and pancreatic beta cells. (4D) Genome-wide higher order chromatin interactions for the ADCY5 locus analyzed by Hi-C assays in human embryonic stem cell derived mesenchymal stem cells isolated from an individual homozygous for haplotype 1 (Dixon et al. 2015). (4E) Relative gene expression of differentiation marker genes in adipocytes and osteoblasts, which were differentiated from primary AMSCs (day 0) to differentiated adipocytes and osteoblasts (day 14). (4F) Haplotype-dependent differential gene expression for six potential target genes across a 1 Mb region centered on the 3q21.1 locus. Bar plots depict relative gene expression±SD using HPRT for normalization. Assays were performed in cells from 18 heterozygous individuals (haplotypes 1/2) and 23 homozygous individuals (haplotypes 1/1) at day 3 of osteoblast differentiation. (4G) Haplotype-dependent differential gene expression of ADCY5 in undifferentiated adipose-derived AMSCs, differentiated adipocytes and osteoblasts. Quantitative PCR mRNA levels (y-axis, HPRT normalized) in primary cells from individuals heterozygous (dark blue, n=18) and homozygous (light blue, n=23) for haplotype 1.

FIG. 6A-6H—(6A) rs56371916 allelic effect at 3q21.1 using the CNN-based method Basset. Predicted SNP accessibility difference (SAD) between alleles was correlated with average predicted accessibility at each SNP. rs56371916 had higher correlation (0.957; p=0.04) than any other SNP in the LD block. (6B) Distribution of predicted SNP accessibility for 29472 trait-associated SNPs in the GWAS catalog. rs56371916 had significantly higher SAD-SAD scores at day 24 of adipogenesis (empirical p-value=0.0061). (6C) Luciferase assays for 1 kb on rs56371916 in adipocytes, osteoblasts. Luciferase enhancer reporters indicate the degree of allele-specific regulatory activity at a given locus. DNA from individuals homozygous for each haplotype was amplified and cloned into a luciferase reporter plasmid, and reported on in SGBS and MC3T3 cells. Measured is the total luminescence from each allele in both lines. (6D) Competition EMSA assays using adipocyte nuclear extract. Competition assays were performed by adding 11-, 33-, 100-, and 200-molar excess of unlabeled probes. Differential binding of SREBP1 to the T allele was competed away with increasing amount of unlabeled probe, clearly visible with nuclear extract from day 10 of differentiation. (6E) Correlation (Pearson's r) of ADCY5 mRNA with SREBP1 mRNA in human whole subcutaneous adipose tissue and subcutaneous adipose stromal cells from 24 lean individuals, respectively, measured by Illumina microarrays. (6F) Correlation (Pearson's r) of ADCY5 mRNA with SREBP2 mRNA in human whole subcutaneous adipose tissue and subcutaneous adipose stromal cells from 24 lean individuals, respectively, measured by Illumina microarrays. (6G) Expression from FANTOM of ADCY5, SREBP1, and SREBP2 in differentiating human adipocytes (yellow background) and differentiating mouse osteoblasts (blue background). Data are taken directly from FANTOM tables. (6H) Schematic regulatory model of the ADCY5 bivariate locus effects.

FIG. 9A-9E—3q21.1 haplotype affects lipid oxidation in adipocytes and osteoblasts. (9A) Osteoblast alkaline phosphatase (ALP) activity in primary differentiating osteoblasts treated with 100 μM etomoxir (carnitine palmitoyltransferase 1 antagonist) or negative control. Assays were performed in cells from 18 heterozygous individuals (haplotypes 1/2) and 23 homozygous individuals (haplotypes 1/1) and differentiating osteoblasts were treated between day 2 and day 5 of differentiation. (9B) Oxidation of [14C]palmitate (0.5 mM) to 14CO2 in primary differentiating osteoblasts treated with 100 μM etomoxir (carnitine palmitoyltransferase 1 antagonist) or negative control. Assays were performed in cells from 4 heterozygous individuals (haplotypes 1/2) and 4 homozygous individuals (haplotypes 1/1) and differentiating osteoblasts were treated between day 2 and day 5 of differentiation. Bar plots depict [14C]palmitate oxidation normalized to protein concentration. (9C) Fuel oxidation in murine bone marrow cells undergoing osteoblast differentiation. ATP generation changes from a combination of glycolysis and lipid oxidation at day 0 to primarily lipid oxidation at day 2, returning to a combination of the two on day 7. Primary mouse bone marrow stromal cells (BMSCs) cultured for 0, 2, or 7 days in osteogenic medium. Seahorse XF24 Flux analyzer was performed at each time point and contribution of ATP generation was calculated from glycolysis vs. oxidative phosphorylation. (9D) Generation of isogenic AMSCs with genotype TT at rs56371916 starting from a CC homozygote. Isogenic lines were differentiated to osteoblasts after undergoing clonal expansion, and marker gene expression for osteoblast differentiation was measured by qPCR. (9E) Generation of isogenic AMSCs with genotype CC at rs56371916 starting from a TT homozygote. Isogenic lines were differentiated to adipocytes after undergoing clonal expansion, and catecholamine-stimulated lipolysis was measured.

Figures 1A, 1B:
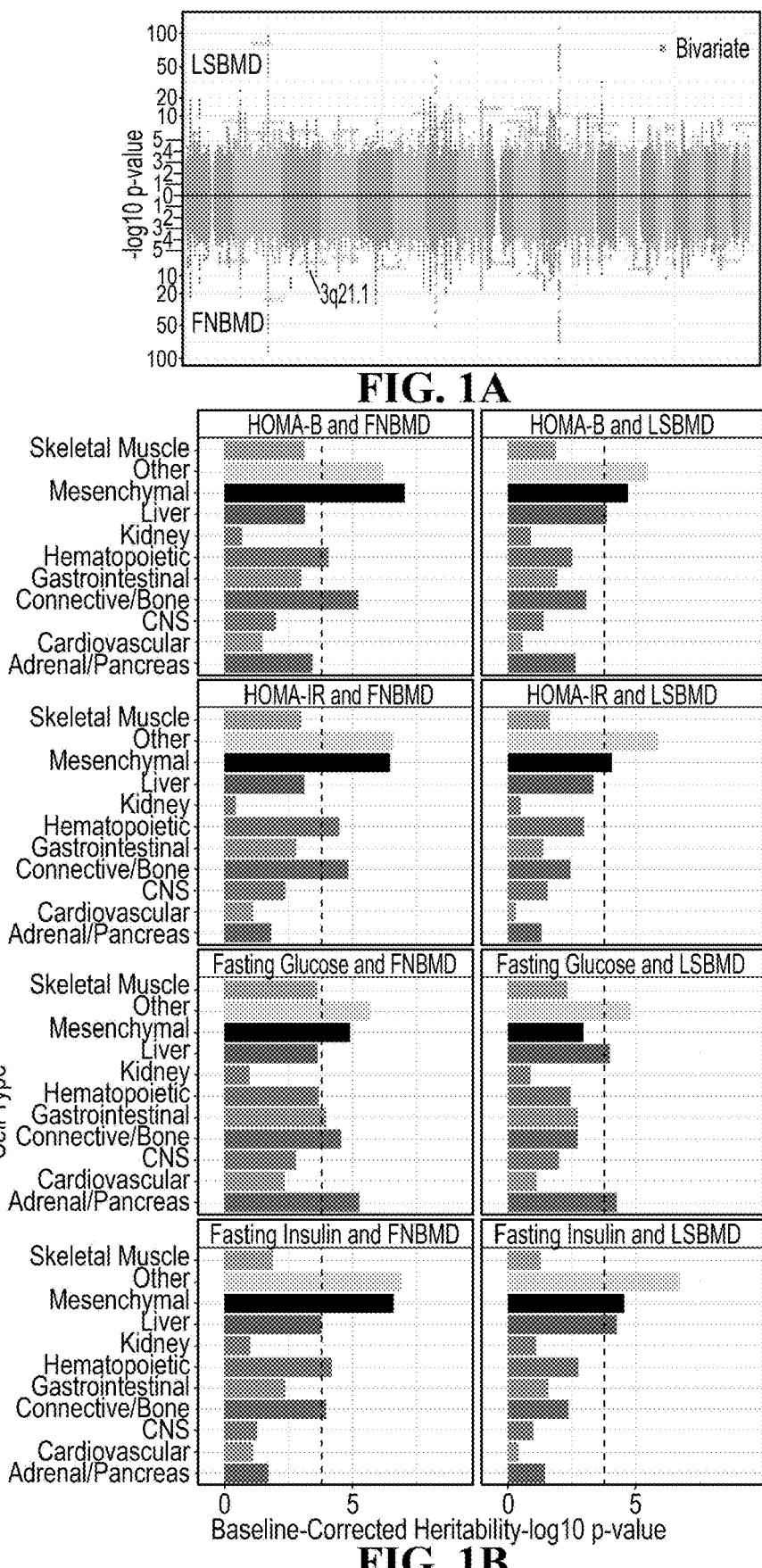

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

GWAS summary statistics are used to identify genetic loci that may have pleiotropic effects on skeletal and glycemic traits. Applicants used femoral neck BMD and lumbar spine BMD as quantitative endophenotypes that are strongly predictive of osteoporotic fracture, and fasting glucose, fasting insulin, HOMA-IR and HOMA-B to define T2D. The functional basis of the most intriguing bivariate GWAS locus, at 3q21.1 was elucidated, which was associated with femoral neck BMD and fasting glucose. The GWAS signal was driven by rs56371916, an intronic variant in Adenylate Cyclase 5 (ADCY5) that alters the binding affinity of Sterol Regulatory Element Binding Protein 1 (SREBP1), and leads to differential ADCY5 gene expression and cell-autonomous change in fatty acid metabolism in mature adipocytes and differentiating osteoblasts. Importantly, the disruption of the regulator SREBP1, the variant rs56371916 and the target gene ADCY5 each cause cellular changes (e.g., lipid oxidation) relevant for BMD and T2D. Disclosed herein is a novel link between fatty acid oxidation and osteoblast differentiation. More generally, a framework is introduced to uncover novel biological mechanisms, by identification and functional dissection of pleiotropic GWAS loci.

Methods for controlling rates of fatty acid oxidation in mesenchymal cells are provided. The rate of fatty acid oxidation can be controlled according to the methods disclosed herein by modulating the expression or activity of ADCY5. Methods of treating a metabolic disorder in a patient are also provided comprising regulating the expression or activity of ADCY5. The metabolic disorder can be high bone mineral density or hyperglycemia. Methods of treating a metabolic disorder in a patient may include determining the patient's haplotype at the 3q21.1 locus and administering a therapeutically effective amount of an agent capable of modulating the expression or activity of ADCY5 if the patient is homozygous for a haplotype characteristic of high bone mineral density and increased hyperglycemia. Further methods provided herein comprise regulating bone growth rates and modulating fasting glucose levels by modulating the expression or activity of ADCY5.

Methods of modulating the expression or activity of ADCY5 are provided, which may comprise increasing or decreasing the expression or activity of ADCY5 and can be achieved by administration of a modulating agent. Modulating may also comprise introducing a mutation or base edit that modulated ADCY5 expression, which can be introduced using a CRISPR-Cas system, RNAi system, a TALEN, a Zn-finger nuclease, or a meganuclease.

ADCY5

The ADCY5 gene encodes an enzyme called adenylate cyclase 5. This enzyme helps convert a molecule called adenosine triphosphate (ATP) to another molecule called cyclic adenosine monophosphate (cAMP). ATP is a molecule that supplies energy for cells' activities, including muscle contraction, and cAMP is involved in signaling for many cellular functions.

Certain polymorphisms in the ADCY5 gene have been associated with an increased risk of type 2 diabetes (T2D), which is the most common form of diabetes and results in impaired control of blood sugar. cAMP normally increases in response to increases in blood sugar and is involved in signaling that stimulates the production of insulin. Data suggest that the polymorphisms associated with increased type 2 diabetes risk may decrease the ability of the adenylate cyclase 5 enzyme to produce cAMP, resulting in the abnormal response to sugar that occurs in type 2 diabetes.

Genome Wide Association Studies (GWAS) have identified genetic loci that may have pleiotropic effects on skeletal and glycaemic traits. Femoral neck bone mass density (BMD) and lumbar spine BMD as quantitative endophenotypes are strongly predictive of osteoporotic fracture, and fasting glucose, fasting insulin, HOMA-IR and HOMA-B to define T2D. The functional basis of the most intriguing bivariate GWAS locus, at 3q21.1 has been elucidated, which is associated with femoral neck BMD and fasting glucose. The GWAS signal was driven by rs56371916, an intronic variant in Adenylate Cyclase 5 (ADCY5) that alters the binding affinity of Sterol Regulatory Element Binding Protein 1 (SREBP1), and leads to differential ADCY5 gene expression and cell-autonomous change in fatty acid metabolism in mature adipocytes and differentiating osteoblasts. Importantly, disruption of the regulator SREBP1, the variant rs56371916 and the target gene ADCY5 each cause cellular changes (e.g., lipid oxidation) relevant for BMD and T2D. Shown herein is a link between fatty acid oxidation and osteoblast differentiation. More generally, shown is a framework to uncover novel biological mechanisms, by identification and functional dissection of pleiotropic GWAS loci.

Genetic mutations in the ADCY5 gene have also been associated with ADCY5-related dyskinesia, a disorder that causes abnormal involuntary movements. At least six ADCY5 gene mutations have been identified in people with ADCY5-related dyskinesia. These mutations are thought to enhance adenylate cyclase 5 enzyme activity and lead to higher levels of cAMP within cells, so they are described as "gain-of-function" mutations. Other ADCY5 gene mutations prevent production of adenylate cyclase 5.

Methods for Controlling the Rate of Fatty Acid Oxidation

In some embodiments, the invention provides methods for controlling a rate of fatty acid oxidation in mesenchymal cells. Such methods may comprise modulating the expression or activity of ADCY5. As used herein, the term "modulate" includes up-regulation and down-regulation, e.g., enhancing or inhibiting a response; reducing, decreasing or increasing the expression or activity of a protein, enzyme, or other element.

Fatty acids are a family of molecules classified within the lipid macronutrient class. In animal metabolism, fatty acids participate in energy production, captured in the form of adenosine triphosphate (ATP). When compared to other macronutrient classes (carbohydrates and protein), fatty acids yield the most ATP on an energy per gram basis, when they are completely oxidized to $CO_2$ and water by beta oxidation and the citric acid cycle. Mainly in the form of triglycerides, fatty acids are the foremost storage form of fuel in most animals, and to a lesser extent in plants. In addition, fatty acids are important components of the phospholipids that form the phospholipid bilayers out of which all the membranes of the cell are constructed (the cell wall, and the membranes that enclose all the organelles within the cells, such as the nucleus, the mitochondria, endoplasmic reticulum, and the Golgi apparatus). Fatty acids can also be cleaved, or partially cleaved, from their chemical attachments in the cell membrane to form second messengers within the cell and local hormones in the immediate vicinity of the cell. The prostaglandins made from arachidonic acid stored in the cell membrane are probably the best known group of these local hormones. Fatty acid metabolism or oxidation consists of catabolic processes that generate energy, and anabolic processes that create biologically important molecules, such as triglycerides, phospholipids, second messengers, local hormones and ketone bodies.

Mesenchymal Cells

Mesenchymal stem cells are multipotent stromal cells that can differentiate into a variety of cell types, including osteoblasts (bone cells), chondrocytes (cartilage cells), myocytes (muscle cells) and adipocytes, which are fat cells that give rise to marrow adipose tissue. The bone marrow (BM) stroma contains a heterogeneous population of cells, including endothelial cells, fibroblasts, adipocytes and osteogenic cells, and it was initially thought to function primarily as a structural framework upon which hematopoiesis occurs. However, it turns out that at least two distinct stem cell populations reside in the bone marrow of many mammalian species: hematopoietic stem cells (HSCs) and mesenchymal stem cells (MSCs), with the latter responsible for the maintenance of the non-hematopoietic bone marrow cells. MSCs, also termed multipotent marrow stromal cells or mesenchymal stromal cells, are a heterogeneous population of plastic-adherent, fibroblast-like cells, which can self-renew and differentiate into bone, adipose and cartilage tissue in culture. Single cell suspensions of BM stroma can generate colonies of adherent fibroblast-like cells in vitro. These colony-forming unit fibroblasts (CFU-Fs) are capable of osteogenic differentiation and provide evidence for a clonogenic precursor for cells of the bone lineage. Functional in vitro characterization of the stromal compartment has also revealed its importance in regulating the proliferation, differentiation and survival of HSCs. CFU-F initiating cells in vivo have been shown to be quiescent, existing at a low frequency in human bone marrow.

Although MSCs are traditionally isolated from bone marrow, cells with MSC-like characteristics have been isolated from a variety of fetal, neonatal and adult tissues, including cord blood, peripheral blood, fetal liver and lung, adipose tissue, compact bone, dental pulp, dermis, human islet, adult brain, skeletal muscle, amniotic fluid, synovium, and the circulatory system. There is evidence indicating a perivascular location for these MSC-like cells in all tissues, implying that all MSCs are pericytes that closely encircle endothelial cells in capillaries and microvessels in multiple organs. Pericytes are thought to stabilize blood vessels, contribute to tissue homeostasis under physiological conditions, and play an active role in response to focal tissue injury through the release of bioactive molecules with trophic and immunomodulatory properties. Pericytes and adventitial cells also natively express mesenchymal markers and share similar gene expression profiles as well as developmental and differentiation potential with mesenchymal cells. Pericytes may represent a subpopulation of the total pool of assayable MSCs at least within the bone marrow.

In some embodiments, the rate of fatty acid oxidation is decreased by reducing the expression or activity of ADCY5. In some embodiments, the rate of fatty acid oxidation may be increased by increasing the expression or activity of ADCY5.

In specific embodiments, the mesenchymal cell may be a mesenchymal stem cell, an adipocyte, an osteoblast, a chondrocyte, or a myocyte. Mesenchymal stem cells can differentiate into adipocytes, connective tissue, muscle or bone.

As described herein, adipocytes, also known as lipocytes and fat cells, are the cells that primarily compose adipose tissue, and they specialize in storing energy as fat. Adipocytes are derived from mesenchymal stem cells which give rise to adipocytes, osteoblasts, myocytes and other cell types through adipogenesis. Pre-adipocytes are undifferentiated fibroblasts that can be stimulated to form adipocytes. Although the exact lineage of adipocyte is still unclear, recent studies shed light into potential molecular mechanisms in the fate determination of pre-adipocytes. The variation of body fat distribution resulting from normal growth is influenced by nutritional and hormonal status in dependence on intrinsic differences in cells found in each adipose depot.

Obesity is characterized by the expansion of fat mass, through increase in size of adipocytes and, to a lesser extent, cell proliferation. The fat cells of obese individuals exhibit increased production of metabolism modulators, such as glycerol, hormones, macrophage stimulating chemokines, and pro-inflammatory cytokines, leading to the development of insulin resistance. Fat production in adipocytes is strongly stimulated by insulin. By controlling the activity of the pyruvate dehydrogenase and the acetyl-CoA carboxylase enzymes, insulin promotes unsaturated fatty acid synthesis. It also promotes glucose uptake and induces SREBF1, which activates the transcription of genes that stimulate lipogenesis.

Osteoblasts are cells that synthesize bone. In the process of bone formation, osteoblasts function in groups of connected cells because individual cells cannot make bone. A group of organized osteoblasts together with the bone made by a unit of cells is usually called the osteon. Osteoblasts are specialized, terminally differentiated products of mesenchymal stem cells. They synthesize dense, crosslinked collagen and specialized proteins in much smaller quantities, including osteocalcin and osteopontin, which compose the organic matrix of bone. In organized groups of connected cells, osteoblasts produce hydroxylapatite that is deposited, in a highly regulated manner, into the organic matrix forming a strong and dense mineralized tissue—the mineralized matrix. The mineralized skeleton is the main support for the bodies of air breathing vertebrates and is an important store of minerals for physiological homeostasis including both acid-base balance and calcium or phosphate maintenance.

Bone is a dynamic tissue that is constantly being reshaped by osteoblasts, which produce and secrete matrix proteins and transport mineral into the matrix, and osteoclasts, which break down the tissues. Osteoblasts are the major cellular component of bone and they arise from mesenchymal stem cells (MSC). MSC give rise to osteoblasts, adipocytes, and myocytes among other cell types. Osteoblast quantity is understood to be inversely proportional to that of marrow adipocytes which comprise marrow adipose tissue (MAT). Osteoblasts are found in large numbers in the periosteum, the thin connective tissue layer on the outside surface of bones, and in the endosteum. Normally, almost all of the bone matrix is mineralized by the osteoblasts. Before the organic matrix is mineralized, it is called the osteoid. Osteoblasts buried in the matrix are called osteocytes. During bone formation, the surface layer of osteoblasts consists of cuboidal cells, called active osteoblasts. When the bone-forming unit is not actively synthesizing bone, the surface osteoblasts are flattened and are called inactive osteoblasts. Osteocytes remain alive and are connected by cell processes to a surface layer of osteoblasts. Osteocytes have important functions in skeletal maintenance.

Osteoclasts break down bone tissue, and along with osteoblasts and osteocytes, form the structural components of bone. In the hollow within bones are many other cell types of the bone marrow. Components that are essential for osteoblast bone formation include mesenchymal stem cells (osteoblast precursor) and blood vessels that supply oxygen and nutrients for bone formation. Bone is a highly vascular tissue, and active formation of blood vessel cells, also from mesenchymal stem cells, is essential to support the metabolic activity of bone. The balance of bone formation and bone resorption tends to be negative with age, particularly in post-menopausal women, often leading to a loss of bone serious enough to cause fractures, which is called osteoporosis.

Bone is formed by one of two processes: endochondral ossification or intramembranous ossification. The usual method is endochondral ossification, the process of forming bone from cartilage. This form of bone development is the more complex form because it follows the formation of a first skeleton of cartilage made by chondrocytes, which is then removed and replaced by bone, made by osteoblasts. Intramembranous ossification is the direct ossification of mesenchyme as happens during the formation of the membrane bones of the skull and others. During osteoblast differentiation, the developing progenitor cells express the regulatory transcription factor Cbfa1/Runx2. An additional required transcription factor is Sp7 transcription factor. Osteochondroprogenitor cells differentiate under the influence of growth factors, although isolated mesenchymal stem cells in tissue culture, form osteoblasts under permissive conditions that include vitamin C and substrates for alkaline phosphatase, a key enzyme that provides high concentrations of phosphate at the mineral deposition site.

Bone Formation

Key growth factors in endochondral skeletal differentiation include bone morphogenetic proteins (BMPs) that determine to a major extent where chondrocyte differentiation occurs and where spaces are left between bones. The system of cartilage replacement by bone has a complex regulatory system. BMP2 also regulates early skeletal patterning. Transforming growth factor beta (TGF-β) is part of a superfamily of proteins that include BMPs, which possess common signaling elements in the TGF beta signaling pathway. TGF-β is particularly important in cartilage differentiation, which generally precedes bone formation for endochondral ossification. An additional family of essential regulatory factors is the fibroblast growth factors (FGFs) that determine where skeletal elements occur in relation to the skin.

Many other regulatory systems are involved in the transition of cartilage to bone and in bone maintenance. A particularly important bone-targeted hormonal regulator is parathyroid hormone (PTH). Parathyroid hormone is a protein made by the parathyroid gland under the control of serum calcium activity. PTH also has important systemic functions, including to keep serum calcium concentrations nearly constant regardless of calcium intake. Increasing dietary calcium results in minor increases in blood calcium. However, this is not a significant mechanism supporting osteoblast bone formation, except in the condition of low dietary calcium; further, abnormally high dietary calcium raises the risk of serious health consequences not directly related to bone mass including heart attack and stroke. Intermittent PTH stimulation increases osteoblast activity, although PTH is bifunctional and mediates bone matrix degradation at higher concentrations.

The skeleton is also modified for reproduction and in response to nutritional and other hormone stresses; it responds to steroids, including estrogen and glucocorticoids, which are important in reproduction and energy metabolism regulation. Bone turnover involves major expenditures of energy for synthesis and degradation, involving many additional signals including pituitary hormones. Two of hormones include adrenocorticotropic hormone (ACTH) and follicle stimulating hormone. The physiological role for responses to these, and several other glycoprotein hormones, is not fully understood, although it is likely that ACTH is bifunctional, like PTH, supporting bone formation with periodic spikes of ACTH, but causing bone destruction in large concentrations. In mice, mutations that reduce the efficiency of ACTH-induced glucocorticoid production in the adrenals cause the skeleton to become dense (osteosclerotic bone).

Chondrocytes are the only cells found in healthy cartilage. They produce and maintain the cartilaginous matrix, which consists mainly of collagen and proteoglycans. Although the word chondroblast is commonly used to describe an immature chondrocyte, the term is imprecise, since the progenitor of chondrocytes, which are mesenchymal stem cells, can differentiate into various cell types, including osteoblasts.

Mesenchymal stem cells are undifferentiated, meaning they can differentiate into a variety of generative cells commonly known as osteochondrogenic (or osteogenic, chondrogenic, osteoprogenitor, etc.) cells. When referring to bone or cartilage, the originally undifferentiated mesenchymal stem cells lose their pluripotency, proliferate and crowd together in a dense aggregate of chondrogenic cells (cartilage) at the location of chondrification. These chondrogenic cells differentiate into so-called chondroblasts, which then synthesize the cartilage extracellular matrix (ECM), consisting of a ground substance (proteoglycans, glycosaminoglycans for low osmotic potential) and fibers. The chondroblast is now a mature chondrocyte that is usually inactive but can still secrete and degrade the matrix, depending on conditions.

BMP4 and FGF2 have been shown to increase chondrocyte differentiation. Chondrocytes undergo terminal differentiation when they become hypertrophic, which happens during endochondral ossification. This last stage is characterized by major phenotypic changes in the cell.

A myocyte is also known as a muscle cell and is the type of cell found in muscle tissue. Myocytes are long, tubular cells that develop from myoblasts to form muscles in a process known as myogenesis. There are various specialized forms of myocytes with distinct properties, including cardiac, skeletal, and smooth muscle cells. The striated cells of cardiac and skeletal muscles are referred to as muscle fibers. Cardiomyocytes are the muscle fibers that form the chambers of the heart and have a single central nucleus. Skeletal muscle fibers help support and move the body and tend to have peripheral nuclei. Smooth muscle cells control involuntary movements such as the peristalsis contractions in the esophagus and stomach.

A myoblast is a type of embryonic progenitor cell that differentiates into muscle cells. Differentiation is regulated by myogenic regulatory factors, including MyoD, Myf5, myogenin, and MRF4. GATA4 and GATA6 also play a role in myocyte differentiation. Skeletal muscle fibers are made when myoblasts fuse together; muscle fibers therefore are cells with multiple nuclei, known as myonuclei, with each cell nucleus originating from a single myoblast. The fusion of myoblasts is specific to skeletal muscle and not cardiac muscle or smooth muscle.

Myoblasts in skeletal muscle that do not form muscle fibers dedifferentiate back into myosatellite cells. These satellite cells remain adjacent to a skeletal muscle fiber, situated between the sarcolemma and the basement membrane of the endomysium, which is the connective tissue investment that divides the muscle fascicles into individual fibers. To re-activate myogenesis, the satellite cells must be stimulated to differentiate into new fibers.

In some embodiments, myoblasts and their derivatives, including satellite cells, may be generated in vitro through directed differentiation of pluripotent stem cells. Kindlin-2 plays a role in developmental elongation during myogenesis.

Muscle fibers grow when exercised and shrink when not in use. This is because exercise stimulates the increase in myofibrils which increase the overall size of muscle cells. Well-exercised muscles can not only add more size but can also develop more mitochondria, myoglobin, glycogen and a higher density of capillaries. However, muscle cells cannot divide to produce new cells, and as a result we have fewer muscle cells as an adult than as a newborn.

In some embodiments, controlling the rate of fatty acid oxidation in mesenchymal stem cells comprises inhibiting fatty acid oxidation.

In some embodiments, controlling the rate of fatty acid oxidation in mesenchymal stem cells comprises increasing the rate of fatty acid oxidation. In specific embodiments, increasing the rate of fatty acid oxidation promotes bone formation.

Type 2 Diabetes

In specific embodiments, inhibiting fatty acid oxidation prevents development of Type 2 Diabetes (T2D). Type 2 diabetes is a chronic condition that affects the way the body metabolizes sugar (glucose), which is an important source of fuel for the body. With T2D, the body either resists the effects of insulin or doesn't produce enough insulin to maintain normal glucose levels. Insulin is a hormone that comes from the pancreas, and it regulates the movement of sugar into cells. The pancreas secretes insulin into the bloodstream. The insulin circulates, enabling sugar to enter the cells. Insulin lowers the amount of sugar in the bloodstream. As the blood sugar level drops, so does the secretion of insulin from the pancreas.

Glucose is a main source of energy for the cells that make up muscles and other tissues. Glucose comes from two major sources: food and the liver. Sugar is absorbed into the bloodstream, where it enters cells with the help of insulin. The liver stores and makes glucose. When glucose levels are low, such as when a person hasn't eaten in a while, the liver breaks down stored glycogen into glucose to keep glucose levels within a normal range. In T2D this process is impaired and instead of moving into the cells, sugar builds up in the bloodstream. As blood sugar levels increase, the insulin-producing beta cells in the pancreas release more insulin, but eventually these cells become impaired and can't make enough insulin to meet the body's demands.

Methods for Treating Metabolic Disorders

In some embodiments, the invention provides a method of treating a metabolic disorder in a patient in need thereof comprising modulating the expression of ADCY5 in a cell.

As used in this context, to "treat" means to cure, ameliorate, stabilize, prevent, or reduce the severity of at least one symptom or a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "in need of treatment" as used herein refers to a judgment made by a caregiver (e.g. physician, nurse, nurse practitioner, or individual in the case of humans; veterinarian in the case of animals, including non-human animals) that a subject requires or will benefit from treatment. This judgment is made based on a variety of factors that are in the realm of a caregiver's experience, but that include the knowledge that the subject is ill, or will be ill, as the result of a condition that is treatable by the compositions and therapeutic agents described herein. In embodiments, the judgment by the caregiver has been made, and the subject identified as requiring or benefitting from treatment.

The administration of compositions, agents, cells, or populations of cells, as disclosed herein may be carried out in any convenient manner including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally.

A metabolic disorder can happen when abnormal chemical reactions in the body alter the normal metabolic process. Exemplary metabolic disorders that can be treated using the methods described herein include, but are not necessarily limited to, high bone mineral density and hyperglycemia.

Bone Mineral Density

Bone density, or bone mineral density (BMD), is the amount of bone mineral in bone tissue. When thinking of density in the physics sense, the concept is of mass of mineral per volume of bone. However, clinically BMD is measured by proxy according to optical density per square centimeter of bone surface upon imaging. Bone density measurements are used in clinical medicine as an indirect indicator of osteoporosis and fracture risk. BMD is measured by a procedure called densitometry, often performed in the radiology or nuclear medicine departments of hospitals or clinics. The measurement is painless and non-invasive and involves low radiation exposure. Measurements are most commonly made over the lumbar spine and over the upper part of the hip. The forearm may be scanned if the hip and lumbar spine are not accessible.

Hyperglycemia

Hyperglycemia is a defining characteristic of diabetes. It is a condition in which an excessive amount of glucose circulates in the blood plasma. This is generally a blood sugar level higher than 11.1 mmol/l (200 mg/dl), but symptoms may not start to become noticeable until even higher values such as 15-20 mmol/l (~250-300 mg/dl). A subject with a consistent range between ~5.6 and ~7 mmol/l (100-126 mg/dl) is considered slightly hyperglycemic, while someone with levels above 7 mmol/l (126 mg/dl) is generally held to have diabetes. For diabetics, glucose levels that are considered to be too hyperglycemic can vary from person to person, mainly due to the person's renal threshold of glucose and overall glucose tolerance. On average however, chronic levels above 10-12 mmol/L (180-216 mg/dl) can produce noticeable organ damage over time.

In untreated hyperglycemia, a condition called ketoacidosis may develop because decreased insulin levels increase the activity of hormone-sensitive lipase. The degradation of triacylglycerides by hormone-sensitive lipase produces free fatty acids that are eventually converted to acetyl-coA by beta-oxidation. Symptoms of ketoacidosis include shortness of breath, fruity breath, nausea and vomiting, and very dry mouth. Chronic hyperglycemia (high blood sugar) injures the heart in patients without a history of heart disease or diabetes and is strongly associated with heart attacks and death in subjects with no coronary heart disease or history of heart failure. Hence, ketoacidosis is a life-threatening condition which requires immediate treatment.

Chronic hyperglycemia that persists even in fasting states is most commonly caused by diabetes mellitus. In fact, chronic hyperglycemia is the defining characteristic of the disease. Intermittent hyperglycemia may be present in prediabetic states. Acute episodes of hyperglycemia without an obvious cause may indicate developing diabetes or a predisposition to the disorder. In diabetes mellitus, hyperglycemia is usually caused by low insulin levels (T1D) and/or by resistance to insulin at the cellular level (T2D), depending on the type and state of the disease. Low insulin levels and/or insulin resistance prevent the body from converting glucose into glycogen (a starch-like source of energy stored mostly in the liver), which in turn makes it difficult or impossible to remove excess glucose from the blood. With normal glucose levels, the total amount of glucose in the blood at any given moment is only enough to provide energy to the body for 20-30 minutes, and so glucose levels must be precisely maintained by the body's internal control mechanisms. Failure in these mechanisms that allow glucose to rise to abnormal levels result in hyperglycemia.

Other metabolic disorders within the scope of the present invention include, but are not necessarily limited to, acid-base imbalance, metabolic brain diseases, disorders of calcium metabolism, DNA repair-deficiency disorders, hyper lactatemia, iron metabolism disorders, lipid metabolism disorders, malabsorption syndromes, metabolic syndrome X, inborn error of metabolism, mitochondrial diseases, phosphorus metabolism disorders, porphyrias, proteostasis deficiencies, metabolic skin diseases, wasting syndrome, and water-electrolyte imbalance.

In specific embodiments, the metabolic disorder to be treated by modulating the expression of ADCY5 in a cell may be Type 2 Diabetes (T2D).

In some embodiments, the cell within which the expression of ADCY5 is modified may be an adipocyte, as described elsewhere herein. In some embodiments, modulating the expression or activity of ADCY5 may comprise increasing the expression or activity of ADCY5.

In some embodiments, the cell within which the expression of ADCY5 is modified may be an osteoblast, as described elsewhere herein. In some embodiments, modulating the expression or activity of ADCY5 may comprise decreasing the expression or activity of ADCY5.

In some embodiments, the invention provides a method of treating a metabolic disorder in a patient in need thereof comprising determining the patient's haplotype at the 3q21.1 locus, as described in the examples. Accordingly, one may administer a therapeutically effective amount of an agent capable of modulating the expression or activity of ADCY5 if the patient is homozygous for a haplotype characteristic of high bone mineral density and increased hyperglycemia, as described elsewhere herein.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

For example, in methods for treating metabolic disorders in a subject, an effective amount of a combination of inhibitors targeting epigenetic genes is any amount that provides an effect that combats metabolic disorders, such as reduces or prevents expression or activity of ADCY5 in a cell or increases the expression or activity of ADCY5 in a cell. In certain embodiments, the effective amount of an inhibitor targeting an epigenetic gene is reduced when an inhibitor is administered concomitantly or in combination with one or more additional inhibitors targeting epigenetic genes as compared to the effective amount of the inhibitor when administered in the absence of one or more additional inhibitors targeting epigenetic genes. In certain embodiments, the inhibitor targeting an epigenetic gene does not modulate the expression or activity of ADCY5 in a cell when administered in the absence of one or more additional inhibitors targeting epigenetic genes.

Methods for Regulating Fasting Glucose Levels

In some embodiments, the invention provides a method of regulating fasting glucose levels in a subject in need thereof by modulating the expression or activity of ADCY5 in adipocytes.

Normal blood glucose value ranges may vary slightly among different laboratories. Many factors affect a person's blood sugar level. The body's homeostatic mechanism of blood sugar regulation (known as glucose homeostasis), when operating normally, restores the blood sugar level to a narrow range of about 4.4 to 6.1 mmol/L (79 to 110 mg/dL) (as measured by a fasting blood glucose test).

The normal blood glucose level is tested while fasting, and for non-diabetics it should be between 3.9 and 7.1 mmol/L (70 to 130 mg/dL). The global mean fasting plasma blood glucose level in humans is about 5.5 mmol/L (100 mg/dL). However, this level fluctuates throughout the day. Blood sugar levels for those without diabetes and who are not fasting should be below 6.9 mmol/L (125 mg/dL). The blood glucose target range for diabetics, according to the American Diabetes Association, should be 5.0-7.2 mmol/l (90-130 mg/dL) before meals, and less than 10 mmol/L (180 mg/dL) after meals, as measured by a blood glucose monitor.

Despite widely variable intervals between meals or the occasional consumption of meals with a substantial carbohydrate load, human blood glucose levels tend to remain within the normal range. However, shortly after eating, the blood glucose level may rise, in non-diabetics, temporarily up to 7.8 mmol/L (140 mg/dL) or slightly more. For people with diabetes maintaining 'tight diabetes control', the American Diabetes Association recommends a post-meal glucose level of less than 10 mmol/L (180 mg/dL) and a fasting plasma glucose of 3.9 to 7.2 mmol/L (70-130 mg/dL).

The actual amount of glucose in the blood and body fluids is very small. In a healthy adult male of 75 kg with a blood volume of 5 liters, a blood glucose level of 5.5 mmol/L (100 mg/dL) amounts to 5 g, equivalent to about a teaspoonful of sugar. Part of the reason why this amount is so small is that, to maintain an influx of glucose into cells, enzymes modify glucose by adding phosphate or other groups to it.

The body's homeostatic mechanism keeps blood glucose levels within a narrow range. This mechanism is composed of several interacting systems, of which hormone regulation is the most important.

There are two types of mutually antagonistic metabolic hormones affecting blood glucose levels, these include catabolic hormones (such as glucagon, cortisol and catecholamines) which increase blood glucose; and one anabolic hormone (insulin), which decreases blood glucose. These hormones are secreted from pancreatic islets which are bundles of endocrine tissues. There are four types of pancreatic islets: alpha (A) cells, beta (B) cells, Delta (D) cells, and F cells. Glucagon is secreted from alpha cells, while insulin is secreted by beta cells. Together they regulate the blood-glucose levels through negative feedback, a process where the end product of one reaction stimulates the beginning of another reaction. In blood-glucose levels, insulin lowers the concentration of glucose in the blood. The lower blood-glucose level (a product of the insulin secretion) triggers glucagon to be secreted, and repeats the cycle.

In order for blood glucose to be kept stable, modifications to insulin, glucagon, epinephrine and cortisol are made. Each of these hormones has a different responsibility to keep blood glucose regulated; when blood sugar is too high, insulin tells muscles to take up excess glucose for storage.

Glucagon responds to too low of a blood glucose level; it informs the tissue to produce more glucose. Epinephrine prepares the muscles and respiratory system for activity in the case of a "fight and flight" response. Lastly, cortisol supplies the body with fuel in times of heavy stress.

If blood sugar levels remain too high, the body will suppress appetite over the short term. Long-term hyperglycemia causes many health problems including heart disease, cancer, eye, kidney, and nerve damage. Blood sugar levels above 300 mg/dL can cause fatal reactions. Ketones will be very high (a magnitude higher than when eating a very low carbohydrate diet) initiating ketoacidosis. The Mayo Clinic recommends emergency room treatment above 300 mg/dL blood glucose.

The most common cause of hyperglycemia is diabetes. When diabetes is the cause, physicians typically recommend an anti-diabetic medication as treatment. Presently, from the perspective of the majority of patients, treatment with an old, well-understood diabetes drug such as metformin will be the safest, most effective, least expensive, most comfortable route to managing the condition. Diet changes and exercise implementation may also be part of a treatment plan for diabetes.

In some embodiments, modulating the expression or activity of ADCY5 in adipocytes may comprise decreasing fasting glucose levels by decreasing the expression or activity of ADCY5 in adipocytes, as described elsewhere herein.

In some embodiments, modulating the expression or activity of ADCY5 in adipocytes may comprise increasing fasting glucose levels by increasing the expression or activity of ADCY5 in adipocytes, as described elsewhere herein.

Methods for Regulating Bone Growth

In some embodiments, the invention provides a method of regulating bone growth rates in a subject in need thereof by modulating the expression or activity of ADCY5 in osteoblasts.

Mechanisms of bone growth are described elsewhere herein. Briefly, bone is a dynamic tissue that is constantly being reshaped by osteoblasts, which produce and secrete matrix proteins and transport mineral into the matrix, and osteoclasts, which break down the tissues. Osteoblasts are the major cellular component of bone and they arise from mesenchymal stem cells (MSC). MSC give rise to osteoblasts, adipocytes, and myocytes among other cell types. Osteoblast quantity is understood to be inversely proportional to that of marrow adipocytes which comprise marrow adipose tissue (MAT). Osteoblasts are found in large numbers in the periosteum, the thin connective tissue layer on the outside surface of bones, and in the endosteum. Normally, almost all of the bone matrix is mineralized by the osteoblasts. Before the organic matrix is mineralized, it is called the osteoid. Osteoblasts buried in the matrix are called osteocytes. During bone formation, the surface layer of osteoblasts consists of cuboidal cells, called active osteoblasts. When the bone-forming unit is not actively synthesizing bone, the surface osteoblasts are flattened and are called inactive osteoblasts. Osteocytes remain alive and are connected by cell processes to a surface layer of osteoblasts. Osteocytes have important functions in skeletal maintenance.

In some embodiments, modulating the expression or activity of ADCY5 in osteoblasts comprises promoting bone growth by increasing the expression or activity of ADCY5 in osteoblasts, as described elsewhere herein.

In some embodiments, modulating the expression or activity of ADCY5 in osteoblasts comprises inhibiting or reducing a rate of bone growth by decreasing the expression or activity of ADCY5 in osteoblasts, as described elsewhere herein.

Modulating Agents

In some embodiments, reducing or inhibiting the activity of ADCY5 is achieved using a modulating agent such as a therapeutic antibody, antibody fragment, antibody-like protein scaffold, aptamer, polypeptide, protein, genetic modifying agent, CRISPR system or small molecule, small molecule degrader, or a combination thereof.

In some embodiments, modulating may comprise administering one or more modulating agents that modulate the expression or activity of ADCY5, as described elsewhere herein.

Antibodies

In certain embodiments, the modulating agent is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, VHH and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, 1 gM antibodies exist in pentameric form, and IgA antibodies exist in monomeric, dimeric or multimeric form.

The term "IgG subclass" refers to the four subclasses of immunoglobulin class IgG—IgG1, IgG2, IgG3, and IgG4 that have been identified in humans and higher mammals by the heavy chains of the immunoglobulins, V1-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins—harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 μM. Antibodies with affinities greater than $1 \times 10^7$ $M^{-1}$ (or a dissociation coefficient of 1 μM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., International Patent Publication No. WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4):1786-1794 (1998); Zhu et al., Cancer Res. 58(15):3209-3214 (1998); Yoon et al., J. Immunol. 160(7):

3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4):755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody, such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Aptamers

In certain embodiments, the modulating agent is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-NH$_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, 0-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Small Molecule

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule. Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810).

As described herein, small molecules targeting epigenetic proteins are currently being developed and/or used in the clinic to treat disease (see, e.g., Qi et al., HEDD: the human epigenetic drug database. Database, 2016, 1-10; and Ackloo et al., Chemical probes targeting epigenetic proteins: Applications beyond oncology. Epigenetics 2017, VOL. 12, NO. 5, 378-400). In certain embodiments, the one or more agents comprise a histone acetylation inhibitor, histone deacetylase (HDAC) inhibitor, histone lysine methylation inhibitor, histone lysine demethylation inhibitor, DNA methyltransferase (DNMT) inhibitor, inhibitor of acetylated histone binding proteins, inhibitor of methylated histone binding proteins, sirtuin inhibitor, protein arginine methyltransferase inhibitor or kinase inhibitor. In certain embodiments, any small molecule exhibiting the functional activity described above may be used in the present invention. In certain embodiments, the DNA methyltransferase (DNMT) inhibitor is selected from the group consisting of azacitidine (5-azacytidine), decitabine (5-aza-2'-deoxycytidine), EGCG (epigallocatechin-3-gallate), zebularine, hydralazine, and procainamide. In certain embodiments, the histone acetylation inhibitor is C646. In certain embodiments, the histone deacetylase (HDAC) inhibitor is selected from the group consisting of vorinostat, givinostat, panobinostat, belinostat, entinostat, CG-1521, romidepsin, ITF-A, ITF-B, valproic acid, OSU-HDAC-44, HC-toxin, magnesium valproate, plitidepsin, tasquinimod, sodium butyrate, mocetinostat, carbamazepine, SB939, CHR-2845, CHR-3996, JNJ-26481585, sodium phenylbutyrate, pivanex, abexinostat, resminostat, dacinostat, droxinostat, and trichostatin A (TSA). In certain embodiments, the histone lysine demethylation inhibitor is selected from the group consisting of pargyline, clorgyline, bizine, GSK2879552, GSK-J4, KDM5-C70, JIB-04, and tranylcypromine. In certain embodiments, the histone lysine methylation inhibitor is selected from the group consisting of EPZ-6438, GSK126, CPI-360, CPI-1205, CPI-0209, DZNep, GSK343, EI1, BIX-01294, UNC0638, EPZ004777, GSK343, UNC1999 and UNC0224. In certain embodiments, the inhibitor of acetylated histone binding proteins is selected from the group consisting of AZD5153 (see e.g., Rhyasen et al., AZD5153: A Novel Bivalent BET Bromodomain Inhibitor Highly Active against Hematologic Malignancies, Mol Cancer Ther. 2016 November; 15(11):2563-2574. Epub 2016 Aug. 29), PFI-1, CPI-203, CPI-0610, RVX-208, OTX015, I-BET151, I-BET762, I-BET-726, dBET1, ARV-771, ARV-825, BETd-260/ZBC260 and MZ1. In certain embodiments, the inhibitor of methylated histone binding proteins is selected from the group consisting of UNC669 and UNC1215. In certain embodiments, the sirtuin inhibitor comprises nicotinamide.

In specific embodiments, the small molecule is etomoxir.

In some embodiments, modulating may comprise introducing a mutation or base edit that modulates ADCY5 expression.

In some embodiments, the mutation or base edit is introduced using a CRISPR-Cas system, RNAi system, a TALEN, a Zn-finger nuclease, or a meganuclease.

RNAi

In certain embodiments, the genetic modifying agent is RNAi (e.g., shRNA). As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microR-NAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

CRISPR Systems

In general, a CRISPR-Cas or CRISPR system as used in herein and in documents, such as International Patent Publication No. WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in International Patent Publication No. WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to International Patent Publication No. WO 2014/093622 (PCT/US13/74667), incorporated herein by reference. Methods of US Patent Publication Nos. 20120017290 and 20110265198 assigned to Sangamo BioSciences, Inc., directed to targeting the Rosa locus, may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell.

Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects, the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is, operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are incorporated herein by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector is to express an array of promoter-RNAs separated by cleavable sequences in the intron of a coding sequence or gene; and, in this instance, it is advantageous to use a polymerase II promoter, which can have increased expression and enable the transcription of long RNA in a tissue specific manner. (see, e.g., nar.oxford-journals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters, especially as to the numbers of RNAs or guides discussed herein, without any undue experimentation.

The guide RNA(s) encoding sequences and/or Cas encoding sequences can be functionally or operatively linked to regulatory element(s), and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39 40, 41, 42, 43, 44, 45, 46, 47 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15 to 30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl(cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS, E*7110-E7111; Allerson et al., *J. Med. Chem.* 2005, 48:901-904; Bramsen et al., *Front. Genet.,* 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33(9): 985-989; Li et al., *Nature Biomedical Engineering,* 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl(cEt), or 2'-O-methyl 3' thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS, E*7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methyl-guanosine, 2'-O-methyl 3'phosphorothioate (MS), S-constrained ethyl(cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment, the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop, will form a complete hairpin in the overall secondary structure, and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments, the natural hairpin or stem-loop structure of the guide molecule is extended or replaced by an extended stemloop. It has been demonstrated that extension of the stem can enhance the assembly of the guide molecule with the CRISPR-Cas protein (Chen et al. Cell.

(2013); 155(7): 1479-1491). In particular embodiments, the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the complementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below, and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi: 10.1038/nature14592. As further detailed herein, the skilled person will understand that Cas13 proteins may be modified analogously.

In particular embodiments, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends a guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm$^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans;4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see International Patent Publication No. WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc., as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100 .mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably, the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms.

Preferably, the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between IV/cm and 20V/cm, for a period of 100 milliseconds or more, preferably 15 minutes or more.

Ultrasound is advantageously administered at a power level of from about 0.05 W/cm2 to about 100 W/cm2. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm2 (FDA recommendation), although energy densities of up to 750 mW/cm2 have been used. In physiotherapy, ultrasound is typically used as an energy source in a range up to about 3 to 4 W/cm2 (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142. Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2.

Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see International Patent Publication No. WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably, the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a "protector RNA" to a sequence of the guide molecule, wherein the "protector RNA" is an RNA strand complementary to the 3' end of the guide molecule to thereby generate a partially double-stranded guide RNA. In an embodiment of the invention, protecting mismatched bases (i.e., the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This "protector sequence" ensures that the guide molecule comprises a "protected sequence" in addition to an "exposed sequence" (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g., Cox et al., Science. 2017 Nov.

24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of a Cas effector module and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

Within the context of base editing, reference is made to the following publications, all of which are incorporated by reference herein, in their entirety: Precision Chemistry on the Genome and Transcriptome of Living Cells, Rees et al. Nat. Rev. Genet. 19:770-788. (2018); Targeting Fidelity of Adenine and Cytosine Base Editors in Mouse Embryos, Lee et al. Nat. Commun. 9:4804. 1-5 (2018); Adenine Base Editing in an Adult Mouse Model of Tyrosinemia, Song et al. Biomed. Eng. 36:536-539 (2018); Simultaneous Targeting of Linked Loci in Mouse Embryos Using Base Editing, Lee et al. Sci. Rep. 9:1662 (2019); Continuous evolution of base editors with expanded target compatibility and improved activity, Thuronyi et al. Nat. Biotechnol. 37:1070-1079 (2019); Search-and-replace genome editing without double-strand breaks or donor DNA, Anzalone et al. Nature, 576:149-157 (2019); Phage-Assisted Evolution of an Adenine Base Editor with Enhanced Cas Domain Compatibility and Activity Richter, Zhao et al. Nat. Biotechnol. in press (2020). Reference is also made to Abudayyeh et al., Science 365(6451):382-386; and International Patent Publication Nos. WO 2019/005884, WO 2019/005886, WO 2020/028555, WO 2019/060746, WO 2019/071048, and WO 2019/084063; each of which is incorporated by reference herein.

The present invention may also use a Cas12 CRISPR enzyme. Cas12 enzymes include Cas12a (Cpf1), Cas12b (C2c1), and Cas12c (C2c3), described further herein.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse);

In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015);

Shalem et al., "High-throughput functional genomics using CRISPR-Cas9," Nature Reviews Genetics 16, 299-311 (May 2015);

Xu et al., "Sequence determinants of improved CRISPR sgRNA design," Genome Research 25, 1147-1157 (August 2015);

Parnas et al., "A Genome-wide CRISPR Screen in Primary Immune Cells to Dissect Regulatory Networks," Cell 162, 675-686 (Jul. 30, 2015);

Ramanan et al., CRISPR-Cas9 cleavage of viral DNA efficiently suppresses hepatitis B virus," Scientific Reports 5:10833. doi: 10.1038/srep10833 (Jun. 2, 2015);

Nishimasu et al., Crystal Structure of Staphylococcus aureus Cas9," Cell 162, 1113-1126 (Aug. 27, 2015);

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16;

Cpf1 Is a Single RNA-Guided Endonuclease of a Class 2 CRISPR-Cas System, Zetsche et al., Cell 163, 759-71 (Sep. 25, 2015);

Discovery and Functional Characterization of Diverse Class 2 CRISPR-Cas Systems, Shmakov et al., Molecular Cell, 60(3), 385-397 doi: 10.1016/j.molcel.2015.10.008 Epub Oct. 22, 2015;

Rationally engineered Cas9 nucleases with improved specificity, Slaymaker et al., Science 2016 Jan. 1 351(6268): 84-88 doi: 10.1126/science.aad5227. Epub 2015 Dec. 1;

Gao et al, "Engineered Cpf1 Enzymes with Altered PAM Specificities," bioRxiv 091611; doi: http://dx.doi.org/10.1101/091611 (Dec. 4, 2016);

Cox et al., "RNA editing with CRISPR-Cas13," Science. 2017 Nov. 24; 358(6366):1019-1027. doi: 10.1126/science.aaq0180. Epub 2017 Oct. 25;

Gaudelli et al. "Programmable base editing of A-T to G-C in genomic DNA without DNA cleavage" Nature 464(551); 464-471 (2017); and Strecker et al., "Engineering of CRISPR-Cas12b for human genome editing," Nature Communications volume 10, Article number: 212 (2019).

each of which is incorporated herein by reference, may be considered in the practice of the instant invention, and discussed briefly below:

Cong et al. engineered type II CRISPR-Cas systems for use in eukaryotic cells based on both Streptococcus thermophilus Cas9 and also Streptococcus pyogenes Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described anew way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayyeh et al. 2016, Science, 5; 353 (6299)). In particular embodiments, such methods for identifying novel CRISPR effector proteins may comprise the steps of selecting sequences from the database encoding a seed which identifies the presence of a CRISPR Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

Also, Harrington et al. "Programmed DNA destruction by miniature CRISPR-Cas14 enzymes" Science 2018 doi:10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publication Nos. US 2014-0310830 A1 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-027323 A1 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 A1 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 A1 (U.S. application Ser. No. 14/183,429); US 2015-0184139 A1 (U.S. application Ser. No. 14/324,960); U.S. application Ser. No. 14/054,414; European Patent Applications EP 2771468 (EP13818570.7), EP 2764103

(EP13824232.6), and EP 2784162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. Provisional Application No. 62/180,709, filed 17 Jun. 2015, PROTECTED GUIDE RNAS (PGRNAS); U.S. Provisional Application No. 62/091,455, filed 12 Dec. 2014, PROTECTED GUIDE RNAS (PGRNAS); U.S. Provisional Application No. 62/096,708, filed 24 Dec. 2014, PROTECTED GUIDE RNAS (PGRNAS); US Provisional Application Nos. 62/091,462, filed 12 Dec. 2014, 62/096,324, filed 23 Dec. 2014, 62/180,681, filed 17 Jun. 2015, and 62/237,496, filed 5 Oct. 2015, DEAD GUIDES FOR CRISPR TRANSCRIPTION FACTORS; U.S. Provisional Application Nos. 62/091,456, filed 12 Dec. 2014 and 62/180,692, filed 17 Jun. 2015, ESCORTED AND FUNCTIONALIZED GUIDES FOR CRISPR-CAS SYSTEMS; U.S. Provisional Application No. 62/091,461, filed 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. Provisional Application No. 62/094,903, filed 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. Provisional Application No. 62/096,761, filed 24 Dec. 2014, ENGINEERING OF SYSTEMS, METHODS AND OPTIMIZED ENZYME AND GUIDE SCAFFOLDS FOR SEQUENCE MANIPULATION; U.S. Provisional Application No. 62/098,059, filed 30 Dec. 2014, 62/181,641, filed 18 Jun. 2015, and 62/181,667, filed 18 Jun. 2015, RNA-TARGETING SYSTEM; US Provisional Application Nos. 62/096,656, filed 24 Dec. 2014 and 62/181,151, filed 17 Jun. 2015, CRISPR HAVING OR ASSOCIATED WITH DESTABILIZATION DOMAINS; U.S. Provisional Application No. 62/096,697, filed 24 Dec. 2014, CRISPR HAVING OR ASSOCIATED WITH AAV; U.S. Provisional Application No. 62/098,158, filed 30 Dec. 2014, ENGINEERED CRISPR COMPLEX INSERTIONAL TARGET- ING SYSTEMS; U.S. Provisional Application No. 62/151,052, filed 22 Apr. 2015, CELLULAR TARGETING FOR EXTRACELLULAR EXOSOMAL REPORTING; U.S. Provisional Application No. 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. Provisional Application No. 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No. 62/055,484, filed 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No. 62/087,537, filed 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. Provisional Application No. 62/054,651, filed 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. Provisional Application No. 62/067,886, filed 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US Provisional Application Nos. 62/054,675, filed 24 Sep. 2014 and 62/181,002, filed 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. Provisional Application No. 62/054,528, filed 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. Provisional Application No. 62/055,454, filed 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. Provisional Application No. 62/055,460, filed 25 Sep. 1014, MULTI-FUNCTIONAL-CRISPR COMPLEXES AND/OR OPTIMIZED ENZYME LINKED FUNCTIONAL-CRISPR COMPLEXES; US Provisional Application Nos. 62/087,475, filed 4 Dec. 2014 and 62/181,690, filed 18 Jun. 2015, FUNCTIONAL SCREENING WITH OPTIMIZED FUNCTIONAL CRISPR-CAS SYSTEMS; U.S. Provisional Application No. 62/055,487, filed 25 Sep. 2014, FUNCTIONAL SCREENING WITH OPTIMIZED FUNCTIONAL CRISPR-CAS SYSTEMS; US Provisional Application Nos. 62/087,546, filed 4 Dec. 2014 and 62/181,687, filed 18 Jun. 2015, MULTIFUNCTIONAL CRISPR COMPLEXES AND/OR OPTIMIZED ENZYME LINKED FUNCTIONAL-CRISPR COMPLEXES; and U.S. Provisional Application No. 62/098,285, filed 30 Dec. 2014, CRISPR MEDIATED IN VIVO MODELING AND GENETIC SCREENING OF TUMOR GROWTH AND METASTASIS.

Mention is made of US Provisional Application Nos. 62/181,659, filed 18 Jun. 2015 and 62/207,318, filed 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of US Provisional Application Nos. 62/181,663, filed 18 Jun. 2015 and 62/245,264, filed 22 Oct. 2015, NOVEL CRISPR ENZYMES AND SYSTEMS, US Provisional Application Nos. 62/181,675, filed 18 Jun. 2015, 62/285,349, filed 22 Oct. 2015, 62/296,522, filed 17 Feb. 2016, and 62/320,231, filed 8 Apr. 2016, NOVEL CRISPR ENZYMES AND SYSTEMS, U.S. Provisional Application No. 62/232,067, filed 24 Sep. 2015, U.S. Provisional application Ser. No. 14/975,085, filed 18 Dec. 2015, European application No. 16150428.7, U.S. Provisional Application No. 62/205,733, filed 16 Aug. 2015, U.S. Provisional Application No. 62/201,542, filed 5 Aug. 2015, U.S. Provisional Application No. 62/193,507, filed 16 Jul. 2015, and US Provisional Application Nos. 62/181,739, filed 18 Jun. 2015, each entitled NOVEL CRISPR ENZYMES AND SYSTEMS and of U.S. Provisional Application No. 62/245,270, filed 22 Oct. 2015, NOVEL CRISPR ENZYMES AND SYSTEMS. Mention is also made of U.S. Provisional Application No. 61/939,256, filed 12 Feb. 2014, and International Patent Publication No. WO 2015/089473 (PCT/US2014/070152), filed 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, filed 15 Aug. 2015, U.S. Provisional Application No. 62/180,699, filed 17 Jun. 2015, and U.S. Provisional Application No. 62/038,358, filed 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in International Patent Publication No. WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

TALE Systems

As disclosed herein editing can be made by way of the transcription activator-like effector nucleases (TALENs) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

In advantageous embodiments of the invention, the methods provided herein use isolated, non-naturally occurring, recombinant or engineered DNA binding proteins that comprise TALE monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$—$(X_{12}X_{13})$—$X1_{4-33}$ or $_{34}$ or $_{35}$, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$—$(X_{12}X_{13})$—$X1_{4-33}$ or $_{34}$ or $_{35})z$, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated herein by reference in its entirety.

The TALE polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, polypeptide monomers having RVDs of H*, HA, KA, N*, NA, NC, NS, RA, and S* bind to adenine, guanine, cytosine and thymine with comparable affinity.

Figure 8B:
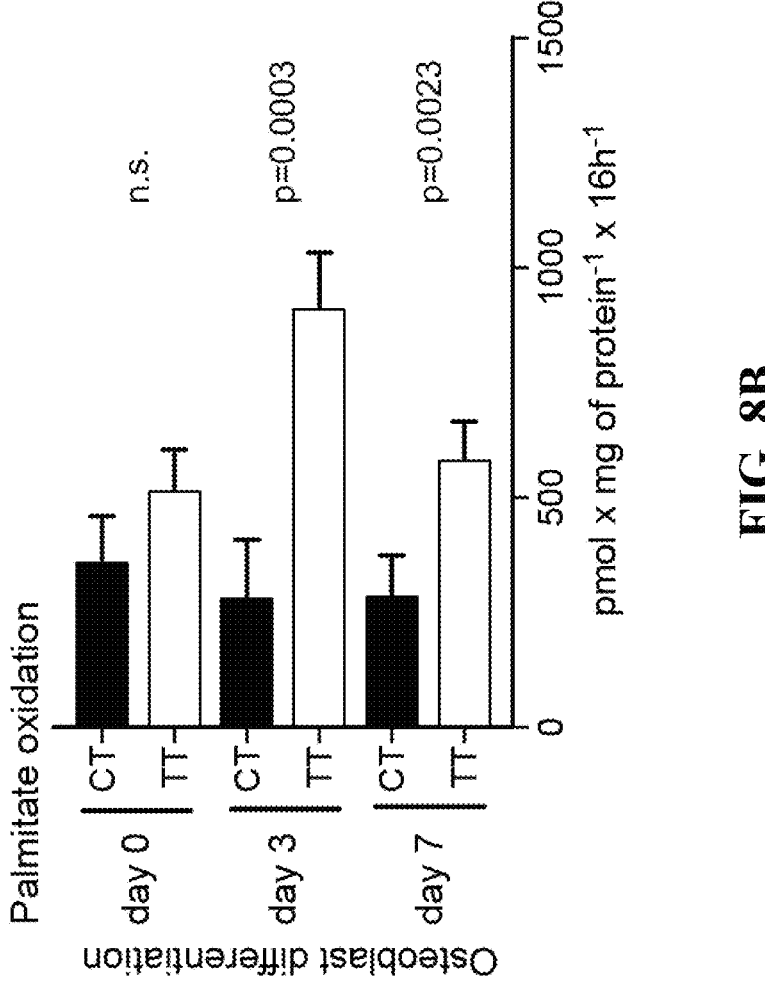
FIG. 8A-8E—(8A) Catecholamine-stimulated glycerol release in differentiated adipocytes at day 14 from 23 homozygotes for haplotype 1 and 18 heterozygotes (isoproterenol 1 μmol/l, 12 hours). (8B) Oxidation of [14C]palmitate (0.5 mM) to 14CO2 at different stages of osteoblasts differentiation (day 0, day 3, and day 7 of differentiation) in n=4 heterozygotes and n=4 homozygotes for haplotype 1. The results are normalized to protein concentration. (8C) Switch-like gene expression of marker genes involved in fatty acid transport and lipid oxidation in differentiating murine bone marrow stromal cells (BMSCs). Primary BMSCs cultured for 0, 1, 2, 3, or 7 days in osteogenic medium. Relative gene expression of fatty acid transport proteins (Cd36, Fatp1, Fatp3); extracellular lipases (Lpl, Lipc); and cytoplasmic lipases (Pnpla2/Atgl, Lipe/Hsl, Mgl). (8D) Catecholamine-stimulated glycerol release upon doxycycline-induced overexpression of ADCY5 in adipocytes specifically in heterozygous (n=18) vs. homozygous haplotype 1 (n=23) carriers. (8E) Relative expression of RUNX2, a marker gene of osteoblast differentiation, upon siRNA knock-down of ADCY5 (56% knock-down efficiency). Gene expression was measured by qPCR normalized to HPRT mRNA.
Figure 8A:
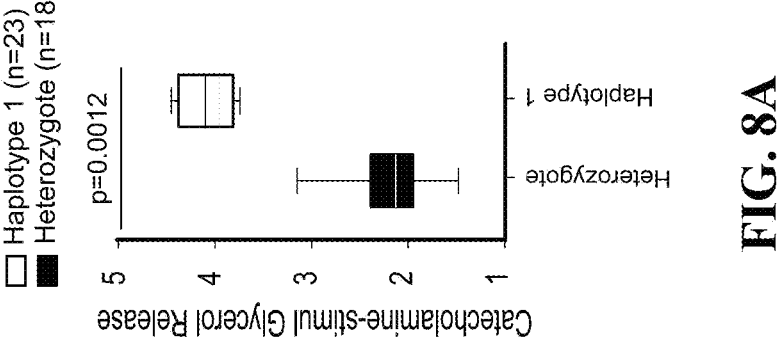

The predetermined N-terminal to C-terminal order of the one or more polypeptide monomers of the nucleic acid or DNA binding domain determines the corresponding predetermined target nucleic acid sequence to which the TALE polypeptides will bind. As used herein the polypeptide monomers and at least one or more half polypeptide monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and TALE polypeptides may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8), which is included in the term "TALE monomer". Therefore, it follows that the length of the nucleic acid or DNA being targeted is equal to the number of full polypeptide monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region. An exemplary amino acid sequence of a N-terminal capping region is:

```
                                  (SEQ ID NO: 1)
       M D P I R S R T P S P A R E L

L S G P Q P D G V Q P T A D R

G V S P P A G G P L D G L P A

R R T M S R T R L P S P P A P

S P A F S A D S F S D L L R Q

F D P S L F N T S L F D S L P

P F G A H H T E A A T G E W D

E V Q S G L R A A D A P P P T

M R V A V T A A R P P R A K P

A P R R R A A Q P S D A S P A

A Q V D L R T L G Y S Q Q Q Q

E K I K P K V R S T V A Q H H

E A L V G H G F T H A H I V A

L S Q H P A A L G T V A V K Y

Q D M I A A L P E A T H E A I

V G V G K Q W S G A R A L E A

L L T V A G E L R G P P L Q L

D T G Q L L K I A K R G G V T

A V E A V H A W R N A L T G A

P L N
```

An exemplary amino acid sequence of a C-terminal capping region is:

```
                                  (SEQ ID NO: 2)
       R P A L E S I V A Q L S R P D

P A L A A L T N D H L V A L A

C L G G R P A L D A V K K G L

P H A P A L I K R T N R R I P

E R T S H R V A D H A Q V V R

V L G F F Q C H S H P A Q A F

D D A M T Q F G M S R H G L L

Q L F R R V G V T E L E A R S

G T L P P A S Q R W D R I L Q

A S G M K R A K P S P T S T Q

T P D Q A S L H A F A D S L E

R D L D A P S P M H E G D Q T

R A S
```

As used herein the predetermined "N-terminus" to "C terminus" orientation of the N-terminal capping region, the DNA binding domain comprising the repeat TALE mono- mers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, frag- ments of the N-terminal and/or C-terminal capping regions are included in the TALE polypeptides described herein.

In certain embodiments, the TALE polypeptides described herein contain a N-terminal capping region frag- ment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodi- ments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences pro- vided herein. Sequence identity is related to sequence homology. Homology comparisons may be conducted by eye, or more usually, with the aid of readily available sequence comparison programs. These commercially avail- able computer programs may calculate percent (%) homol- ogy between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences pro- vided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Zn-Finger Nucleases

Other preferred tools for genome editing for use in the context of this invention include zinc finger systems. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

Meganucleases

As disclosed herein, editing can be made by way of meganucleases, which are endodeoxyribonucleases characterized by a large recognition site (double-stranded DNA sequences of 12 to 40 base pairs). Exemplary method for using meganucleases can be found in U.S. Pat. Nos. 8,163, 514; 8,133,697; 8,021,867; 8,119,361; 8,119,381; 8,124, 369; and 8,129,134, which are specifically incorporated by reference.

In some embodiments, the base edit may be made to genomic DNA or expressed RNA using a CRISPR-Cas system, as described herein.

In some embodiments, the mutation or base edit changes a C to T at rs5637196 to increase ADCY5 expression or changes a T to C at rs5637196 to decrease ADCY5 expression, as described in the examples.

In some embodiments, modulating may be done either in vivo or ex vivo.

Methods of Producing a Population of Cells

In some embodiments, the invention provides a method of producing a population of cells comprising an engineered mutation in the SNP variant rs56371916. The mutation may be engineered using any of the methods described in detail elsewhere herein.

For example, the mutation may be engineered using genome editing methods or by use of a CRISPR-Cas system, an inactivated CRISPR-Cas system, a Cas protein, a zinc finger protein (ZFP), a zinc finger nuclease (ZFN), a transcription activator-like effector (TALE), a transcription activator-like effector nuclease (TALEN), or a meganuclease, as described elsewhere herein.

In some embodiments, the engineered mutation may effect a reduction or inhibition of the expression or activity of ADCY5.

In some embodiments, the mutation comprises a T to C single nucleotide substitution.

In some embodiments, the engineered mutation increases the expression or activity of ADCY5.

In some embodiments, the invention provides a population of cells produced using the method described above.

In some embodiments, the engineered mutation may lead to increased fatty acid metabolism.

In some embodiments, the engineered mutation may lead to decreased fatty acid metabolism.

Kits

As described elsewhere herein and in the examples, the invention provides a method of treating a metabolic disorder in a patient in need thereof comprising determining the patient's haplotype at the 3q21.1 locus and administering a therapeutically effective amount of an agent capable of modulating the expression or activity of ADCY5 if the patient is homozygous for a haplotype characteristic of high bone mineral density and increased hyperglycemia.

In some embodiments, the invention provides a kit comprising reagents to determine the haplotype according to the method described above.

The kit may comprise primers and/or probes for quantitative RT-PCR or fluorescently bar-coded oligonucleotide probes for hybridization to RNA.

The term "barcode" as used herein refers to a short sequence of nucleotides (for example, DNA or RNA) that is used as an identifier for an associated molecule, such as a target molecule and/or target nucleic acid, or as an identifier of the source of an associated molecule, such as a cell-of-origin. A barcode may also refer to any unique, non-naturally occurring, nucleic acid sequence that may be used to identify the originating source of a nucleic acid fragment. Although it is not necessary to understand the mechanism of an invention, it is believed that the barcode sequence provides a high-quality individual read of a barcode associated with a single cell, a viral vector, labeling ligand (e.g., an aptamer), protein, shRNA, sgRNA or cDNA such that multiple species can be sequenced together.

Barcoding may be performed based on any of the compositions or methods disclosed in patent publication International Patent Publication No. WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

In some embodiments, the origin-specific barcodes are reversibly coupled to a solid or semisolid substrate. In some embodiments, the origin-specific barcodes further comprise a nucleic acid capture sequence that specifically binds to the target nucleic acids and/or a specific binding agent that specifically binds to the target molecules. In specific embodiments, the origin-specific barcodes include two or more populations of origin-specific barcodes, wherein a first population comprises the nucleic acid capture sequence and a second population comprises the specific binding agent that specifically binds to the target molecules. In some examples, the first population of origin-specific barcodes further comprises a target nucleic acid barcode, wherein the target nucleic acid barcode identifies the population as one that labels nucleic acids. In some examples, the second population of origin-specific barcodes further comprises a target molecule barcode, wherein the target molecule barcode identifies the population as one that labels target molecules.

EXAMPLES

Example 1—GWAS Identifies Bivariate Loci for BMD and Glycemic Traits, Including a Locus at 3q21.1

Applicants used GWAS summary statistics to identify genetic loci that may have pleiotropic effects on skeletal and glycaemic traits. Femoral neck BMD and lumbar spine BMD were used as quantitative endophenotypes that are strongly predictive of osteoporotic fracture, and fasting glucose, fasting insulin, HOMA-IR and HOMA-B were used to define T2D. Applicants elucidated the functional basis of the most intriguing bivariate GWAS locus, at 3q21.1, which was associated with femoral neck BMD and fasting glucose. The GWAS signal was driven by rs56371916, an intronic variant in Adenylate Cyclase 5 (ADCY5) that alters the binding affinity of Sterol Regulatory Element Binding Protein 1 (SREBP1), and leads to differential ADCY5 gene expression and cell-autonomous change in fatty acid metabolism in mature adipocytes and differentiating osteoblasts. Importantly, Applicants demonstrate that disruption of the regulator SREBP1, the variant rs56371916 and the target gene ADCY5 each cause cellular changes (e.g., lipid oxidation) relevant for BMD and T2D. Applicants' work identifies a novel link between fatty acid oxidation and osteoblast differentiation. More generally, they introduce a framework to uncover novel biological mechanisms, by identification and functional dissection of pleiotropic GWAS loci.

To discover genetic loci with possible pleiotropic effects on glycaemic traits and bone mineral density (BMD) traits, Applicants used GWAS summary statistics from the MAGIC consortium (in which the four glycemic traits HOMA-IR, HOMA-B, fasting glucose levels, and fasting insulin levels were measured) (Dupuis et al. 2010; Manning et al. 2012) and the GEFOS consortium (in which femoral neck BMD (FNBMD) and lumbar spine BMD (LSBMD) were measured) (Estrada et al. 2012).

To identify candidate pleiotropic loci, Applicants used the CPASSOC program (Park et al. 2016) to consider all 8 pairs of the two BMD traits and four glycaemic traits. Applicants identified 8 distinct bivariate loci—that is, loci with effects on both BMD and glycaemia (bivariate p-value≤5×10-6) (Methods, Tables 1-3, FIG. 1A). Consistent with most published GWAS, only one locus (at GCKR) harbored a protein-coding variant in strong LD with the lead variant. Notably, heritability partitioning across the entire bivariate GWAS revealed that the bivariate signal was globally enriched for enhancer annotations, particularly for H3K4me1, a mark enriched at active and primed enhancers, in the mesenchymal lineage, including adipocytes, osteoblasts, and other mesenchymal cells (FIG. 1B-C) (Finucane et al. 2015).

TABLE 1

Independent loci implicated by CP-ASSOC for association
with both bone mineral density and glycaemic traits.

| Locus | SNP rs# | Chr | Pos (GRCh37) | Ancestral | Derived | Derived Allele Frequency | Singleton Density Score | Variant Classes |
|---|---|---|---|---|---|---|---|---|
| GCKR | rs780110 | 2 | 27685388 | A | G | 0.56 | −1.08 | 3'UTR, synonymous, intronic, intergenic |

TABLE 1-continued

Independent loci implicated by CP-ASSOC for association
with both bone mineral density and glycaemic traits.

| | | | | | | | Derived Allele Frequency | | |
| Locus | SNP rs# | Chr | Pos (GRCh37) | Ancestral | Derived | | Singleton Density Score | Variant Classes |
|---|---|---|---|---|---|---|---|---|
| | rs1260326 | 2 | 27730940 | C | T | 0.40 | −0.97 | missense, intronic, intergenic |
| IGF1 | rs2607988 | 12 | 102929883 | G | A | 0.84 | −0.69 | intergenic |
| ADRA2A | rs11595612 | 10 | 112972505 | C | T | 0.09 | 1.67 | intergenic |
| | rs11195496 | 10 | 113021531 | G | T | 0.09 | 1.40 | intergenic |
| TCF7L2 | rs17747324 | 10 | 114752503 | T | C | 0.22 | −1.34 | intronic |
| CYP19A1 | rs1062033 | 15 | 51547938 | C | G | 0.46 | 1.12 | intronic intronic |
| ADCY5 | rs2124500 | 3 | 123093530 | C | T | 0.27 | 1.94 | intronic |
| | rs11717195 | 3 | 123082398 | T | C | 0.25 | 1.79 | intronic |
| POM121C | rs6944634 | 7 | 75061769 | C | G | 0.19 | N/A | intronic |
| SUSD4 | rs17161988 | 1 | 223444263 | A | G | 0.57 | −0.43 | intronic |

TABLE 2

| | Bivariate | Bone Traits (GEFOS) | | | Glycemic Traits (MAGIC) | | |
| Locus | P-value | Trait | P-value | Effect | Trait | P-value | Effect |
|---|---|---|---|---|---|---|---|
| GCKR | 2.54E−15 | LSBMD | 4.49E−05 | 4.08 | FG | 2.84E−12 | 6.99 |
| | 1.44E−10 | LSBMD | 3.64E−03 | 2.91 | FI | 1.18E−08 | 5.70 |
| IGF1 | 4.71E−11 | LSBMD | 7.15E−03 | −2.69 | FI | 1.96E−09 | −6.00 |
| ADRA2A | 1.03E−10 | LSBMD | 5.29E−03 | 2.79 | FG | 1.07E−09 | 6.10 |
| | 6.22E−09 | FNBMD | 6.78E−03 | 2.71 | HOMAB | 2.47E−07 | 5.16 |
| TCF7L2 | 9.14E−09 | FNBMD | 9.57E−03 | −2.59 | HOMAB | 2.33E−07 | −5.17 |
| CYP19A1 | 1.11E−07 | FNBMD | 1.61E−05 | −4.31 | HOMAIR | 1.32E−04 | −3.82 |
| | 4.20E−07 | FNBMD | 1.61E−05 | −4.31 | HOMAB | 1.45E−03 | −3.19 |
| ADCY5 | 1.83E−07 | FNBMD | 2.96E−03 | 2.97 | FG | 2.26E−06 | 4.73 |
| | 9.25E−07 | FNBMD | 3.99E−03 | 2.88 | HOMAB | 5.39E−05 | 4.04 |
| POM121C | 2.46E−07 | LSBMD | 3.22E−03 | −2.95 | FI | 1.23E−05 | −4.37 |
| SUSD4 | 2.82E−07 | FNBMD | 6.54E−05 | 3.99 | HOMAB | 4.71E−04 | 3.50 |

TABLE 3

Bivariate SNP associations discovered using CP-ASSOC. Associations with all pairs
of tested traits for which the SNP passed the bivariate threshold are shown.

| Bone Traits (GEFOS) | Glycemic Traits (MAGIC) | SNP rs# | L2_0 | Z1 | N1 | CM_0 | Minor Allele Frequency_0 | LD_weights |
|---|---|---|---|---|---|---|---|---|
| GEFOS_LSBMD | MAGIC_2012FG | rs780093 | 187.4 | −2.978 | 32961 | 47.353079 | 0.41292876 | 52.3075871 |
| GEFOS_LSBMD | MAGIC_2012FG | rs1260326 | 170.113 | −3.118 | 32961 | 47.348929 | 0.41292876 | 48.96009855 |
| GEFOS_LSBMD | MAGIC_2012FG | rs780094 | 185.79 | −2.957 | 32961 | 47.352649 | 0.414248021 | 50.75287666 |
| GEFOS_LSBMD | MAGIC_2012FG | rs780110 | 256.367 | 4.239 | 32961 | 47.344262 | 0.418205805 | 73.6261549 |
| GEFOS_LSBMD | MAGIC_2012FG | rs7586601 | 255.566 | −4.108 | 32961 | 47.340509 | 0.415567282 | 72.23766096 |
| GEFOS_LSBMD | MAGIC_2012FG | rs3739095 | 256.062 | 3.949 | 32961 | 47.334203 | 0.41292876 | 72.07656967 |
| GEFOS_LSBMD | MAGIC_2012FG | rs4665969 | 281.54 | −3.628 | 32961 | 47.337002 | 0.389182058 | 76.9419583 |
| GEFOS_LSBMD | MAGIC_2012FG | rs6743819 | 282.487 | 3.66 | 32961 | 47.335776 | 0.390501319 | 77.09585534 |
| GEFOS_LSBMD | MAGIC_2012FG | rs6760828 | 279.55 | −3.628 | 32961 | 47.338898 | 0.389182058 | 75.81252497 |
| GEFOS_LSBMD | MAGIC_2012FG | rs1049817 | 281.814 | −3.67 | 32961 | 47.333337 | 0.390501319 | 77.09585534 |
| GEFOS_LSBMD | MAGIC_2012FG | rs2280737 | 275.311 | −3.591 | 32961 | 47.342196 | 0.377308707 | 76.77541178 |
| GEFOS_LSBMD | MAGIC_2012FG | rs4665991 | 177.645 | −2.788 | 32961 | 47.357353 | 0.273087071 | 47.42694301 |
| GEFOS_LSBMD | MAGIC_2012FG | rs4665382 | 177.645 | 2.817 | 32961 | 47.35741 | 0.273087071 | 47.42694301 |
| GEFOS_LSBMD | MAGIC_2012FG | rs13472 | 275.982 | 3.602 | 32961 | 47.342288 | 0.374670185 | 77.38107357 |
| GEFOS_LSBMD | MAGIC_2012FG | rs1919128 | 177.645 | 2.835 | 32961 | 47.357495 | 0.273087071 | 47.42694301 |
| GEFOS_LSBMD | MAGIC_2012FG | rs7602534 | 276.131 | 3.57 | 32961 | 47.342219 | 0.375989446 | 76.80776501 |
| GEFOS_LSBMD | MAGIC_2012FG | rs12478841 | 177.645 | 2.816 | 32961 | 47.357793 | 0.275725594 | 46.57450056 |
| GEFOS_LSBMD | MAGIC_2012FG | rs780102 | 286.784 | −3.785 | 32961 | 47.344294 | 0.385224274 | 79.32027287 |
| GEFOS_LSBMD | MAGIC_2012FG | rs1335715 | 98.854 | −2.881 | 32961 | 137.34355 | 0.07651715 | 16.4204201 |
| GEFOS_LSBMD | MAGIC_2012FG | rs780107 | 286.464 | −3.774 | 32961 | 47.344262 | 0.386543536 | 79.32715218 |
| GEFOS_LSBMD | MAGIC_2012FG | rs11595612 | 98.794 | −3.006 | 32961 | 137.34204 | 0.077836412 | 16.62873183 |
| GEFOS_LSBMD | MAGIC_2012FG | rs10509938 | 100.847 | −2.623 | 32961 | 137.35683 | 0.075197889 | 16.0046566 |
| GEFOS_LSBMD | MAGIC_2012FG | rs1260342 | 286.784 | 3.763 | 32961 | 47.344251 | 0.385224274 | 79.32027287 |

TABLE 3-continued

Bivariate SNP associations discovered using CP-ASSOC. Associations with all pairs
of tested traits for which the SNP passed the bivariate threshold are shown.

| | | | | | | | | |
|---|---|---|---|---|---|---|---|---|
| GEFOS_FNBMD | MAGIC_2012FG | rs10509938 | 100.847 | -2.916 | 32961 | 137.35683 | 0.075197889 | 16.0046566 |
| GEFOS_LSBMD | MAGIC_2012FG | rs1647284 | 283.283 | 3.57 | 32961 | 47.342357 | 0.382585752 | 78.32344194 |
| GEFOS_LSBMD | MAGIC_2012FG | rs11817468 | 98.654 | 2.894 | 32961 | 137.34452 | 0.077836412 | 16.62873183 |
| GEFOS_LSBMD | MAGIC_2012FG | rs780104 | 286.464 | 3.731 | 32961 | 47.344258 | 0.386543536 | 79.32715218 |
| GEFOS_LSBMD | MAGIC_2012FG | rs1647276 | 286.453 | 3.763 | 32961 | 47.344264 | 0.383905013 | 79.10418079 |
| GEFOS_LSBMD | MAGIC_2012FG | rs17775480 | 98.794 | -2.943 | 32961 | 137.34305 | 0.077836412 | 16.62873183 |
| GEFOS_FNBMD | MAGIC_2012FG | rs1335715 | 98.854 | -3.061 | 32961 | 137.34355 | 0.07651715 | 16.4204201 |
| GEFOS_LSBMD | MAGIC_2012FG | rs780106 | 286.464 | -3.763 | 32961 | 47.34426 | 0.386543536 | 79.32715218 |
| GEFOS_LSBMD | MAGIC_2012FG | rs2293571 | 278.237 | 3.645 | 32961 | 47.348458 | 0.375989446 | 78.82794657 |
| GEFOS_LSBMD | MAGIC_2012FG | rs4803 | 286.234 | -3.72 | 32961 | 47.344253 | 0.383905013 | 79.08561667 |
| GEFOS_LSBMD | MAGIC_2012FG | rs6547626 | 284.093 | 3.57 | 32961 | 47.343226 | 0.383905013 | 78.5941684 |
| GEFOS_LSBMD | MAGIC_2012FG | rs1728922 | 283.283 | -3.57 | 32961 | 47.343171 | 0.378627968 | 75.82886126 |
| GEFOS_LSBMD | MAGIC_2012FG | rs1060525 | 283.283 | -3.559 | 32961 | 47.343104 | 0.382585752 | 78.32344194 |
| GEFOS_LSBMD | MAGIC_2012FG | rs4665976 | 283.283 | -3.559 | 32961 | 47.34314 | 0.382585752 | 78.32344194 |
| GEFOS_LSBMD | MAGIC_2012FG | rs7563162 | 281.525 | 3.548 | 32961 | 47.343071 | 0.382585752 | 78.32344194 |
| GEFOS_LSBMD | MAGIC_2012FG | rs1647266 | 286.131 | -3.71 | 32961 | 47.344266 | 0.385224274 | 79.11139057 |
| GEFOS_LSBMD | MAGIC_2012FG | rs704791 | 286.784 | -3.72 | 32961 | 47.344248 | 0.385224274 | 79.32027287 |
| GEFOS_LSBMD | MAGIC_2012FG | rs704795 | 285.97 | 3.742 | 32961 | 47.344587 | 0.385224274 | 79.54318937 |
| GEFOS_FNBMD | MAGIC_2012FG | rs11595612 | 98.794 | -3.068 | 32961 | 137.34204 | 0.077836412 | 16.62873183 |
| GEFOS_FNBMD | MAGIC_2012FG | rs4258313 | 97.431 | -2.932 | 32961 | 137.35777 | 0.07651715 | 15.27821756 |
| GEFOS_FNBMD | MAGIC_2012FG | rs17775480 | 98.794 | -3.02 | 32961 | 137.34305 | 0.077836412 | 16.62873183 |
| GEFOS_LSBMD | MAGIC_2012FI | rs2607988 | 109.005 | -2.913 | 32961 | 120.0004 | 0.17414248 | 28.91840147 |
| GEFOS_FNBMD | MAGIC_2012FG | rs11817468 | 98.654 | 2.924 | 32961 | 137.34452 | 0.077836412 | 16.62873183 |
| GEFOS_LSBMD | MAGIC_2012FG | rs1919127 | 177.645 | 2.835 | 32961 | 47.357488 | 0.273087071 | 47.42694301 |
| GEFOS_LSBMD | MAGIC_2012FG | rs813592 | 285.081 | -3.591 | 32961 | 47.34614 | 0.385224274 | 79.31296757 |
| GEFOS_LSBMD | MAGIC_2012FG | rs1260320 | 285.112 | 3.57 | 32961 | 47.346247 | 0.383905013 | 79.31676873 |
| GEFOS_LSBMD | MAGIC_2012FI | rs1260326 | 170.113 | -3.118 | 32961 | 47.348929 | 0.41292876 | 48.96009855 |
| GEFOS_LSBMD | MAGIC_2012FI | rs780094 | 185.79 | -2.957 | 32961 | 47.352649 | 0.414248021 | 50.75287666 |
| GEFOS_LSBMD | MAGIC_2012FG | rs11684134 | 234.968 | -3.417 | 32961 | 47.334435 | 0.419525066 | 66.75211535 |
| GEFOS_LSBMD | MAGIC_2012FI | rs780093 | 187.4 | -2.978 | 32961 | 47.353079 | 0.41292876 | 52.3075871 |
| GEFOS_LSBMD | MAGIC_2012FG | rs11681351 | 275.277 | 3.279 | 32961 | 47.353301 | 0.382585752 | 76.49726743 |
| GEFOS_LSBMD | MAGIC_2012FG | rs8179252 | 275.277 | -3.301 | 32961 | 47.353883 | 0.385224274 | 75.50059324 |
| GEFOS_FNBMD | MAGIC_2012FG | rs10509937 | 97.331 | 2.746 | 32961 | 137.35694 | 0.088390501 | 15.78275391 |
| GEFOS_LSBMD | MAGIC_2012FI | rs703545 | 106.574 | 2.727 | 32961 | 120.00844 | 0.180738786 | 28.68476403 |
| GEFOS_LSBMD | MAGIC_2012FI | rs10860877 | 94.61 | 2.744 | 32961 | 120.02439 | 0.166226913 | 25.48786906 |
| GEFOS_FNBMD | MAGIC_2012FG | rs10787315 | 96.105 | -2.717 | 32961 | 137.35784 | 0.089709763 | 15.50770369 |
| GEFOS_LSBMD | MAGIC_2012FI | rs10778177 | 108.313 | -2.911 | 32961 | 120.00625 | 0.171503958 | 28.86345284 |
| GEFOS_LSBMD | MAGIC_2012FG | rs13023094 | 168.453 | 2.626 | 32961 | 47.370198 | 0.225593668 | 44.61544617 |
| GEFOS_LSBMD | MAGIC_2012FG | rs13404327 | 195.829 | 3.574 | 32961 | 47.330619 | 0.23878628 | 54.35412855 |
| GEFOS_LSBMD | MAGIC_2012FG | rs13404446 | 195.829 | 3.574 | 32961 | 47.33062 | 0.23878628 | 54.35412855 |
| GEFOS_FNBMD | MAGIC_2012FG | rs11717195 | 68.46 | 3.091 | 32961 | 135.65826 | 0.182058047 | 13.35440172 |
| GEFOS_LSBMD | MAGIC_2012FG | rs4665963 | 187.847 | -3.564 | 32961 | 47.330697 | 0.244063325 | 51.68889707 |
| GEFOS_LSBMD | MAGIC_2012FG | rs4665965 | 193.507 | -3.564 | 32961 | 47.33062 | 0.240105541 | 53.7049762 |
| GEFOS_LSBMD | MAGIC_2012FG | rs2272417 | 266.022 | -3.272 | 32961 | 47.344273 | 0.405013193 | 72.38495668 |
| GEFOS_LSBMD | MAGIC_2012FG | rs1659685 | 183.96 | -3.418 | 32961 | 47.324553 | 0.275725594 | 49.08112113 |
| GEFOS_LSBMD | MAGIC_2012FI | rs4764702 | 105.988 | -2.797 | 32961 | 120.00638 | 0.168865435 | 28.74790671 |
| GEFOS_LSBMD | MAGIC_2012FG | rs1260345 | 273.067 | -3.217 | 32961 | 47.344271 | 0.411609499 | 73.28306447 |
| GEFOS_LSBMD | MAGIC_2012FG | rs13030973 | 165.306 | 2.605 | 32961 | 47.372716 | 0.225593668 | 44.61544617 |
| GEFOS_LSBMD | MAGIC2010HOMAB | rs17775480 | 98.794 | -2.943 | 32961 | 137.34305 | 0.077836412 | 16.62873183 |
| GEFOS_LSBMD | MAGIC2010HOMAB | rs11595612 | 98.794 | -3.006 | 32961 | 137.34204 | 0.077836412 | 16.62873183 |
| GEFOS_LSBMD | MAGIC_2012FG | rs1275501 | 183.96 | 3.227 | 32961 | 47.324546 | 0.275725594 | 49.08112113 |
| GEFOS_FNBMD | MAGIC2010HOMAIR | rs10459592 | 178.356 | -4.267 | 32961 | 70.555935 | 0.447229551 | 57.96982769 |
| GEFOS_FNBMD | MAGIC2010HOMAIR | rs10851498 | 183.394 | -4.604 | 32961 | 70.556449 | 0.451187335 | 66.44312881 |
| GEFOS_FNBMD | MAGIC2010HOMAIR | rs17523270 | 183.394 | 4.579 | 32961 | 70.558825 | 0.451187335 | 66.44312881 |
| GEFOS_LSBMD | MAGIC_2012FG | rs1395 | 176.173 | -3.165 | 32961 | 47.324573 | 0.290237467 | 46.16968625 |
| GEFOS_LSBMD | MAGIC_2012FG | rs1275522 | 183.96 | -3.206 | 32961 | 47.324584 | 0.275725594 | 49.08112113 |
| GEFOS_LSBMD | MAGIC_2012FG | rs1141313 | 183.96 | -3.124 | 32961 | 47.325688 | 0.275725594 | 49.08112113 |
| GEFOS_LSBMD | MAGIC_2012FG | rs1275528 | 183.96 | 3.144 | 32961 | 47.325055 | 0.275725594 | 49.08112113 |
| GEFOS_LSBMD | MAGIC_2012FG | rs4665958 | 183.96 | -3.113 | 32961 | 47.325186 | 0.275725594 | 49.08112113 |
| GEFOS_LSBMD | MAGIC_2012FG | rs3769143 | 182.928 | 3.124 | 32961 | 47.325206 | 0.275725594 | 49.08112113 |
| GEFOS_LSBMD | MAGIC_2012FG | rs1275530 | 183.96 | 3.124 | 32961 | 47.325158 | 0.275725594 | 49.08112113 |
| GEFOS_FNBMD | MAGIC2010HOMAB | rs11595612 | 98.794 | -3.068 | 32961 | 137.34204 | 0.077836412 | 16.62873183 |
| GEFOS_LSBMD | MAGIC2010HOMAIR | rs1260326 | 170.113 | -3.118 | 32961 | 47.348929 | 0.41292876 | 48.96009855 |
| GEFOS_FNBMD | MAGIC2010HOMAIR | rs12908960 | 181.454 | 4.295 | 32961 | 70.56573 | 0.430079156 | 66.09012942 |
| GEFOS_FNBMD | MAGIC_2012FG | rs10838681 | 1128.045 | 2.717 | 32961 | 66.496652 | 0.269129288 | 131.6561487 |
| GEFOS_LSBMD | MAGIC_2012FG | rs4582 | 283.283 | 3-.57 | 32961 | 47.342323 | 0.385224274 | 76.92662717 |
| GEFOS_LSBMD | MAGIC_2012FI | rs703548 | 91.643 | 2.608 | 32961 | 120.00919 | 0.155672823 | 26.71745082 |
| GEFOS_FNBMD | MAGIC2010HOMAIR | rs12050772 | 181.454 | -4.308 | 32961 | 70.564432 | 0.431398417 | 65.97665858 |
| GEFOS_FNBMD | MAGIC2010HOMAIR | rs780094 | 185.79 | -2.957 | 32961 | 47.352649 | 0.414248021 | 50.75287666 |
| GEFOS_LSBMD | MAGIC2010HOMAB | rs1335715 | 98.854 | -2.881 | 32961 | 137.34355 | 0.07651715 | 16.4204201 |
| GEFOS_LSBMD | MAGIC_2012FG | rs1659689 | 180.497 | 3.184 | 32961 | 47.319436 | 0.292875989 | 46.52347623 |
| GEFOS_LSBMD | MAGIC2010HOMAB | rs11817468 | 98.654 | 2.894 | 32961 | 137.34452 | 0.077836412 | 16.62873183 |
| GEFOS_FNBMD | MAGIC2010HOMAB | rs1335715 | 98.854 | -3.061 | 32961 | 137.34355 | 0.07651715 | 16.4204201 |
| GEFOS_FNBMD | MAGIC_2012FG | rs2877716 | 70.522 | -3.189 | 32961 | 135.66373 | 0.19525066 | 13.22371544 |
| GEFOS_FNBMD | MAGIC2010HOMAIR | rs4775936 | 183.394 | 4.565 | 32961 | 70.555865 | 0.449868074 | 66.40558056 |
| GEFOS_LSBMD | MAGIC2010HOMAIR | rs780093 | 187.4 | -2.978 | 32961 | 47.353079 | 0.41292876 | 52.3075871 |
| GEFOS_FNBMD | MAGIC_2012FG | rs6798189 | 70.522 | -3.147 | 32961 | 135.66387 | 0.19525066 | 13.22371544 |

TABLE 3-continued

Bivariate SNP associations discovered using CP-ASSOC. Associations with all pairs
of tested traits for which the SNP passed the bivariate threshold are shown.

| | | | | | | | | |
|---|---|---|---|---|---|---|---|---|
| GEFOS_LSBMD | MAGIC_2012FG | rs1992291 | 208.744 | −3.056 | 32961 | 47.330392 | 0.2176781 | 56.61033499 |
| GEFOS_FNBMD | MAGIC_2012FG | rs6976501 | 228.074 | −2.852 | 32961 | 76.846822 | 0.213720317 | 52.60541817 |
| GEFOS_FNBMD | MAGIC2010HOMAIR | rs12907866 | 181.454 | −4.206 | 32961 | 70.565473 | 0.430079156 | 66.09012942 |
| GEFOS_LSBMD | MAGIC_2012FI | rs35749 | 91.643 | 2.585 | 32961 | 120.00782 | 0.155672823 | 26.71745082 |
| GEFOS_FNBMD | MAGIC2010HOMAIR | rs1065778 | 193.619 | −4.345 | 32961 | 70.552117 | 0.480211082 | 68.47838192 |
| GEFOS_FNBMD | MAGIC2010HOMAIR | rs10519297 | 187.722 | 4.024 | 32961 | 70.562109 | 0.469656992 | 67.15590173 |
| GEFOS_LSBMD | MAGIC2010HOMAIR | rs2607988 | 109.005 | −2.913 | 32961 | 120.0004 | 0.17414248 | 28.91840147 |
| GEFOS_FNBMD | MAGIC2010HOMAIR | rs767199 | 187.722 | 4.036 | 32961 | 70.561404 | 0.469656992 | 67.15590173 |
| GEFOS_FNBMD | MAGIC2010HOMAIR | rs3759811 | 190.772 | −4.332 | 32961 | 70.552336 | 0.480211082 | 67.83342553 |
| GEFOS_FNBMD | MAGIC2010HOMAIR | rs11636667 | 187.722 | 4.024 | 32961 | 70.562399 | 0.468337731 | 67.09354698 |
| GEFOS_LSBMD | MAGIC_2012FG | rs3770601 | 26.378 | −2.584 | 32961 | 185.87337 | 0.067282322 | 9.18141645 |
| GEFOS_FNBMD | MAGIC2010HOMAIR | rs700518 | 190.772 | −4.32 | 32961 | 70.55233 | 0.480211082 | 67.83342553 |
| GEFOS_FNBMD | MAGIC2010HOMAIR | rs8023263 | 185.94 | 4.406 | 32961 | 70.551098 | 0.48944591 | 66.69848974 |
| GEFOS_LSBMD | MAGIC_2012FG | rs10037415 | 68.879 | −3.897 | 32961 | 101.83894 | 0.216358839 | 18.70587014 |
| GEFOS_LSBMD | MAGIC_2012FG | rs1275538 | 183.96 | 3.01 | 32961 | 47.325181 | 0.277044855 | 48.67589161 |
| GEFOS_FNBMD | MAGIC2010HOMAIR | rs12591359 | 166.463 | −3.867 | 32961 | 70.560826 | 0.45646438 | 51.7598134 |
| GEFOS_LSBMD | MAGIC_2012FG | rs4148773 | 27.026 | −2.584 | 32961 | 185.87363 | 0.067282322 | 9.18141645 |
| GEFOS_FNBMD | MAGIC_2012FG | rs2715131 | 226.161 | −2.752 | 32961 | 76.840486 | 0.216358839 | 52.93363181 |
| GEFOS_FNBMD | MAGIC_2012FG | rs6960169 | 226.161 | 2.752 | 32961 | 76.844835 | 0.216358839 | 52.93363181 |
| GEFOS_LSBMD | MAGIC_2012FI | rs703549 | 83.084 | −2.667 | 32961 | 120.01162 | 0.139841689 | 24.87991746 |
| GEFOS_FNBMD | MAGIC2010HOMAB | rs17161988 | 141.908 | 4.154 | 32961 | 246.93688 | 0.42348285 | 35.63712623 |
| GEFOS_LSBMD | MAGIC_2012FI | rs13108763 | 209.979 | 2.744 | 32961 | 166.08883 | 0.344327177 | 47.37917707 |
| GEFOS_FNBMD | MAGIC2010HOMAIR | rs2289105 | 184.035 | −4.345 | 32961 | 70.548701 | 0.498680739 | 63.70517476 |
| GEFOS_FNBMD | MAGIC2010HOMAIR | rs11636403 | 160.215 | 3.878 | 32961 | 70.567562 | 0.424802111 | 59.46065239 |
| GEFOS_FNBMD | MAGIC_2012FG | rs2715133 | 226.161 | 2.692 | 32961 | 76.840631 | 0.216358839 | 52.93363181 |
| GEFOS_FNBMD | MAGIC2010HOMAIR | rs11636686 | 187.722 | 4.011 | 32961 | 70.56233 | 0.468337731 | 67.09354698 |
| GEFOS_FNBMD | MAGIC2010HOMAIR | rs2304463 | 184.041 | −4.357 | 32961 | 70.548902 | 0.498680739 | 64.23498561 |
| GEFOS_FNBMD | MAGIC2010HOMAIR | rs12900487 | 193.619 | −3.975 | 32961 | 70.552191 | 0.480211082 | 68.47838192 |
| GEFOS_LSBMD | MAGIC_2012FG | rs13396091 | 109.344 | 3.319 | 32961 | 167.071 | 0.428759894 | 21.75819928 |
| GEFOS_FNBMD | MAGIC2010HOMAIR | rs4774583 | 184.041 | −4.308 | 32961 | 70.548432 | 0.494722955 | 64.06981472 |
| GEFOS_LSBMD | MAGIC_2012FG | rs1561535 | 176.456 | 3.133 | 32961 | 47.326772 | 0.267810026 | 46.55307125 |
| GEFOS_FNBMD | MAGIC_2012FI | rs10459592 | 178.356 | −4.267 | 32961 | 70.555935 | 0.447229551 | 57.96982769 |
| GEFOS_LSBMD | MAGIC2010HOMAIR | rs3924462 | 438.126 | −3.495 | 32961 | 69.002275 | 0.428759894 | 127.7250651 |
| GEFOS_LSBMD | MAGIC_2012FI | rs4665991 | 177.645 | −2.788 | 32961 | 47.357353 | 0.273087071 | 47.42694301 |
| GEFOS_LSBMD | MAGIC_2012FG | rs1122227 | 196.978 | 3.136 | 32961 | 47.332347 | 0.216358839 | 54.73974087 |
| GEFOS_LSBMD | MAGIC_2012FI | rs4665382 | 177.645 | 2.817 | 32961 | 47.35741 | 0.273087071 | 47.42694301 |
| GEFOS_LSBMD | MAGIC_2012FG | rs13424245 | 109.344 | −3.308 | 32961 | 167.07102 | 0.428759894 | 21.75819928 |
| GEFOS_LSBMD | MAGIC_2012FI | rs1919127 | 177.645 | 2.835 | 32961 | 47.357488 | 0.273087071 | 47.42694301 |
| GEFOS_LSBMD | MAGIC2010HOMAIR | rs1568661 | 437.32 | −3.495 | 32961 | 69.002274 | 0.430079156 | 127.5210676 |
| GEFOS_FNBMD | MAGIC2010HOMAIR | rs8029120 | 184.035 | −4.32 | 32961 | 70.54823 | 0.497361478 | 64.29019189 |
| GEFOS_LSBMD | MAGIC_2012FG | rs1975384 | 199.567 | 3.127 | 32961 | 47.330875 | 0.212401055 | 56.08238098 |
| GEFOS_FNBMD | MAGIC2010HOMAIR | rs4324076 | 185.944 | −4.369 | 32961 | 70.549723 | 0.490765172 | 65.26210621 |
| GEFOS_FNBMD | MAGIC2010HOMAIR | rs4545755 | 172.471 | 3.804 | 32961 | 70.568337 | 0.41292876 | 62.74662898 |
| GEFOS_FNBMD | MAGIC2010HOMAIR | rs6493489 | 186.795 | 4.357 | 32961 | 70.550252 | 0.48944591 | 65.52067416 |
| GEFOS_LSBMD | MAGIC2010HOMAIR | rs885592 | 436.096 | −3.495 | 32961 | 69.002268 | 0.428759894 | 127.7250651 |
| GEFOS_FNBMD | MAGIC2010HOMAIR | rs1568661 | 437.32 | −3.288 | 32961 | 69.002274 | 0.430079156 | 127.5210676 |
| GEFOS_LSBMD | MAGIC2010HOMAIR | rs1464568 | 437.652 | 3.44 | 32961 | 69.002257 | 0.424802111 | 128.1835132 |
| GEFOS_LSBMD | MAGIC2010HOMAIR | rs11130199 | 437.32 | −3.451 | 32961 | 69.002279 | 0.430079156 | 127.5210676 |
| GEFOS_LSBMD | MAGIC_2012FI | rs1919128 | 177.645 | 2.835 | 32961 | 47.357495 | 0.273087071 | 47.42694301 |

| Bone Traits (GEFOS) | Z2 | N2 | stat_SHom | stat_SHet | p_SHom | p_SHet | P1 | P2 |
|---|---|---|---|---|---|---|---|---|
| GEFOS_LSBMD | −10.349 | 58074 | 108.8653246 | 108.8653246 | 1.74E−25 | 1.03E−26 | 0.00290136 | 4.23E−25 |
| GEFOS_LSBMD | −10.116 | 58074 | 106.081061 | 106.081061 | 7.08E−25 | 4.78E−26 | 0.001820828 | 4.69E−24 |
| GEFOS_LSBMD | −10.162 | 58074 | 105.2935983 | 105.2935983 | 7.38E−25 | 4.78E−26 | 0.003106481 | 2.93E−24 |
| GEFOS_LSBMD | 7.082 | 58074 | 67.40030069 | 67.40030069 | 2.22E−16 | 8.30E−17 | 2.25E−05 | 1.42E−12 |
| GEFOS_LSBMD | −7.123 | 58074 | 66.9403328 | 66.9403328 | 2.80E−16 | 1.07E−16 | 3.99E−05 | 1.06E−12 |
| GEFOS_LSBMD | 6.627 | 58074 | 58.88616618 | 58.88616618 | 1.67E−14 | 8.96E−15 | 7.85E−05 | 3.43E−11 |
| GEFOS_LSBMD | −6.225 | 58074 | 51.38958689 | 51.38958689 | 7.57E−13 | 5.53E−13 | 0.000285625 | 4.82E−10 |
| GEFOS_LSBMD | 6.177 | 58074 | 51.01564308 | 51.01564308 | 9.16E−13 | 6.79E−13 | 0.000252215 | 6.53E−10 |
| GEFOS_LSBMD | −6.188 | 58074 | 50.92997453 | 50.92997453 | 9.57E−13 | 7.12E−13 | 0.000285625 | 6.09E−10 |
| GEFOS_LSBMD | −6.157 | 58074 | 50.83713305 | 50.83713305 | 1.00E−12 | 7.49E−13 | 0.00024255 | 7.41E−10 |
| GEFOS_LSBMD | −6.065 | 58074 | 49.16442834 | 49.16442834 | 2.35E−12 | 1.88E−12 | 0.000329412 | 1.32E−09 |
| GEFOS_LSBMD | −6.509 | 58074 | 49.09859458 | 49.09859458 | 2.43E−12 | 1.95E−12 | 0.005303454 | 7.57E−11 |
| GEFOS_LSBMD | 6.479 | 58074 | 48.93117015 | 48.93117015 | 2.65E−12 | 2.14E−12 | 0.004847453 | 9.23E−11 |
| GEFOS_LSBMD | 6.039 | 58074 | 48.92308158 | 48.92308158 | 2.66E−12 | 2.15E−12 | 0.000315778 | 1.55E−09 |
| GEFOS_LSBMD | 6.425 | 58074 | 48.39899273 | 48.39899273 | 3.48E−12 | 2.86E−12 | 0.004582569 | 1.32E−10 |
| GEFOS_LSBMD | 6.002 | 58074 | 48.25835098 | 48.25835098 | 3.74E−12 | 3.09E−12 | 0.000356981 | 1.95E−09 |
| GEFOS_LSBMD | 6.406 | 58074 | 48.04161714 | 48.04161714 | 4.17E−12 | 3.49E−12 | 0.004862567 | 1.49E−10 |
| GEFOS_LSBMD | −5.802 | 58074 | 47.30191675 | 47.30191675 | 6.09E−12 | 5.23E−12 | 0.000153709 | 6.55E−09 |
| GEFOS_LSBMD | −6.304 | 58074 | 47.25494062 | 47.25494062 | 6.23E−12 | 5.37E−12 | 0.003964156 | 2.90E−10 |
| GEFOS_LSBMD | −5.799 | 58074 | 47.19261331 | 47.19261331 | 6.43E−12 | 5.56E−12 | 0.000160651 | 6.67E−09 |
| GEFOS_LSBMD | −6.209 | 58074 | 46.95644522 | 46.95644522 | 7.26E−12 | 6.33E−12 | 0.00264709 | 5.33E−10 |
| GEFOS_LSBMD | −6.405 | 58074 | 46.73831683 | 46.73831683 | 8.11E−12 | 7.14E−12 | 0.008715927 | 1.50E−10 |
| GEFOS_LSBMD | 5.761 | 58074 | 46.66727089 | 46.66727089 | 8.41E−12 | 7.42E−12 | 0.000167887 | 8.36E−09 |
| GEFOS_FNBMD | −6.405 | 58074 | 48.53935636 | 48.53935636 | 3.24E−12 | 7.52E−12 | 0.003545505 | 1.50E−10 |
| GEFOS_LSBMD | 5.858 | 58074 | 46.53668414 | 46.53668414 | 8.99E−12 | 7.97E−12 | 0.000356981 | 4.68E−09 |

TABLE 3-continued

Bivariate SNP associations discovered using CP-ASSOC. Associations with all pairs
of tested traits for which the SNP passed the bivariate threshold are shown.

| | | | | | | | | |
|---|---|---|---|---|---|---|---|---|
| GEFOS_LSBMD | 6.231 | 58074 | 46.47354601 | 46.47354601 | 9.29E−12 | 8.26E−12 | 0.003803682 | 4.63E−10 |
| GEFOS_LSBMD | 5.759 | 58074 | 46.43136648 | 46.43136648 | 9.49E−12 | 8.45E−12 | 0.000190721 | 8.46E−09 |
| GEFOS_LSBMD | 5.741 | 58074 | 46.43029152 | 46.43029152 | 9.49E−12 | 8.45E−12 | 0.000167887 | 9.41E−09 |
| GEFOS_LSBMD | −6.199 | 58074 | 46.41937769 | 46.41937769 | 9.55E−12 | 8.50E−12 | 0.003250484 | 5.68E−10 |
| GEFOS_FNBMD | −6.304 | 58074 | 48.2941133 | 48.2941133 | 3.67E−12 | 8.56E−12 | 0.002205991 | 2.90E−10 |
| GEFOS_LSBMD | −5.73 | 58074 | 46.30021 | 46.30021 | 1.01E−11 | 9.08E−12 | 0.000167887 | 1.00E−08 |
| GEFOS_LSBMD | 5.796 | 58074 | 46.29973684 | 46.29973684 | 1.01E−11 | 9.08E−12 | 0.000267392 | 6.79E−09 |
| GEFOS_LSBMD | −5.75 | 58074 | 46.25217997 | 46.25217997 | 1.04E−11 | 9.32E−12 | 0.000199223 | 8.92E−09 |
| GEFOS_LSBMD | 5.833 | 58074 | 46.24096945 | 46.24096945 | 1.05E−11 | 9.38E−12 | 0.000356981 | 5.44E−09 |
| GEFOS_LSBMD | −5.831 | 58074 | 46.217353 | 46.217353 | 1.06E−11 | 9.50E−12 | 0.000356981 | 5.51E−09 |
| GEFOS_LSBMD | −5.834 | 58074 | 46.18009526 | 46.18009526 | 1.08E−11 | 9.70E−12 | 0.00037227 | 5.41E−09 |
| GEFOS_LSBMD | −5.832 | 58074 | 46.15649435 | 46.15649435 | 1.09E−11 | 9.83E−12 | 0.00037227 | 5.48E−09 |
| GEFOS_LSBMD | 5.837 | 58074 | 46.14285254 | 46.14285254 | 1.10E−11 | 9.90E−12 | 0.000388168 | 5.31E−09 |
| GEFOS_LSBMD | −5.746 | 58074 | 46.1389022 | 46.1389022 | 1.10E−11 | 9.92E−12 | 0.000207259 | 9.14E−09 |
| GEFOS_LSBMD | −5.74 | 58074 | 46.13414369 | 46.13414369 | 1.10E−11 | 9.95E−12 | 0.000199223 | 9.47E−09 |
| GEFOS_LSBMD | 5.711 | 58074 | 45.93750705 | 45.93750705 | 1.22E−11 | 1.11E−11 | 0.000182562 | 1.12E−08 |
| GEFOS_FNBMD | −6.209 | 58074 | 47.20144109 | 47.20144109 | 6.41E−12 | 1.52E−11 | 0.002154966 | 5.33E−10 |
| GEFOS_FNBMD | −6.265 | 58074 | 46.96698119 | 46.96698119 | 7.22E−12 | 1.73E−11 | 0.003367867 | 3.73E−10 |
| GEFOS_FNBMD | −6.199 | 58074 | 46.76465836 | 46.76465836 | 8.00E−12 | 1.92E−11 | 0.002527747 | 5.68E−10 |
| GEFOS_LSBMD | 6.112 | 58074 | 15.03553466 | 45.60608598 | 0.000105506 | 1.93E−11 | 0.003579746 | 9.84E−10 |
| GEFOS_FNBMD | 6.231 | 58074 | 46.51069354 | 46.51069354 | 9.11E−12 | 2.20E−11 | 0.003455647 | 4.63E−10 |
| GEFOS_LSBMD | 6.093 | 58074 | 44.47082584 | 44.47082584 | 2.58E−11 | 2.48E−11 | 0.004582569 | 1.11E−09 |
| GEFOS_LSBMD | −5.602 | 58074 | 43.68796498 | 43.68796498 | 3.85E−11 | 3.82E−11 | 0.000329412 | 2.12E−08 |
| GEFOS_LSBMD | 5.602 | 58074 | 43.55315661 | 43.55315661 | 4.13E−11 | 4.11E−11 | 0.000356981 | 2.12E−08 |
| GEFOS_LSBMD | −5.82 | 58074 | 43.57062601 | 43.57062601 | 4.09E−11 | 5.81E−11 | 0.001820828 | 5.88E−09 |
| GEFOS_LSBMD | −5.911 | 58074 | 43.56620133 | 43.56620133 | 4.10E−11 | 5.83E−11 | 0.003106481 | 3.40E−09 |
| GEFOS_LSBMD | −5.618 | 58074 | 42.75877781 | 42.75877781 | 6.19E−11 | 6.37E−11 | 0.000633153 | 1.93E−08 |
| GEFOS_LSBMD | −5.781 | 58074 | 42.22109686 | 42.22109686 | 8.15E−11 | 1.21E−10 | 0.00290136 | 7.43E−09 |
| GEFOS_LSBMD | 5.554 | 58074 | 41.16992184 | 41.16992184 | 1.40E−10 | 1.52E−10 | 0.001041756 | 2.79E−08 |
| GEFOS_LSBMD | −5.497 | 58074 | 40.6734586 | 40.6734586 | 1.80E−10 | 2.00E−10 | 0.000963409 | 3.86E−08 |
| GEFOS_FNBMD | 5.957 | 58074 | 42.19945482 | 42.19945482 | 8.24E−11 | 2.14E−10 | 0.006032676 | 2.57E−09 |
| GEFOS_LSBMD | −5.753 | 58074 | 13.37486901 | 40.31247091 | 0.000255018 | 3.40E−10 | 0.006391304 | 8.77E−09 |
| GEFOS_LSBMD | −5.729 | 58074 | 13.16167413 | 40.15412939 | 0.000285733 | 3.70E−10 | 0.006069554 | 1.01E−08 |
| GEFOS_FNBMD | −5.864 | 58074 | 40.97783498 | 40.97783498 | 1.54E−10 | 4.09E−10 | 0.006587661 | 4.52E−09 |
| GEFOS_LSBMD | 5.531 | 58074 | 11.37890915 | 39.02448199 | 0.000742827 | 6.83E−10 | 0.00360274 | 3.18E−08 |
| GEFOS_LSBMD | 5.535 | 58074 | 36.99720585 | 36.99720585 | 1.18E−09 | 1.51E−09 | 0.008639482 | 3.11E−08 |
| GEFOS_LSBMD | 4.993 | 58074 | 36.87644619 | 36.87644619 | 1.26E−09 | 1.62E−09 | 0.000351569 | 5.94E−07 |
| GEFOS_LSBMD | 4.992 | 58074 | 36.86590061 | 36.86590061 | 1.27E−09 | 1.63E−09 | 0.000351569 | 5.98E−07 |
| GEFOS_FNBMD | 5.393 | 58074 | 38.10917613 | 38.10917613 | 6.61E−10 | 1.86E−09 | 0.001994836 | 6.93E−08 |
| GEFOS_LSBMD | −4.97 | 58074 | 36.57547355 | 36.57547355 | 1.47E−09 | 1.91E−09 | 0.000365246 | 6.70E−07 |
| GEFOS_LSBMD | −4.946 | 58074 | 36.32383103 | 36.32383103 | 1.67E−09 | 2.19E−09 | 0.000365246 | 7.58E−07 |
| GEFOS_LSBMD | −5.081 | 58074 | 36.02695608 | 36.02695608 | 1.95E−09 | 2.58E−09 | 0.001067896 | 3.75E−07 |
| GEFOS_LSBMD | −4.98 | 58074 | 35.82616066 | 35.82616066 | 2.16E−09 | 2.88E−09 | 0.000630831 | 6.36E−07 |
| GEFOS_LSBMD | 5.345 | 58074 | 10.67836517 | 36.34801209 | 0.001083958 | 2.91E−09 | 0.005157953 | 9.04E−08 |
| GEFOS_LSBMD | −4.907 | 58074 | 33.92390588 | 33.92390588 | 5.73E−09 | 8.19E−09 | 0.001295386 | 9.25E−07 |
| GEFOS_LSBMD | 5.135 | 58074 | 32.77546055 | 32.77546055 | 1.03E−08 | 1.54E−08 | 0.009187426 | 2.82E−07 |
| GEFOS_LSBMD | 5.107 | 46186 | 5.993372644 | 34.45545775 | 0.014359722 | 1.70E−08 | 0.003250484 | 3.27E−07 |
| GEFOS_LSBMD | 5.024 | 46186 | 5.494543326 | 34.09317974 | 0.019075909 | 2.05E−08 | 0.00264709 | 5.06E−07 |
| GEFOS_LSBMD | 4.691 | 58074 | 31.8289891 | 31.8289891 | 1.68E−08 | 2.59E−08 | 0.001250955 | 2.72E−06 |
| GEFOS_FNBMD | 3.976 | 46186 | 0.600384547 | 33.06012226 | 0.438431341 | 2.59E−08 | 1.98E−05 | 7.01E−05 |
| GEFOS_FNBMD | 3.716 | 46186 | 0.136925795 | 32.89455492 | 0.711356519 | 2.83E−08 | 4.14E−06 | 0.000202402 |
| GEFOS_FNBMD | −3.73 | 46186 | 0.156635822 | 32.85732433 | 0.692272912 | 2.89E−08 | 4.67E−06 | 0.00019148 |
| GEFOS_LSBMD | −4.705 | 58074 | 31.62650299 | 31.62650299 | 1.87E−08 | 2.90E−08 | 0.00155083 | 2.54E−06 |
| GEFOS_LSBMD | −4.681 | 58074 | 31.61621075 | 31.61621075 | 1.88E−08 | 2.91E−08 | 0.00134594 | 2.85E−06 |
| GEFOS_LSBMD | −4.693 | 58074 | 31.28611211 | 31.28611211 | 2.23E−08 | 3.49E−08 | 0.001784105 | 2.69E−06 |
| GEFOS_LSBMD | 4.675 | 58074 | 31.22002538 | 31.22002538 | 2.30E−08 | 3.62E−08 | 0.001666554 | 2.94E−06 |
| GEFOS_LSBMD | −4.685 | 58074 | 31.14874776 | 31.14874776 | 2.39E−08 | 3.77E−08 | 0.00185196 | 2.80E−06 |
| GEFOS_LSBMD | 4.667 | 58074 | 31.03405526 | 31.03405526 | 2.54E−08 | 4.01E−08 | 0.001784105 | 3.06E−06 |
| GEFOS_LSBMD | 4.666 | 58074 | 31.02438112 | 31.02438112 | 2.55E−08 | 4.03E−08 | 0.001784105 | 3.07E−06 |
| GEFOS_FNBMD | 5.024 | 46186 | 5.321722403 | 34.46077584 | 0.021061184 | 4.14E−08 | 0.002154966 | 5.06E−07 |
| GEFOS_LSBMD | −4.909 | 46186 | 33.59382182 | 33.59382182 | 6.79E−09 | 4.33E−08 | 0.001820828 | 9.15E−07 |
| GEFOS_FNBMD | −3.82 | 46186 | 0.399553503 | 31.79716544 | 0.527319936 | 5.06E−08 | 1.75E−05 | 0.000133452 |
| GEFOS_FNBMD | 4.989 | 58074 | 31.83231482 | 31.83231482 | 1.68E−08 | 5.13E−08 | 0.006587661 | 6.07E−07 |
| GEFOS_LSBMD | −4.37 | 58074 | 30.57724572 | 30.57724572 | 3.21E−08 | 5.16E−08 | 0.000356981 | 1.24E−05 |
| GEFOS_LSBMD | −4.911 | 58074 | 8.902044601 | 30.89366677 | 0.002848515 | 5.59E−08 | 0.009107295 | 9.06E−07 |
| GEFOS_FNBMD | 3.776 | 46186 | 0.346813128 | 31.47899171 | 0.555922709 | 5.98E−08 | 1.65E−05 | 0.000159367 |
| GEFOS_FNBMD | −4.945 | 46186 | 32.85731488 | 32.85731488 | 9.92E−09 | 6.27E−08 | 0.003106481 | 7.61E−07 |
| GEFOS_LSBMD | 4.87 | 46186 | 5.249857574 | 31.81915244 | 0.021948567 | 6.63E−08 | 0.003964156 | 1.12E−06 |
| GEFOS_LSBMD | 4.529 | 58074 | 30.03202198 | 30.03202198 | 4.25E−08 | 6.96E−08 | 0.00145255 | 5.93E−06 |
| GEFOS_LSBMD | −4.826 | 46186 | 5.053100071 | 31.50107087 | 0.024581919 | 7.82E−08 | 0.003803682 | 1.39E−06 |
| GEFOS_FNBMD | 4.87 | 46186 | 4.776791203 | 32.95825592 | 0.028845823 | 8.59E−08 | 0.002205991 | 1.12E−06 |
| GEFOS_FNBMD | −4.625 | 46186 | 30.84776181 | 30.84776181 | 2.79E−08 | 8.63E−08 | 0.001427659 | 3.75E−06 |
| GEFOS_FNBMD | −3.506 | 46186 | 0.0492708 | 30.70357266 | 0.824337029 | 9.02E−08 | 4.99E−06 | 0.000454895 |
| GEFOS_LSBMD | −4.838 | 46186 | 32.00474104 | 32.00474104 | 1.54E−08 | 9.60E−08 | 0.00290136 | 1.31E−06 |
| GEFOS_FNBMD | −4.606 | 58074 | 30.4406186 | 30.4406186 | 3.44E−08 | 1.07E−07 | 0.00164955 | 4.10E−06 |
| GEFOS_LSBMD | −4.472 | 58074 | 28.8202109 | 28.8202109 | 7.94E−08 | 1.36E−07 | 0.002243113 | 7.75E−06 |
| GEFOS_FNBMD | −4.694 | 58074 | 29.71553424 | 29.71553424 | 5.00E−08 | 1.57E−07 | 0.00434451 | 2.68E−06 |

TABLE 3-continued

Bivariate SNP associations discovered using CP-ASSOC. Associations with all pairs
of tested traits for which the SNP passed the bivariate threshold are shown.

| | | | | | | | | |
|---|---|---|---|---|---|---|---|---|
| GEFOS_FNBMD | 3.626 | 46186 | 0.276435178 | 29.46657819 | 0.599047304 | 1.73E–07 | 2.60E–05 | 0.000287845 |
| GEFOS_LSBMD | –4.696 | 58074 | 7.884860378 | 28.72825353 | 0.004985033 | 1.80E–07 | 0.0097379 | 2.65E–06 |
| GEFOS_FNBMD | 3.511 | 46186 | 0.124257937 | 29.33341468 | 0.724461524 | 1.86E–07 | 1.39E–05 | 0.000446424 |
| GEFOS_FNBMD | –3.718 | 46186 | 0.497148018 | 29.12307994 | 0.480755946 | 2.08E–07 | 5.72E–05 | 0.000200806 |
| GEFOS_LSBMD | 4.678 | 46186 | 4.487541475 | 30.36444405 | 0.034142745 | 2.18E–07 | 0.003579746 | 2.90E–06 |
| GEFOS_FNBMD | –3.688 | 46186 | 0.454051917 | 28.9351168 | 0.500417018 | 2.30E–07 | 5.44E–05 | 0.000226024 |
| GEFOS_FNBMD | 3.446 | 46186 | 0.094375952 | 28.67975792 | 0.758686052 | 2.63E–07 | 1.48E–05 | 0.00056895 |
| GEFOS_FNBMD | –3.649 | 46186 | 0.421292915 | 28.51839026 | 0.516292609 | 2.86E–07 | 5.72E–05 | 0.000263263 |
| GEFOS_LSBMD | 4.527 | 58074 | 7.156989461 | 27.44543556 | 0.007467242 | 2.89E–07 | 0.009766179 | 5.98E–06 |
| GEFOS_FNBMD | 3.428 | 46186 | 0.089695599 | 28.44742993 | 0.764564496 | 2.97E–07 | 1.56E–05 | 0.000608045 |
| GEFOS_FNBMD | –3.344 | 46186 | 0.033072654 | 28.25484076 | 0.855693471 | 3.29E–07 | 1.05E–05 | 0.000825797 |
| GEFOS_FNBMD | –3.959 | 58074 | 28.28140893 | 28.28140893 | 1.05E–07 | 3.35E–07 | 9.74E–05 | 7.53E–05 |
| GEFOS_LSBMD | 4.312 | 58074 | 27.11445245 | 27.11445245 | 1.92E–07 | 3.46E–07 | 0.002612477 | 1.62E–05 |
| GEFOS_FNBMD | 3.713 | 46186 | 0.626130029 | 28.09369468 | 0.428778408 | 3.58E–07 | 0.000110182 | 0.000204817 |
| GEFOS_LSBMD | 4.455 | 58074 | 6.8263766 | 26.7921868 | 0.00898213 | 4.13E–07 | 0.009766179 | 8.39E–06 |
| GEFOS_FNBMD | –4.545 | 58074 | 27.81071464 | 27.81071464 | 1.34E–07 | 4.30E–07 | 0.005923252 | 5.49E–06 |
| GEFOS_FNBMD | 4.528 | 58074 | 27.65532285 | 27.65532285 | 1.45E–07 | 4.66E–07 | 0.005923252 | 5.95E–06 |
| GEFOS_LSBMD | 4.445 | 58074 | 6.498560139 | 26.85372109 | 0.010796189 | 4.98E–07 | 0.007653167 | 8.79E–06 |
| GEFOS_FNBMD | –3.677 | 46186 | 0.335462729 | 29.20977045 | 0.562460003 | 5.33E–07 | 3.27E–05 | 0.000235993 |
| GEFOS_FNBMD | 4.468 | 58074 | 27.23200686 | 27.23200686 | 1.80E–07 | 5.47E–07 | 0.006069554 | 7.90E–06 |
| GEFOS_FNBMD | 3.264 | 46186 | 0.02309786 | 27.19024809 | 0.879202868 | 5.77E–07 | 1.39E–05 | 0.001098512 |
| GEFOS_FNBMD | –3.59 | 46186 | 0.469368528 | 27.10670485 | 0.493277819 | 6.04E–07 | 0.000105319 | 0.000330678 |
| GEFOS_FNBMD | 4.503 | 58074 | 27.12490662 | 27.12490662 | 1.91E–07 | 6.17E–07 | 0.007102495 | 6.70E–06 |
| GEFOS_FNBMD | –3.48 | 46186 | 0.269718754 | 26.9848027 | 0.603520497 | 6.44E–07 | 6.05E–05 | 0.000501414 |
| GEFOS_FNBMD | 3.23 | 46186 | 0.01380131 | 26.97471526 | 0.906480504 | 6.47E–07 | 1.32E–05 | 0.001237902 |
| GEFOS_FNBMD | 3.504 | 46186 | 0.313067213 | 26.96879667 | 0.575804092 | 6.49E–07 | 7.04E–05 | 0.000458325 |
| GEFOS_LSBMD | 4.011 | 58074 | 25.96869154 | 25.96869154 | 3.47E–07 | 6.50E–07 | 0.000903404 | 6.05E–05 |
| GEFOS_FNBMD | 3.232 | 46186 | 0.021688929 | 26.69366091 | 0.882917634 | 7.51E–07 | 1.65E–05 | 0.001229271 |
| GEFOS_LSBMD | 4.085 | 58074 | 25.70301081 | 25.70301081 | 3.98E–07 | 7.52E–07 | 0.001730294 | 4.41E–05 |
| GEFOS_FNBMD | 3.471 | 58074 | 0.874231928 | 26.57688523 | 0.34978639 | 7.73E–07 | 1.98E–05 | 0.000518524 |
| GEFOS_LSBMD | –3.989 | 46186 | 27.7313639 | 27.7313639 | 1.39E–07 | 8.15E–07 | 0.000474062 | 6.64E–05 |
| GEFOS_LSBMD | –4.274 | 58074 | 25.9422768 | 25.9422768 | 3.52E–07 | 8.16E–07 | 0.005303454 | 1.92E–05 |
| GEFOS_LSBMD | 4.066 | 58074 | 25.55072922 | 25.55072922 | 4.31E–07 | 8.18E–07 | 0.001712692 | 4.78E–05 |
| GEFOS_LSBMD | 4.257 | 58074 | 25.9374994 | 25.9374994 | 3.53E–07 | 8.18E–07 | 0.004847453 | 2.07E–05 |
| GEFOS_LSBMD | –3.969 | 58074 | 25.5442488 | 25.5442488 | 4.32E–07 | 8.21E–07 | 0.000939648 | 7.22E–05 |
| GEFOS_LSBMD | 4.246 | 58074 | 25.93056366 | 25.93056366 | 3.54E–07 | 8.21E–07 | 0.004582569 | 2.18E–05 |
| GEFOS_LSBMD | –3.978 | 46186 | 27.63723651 | 27.63723651 | 1.46E–07 | 8.55E–07 | 0.000474062 | 6.95E–05 |
| GEFOS_FNBMD | 3.191 | 46186 | 0.011467832 | 26.42133955 | 0.914719194 | 8.67E–07 | 1.56E–05 | 0.001417813 |
| GEFOS_LSBMD | 4.057 | 58074 | 25.42765212 | 25.42765212 | 4.59E–07 | 8.75E–07 | 0.001765999 | 4.97E–05 |
| GEFOS_FNBMD | 3.151 | 46186 | 0.002157202 | 26.38138111 | 0.962955018 | 8.85E–07 | 1.25E–05 | 0.001627125 |
| GEFOS_FNBMD | –3.541 | 46186 | 0.473159465 | 26.24493549 | 0.491537247 | 9.52E–07 | 0.000142378 | 0.000398614 |
| GEFOS_FNBMD | –3.142 | 46186 | 0.002119472 | 26.23377274 | 0.96328018 | 9.57E–07 | 1.32E–05 | 0.00167798 |
| GEFOS_LSBMD | –3.951 | 46186 | 27.40687498 | 27.40687498 | 1.65E–07 | 9.59E–07 | 0.000474062 | 7.78E–05 |
| GEFOS_FNBMD | –3.978 | 46186 | 26.21097014 | 26.21097014 | 3.06E–07 | 9.69E–07 | 0.001009018 | 6.95E–05 |
| GEFOS_LSBMD | 3.986 | 46186 | 27.37165666 | 27.37165666 | 1.68E–07 | 9.76E–07 | 0.000581714 | 6.72E–05 |
| GEFOS_LSBMD | –3.975 | 46186 | 27.34467038 | 27.34467038 | 1.70E–07 | 9.90E–07 | 0.000558514 | 7.04E–05 |
| GEFOS_LSBMD | 4.206 | 58074 | 25.57748141 | 25.57748141 | 4.25E–07 | 9.94E–07 | 0.004582569 | 2.60E–05 |

A particularly interesting bivariate locus occurred at 3q21.1, within an intron of the ADCY5 gene. The signal was seen across multiple traits, methods and data sets. The locus is associated with FNBMD and glucose levels (lead SNP rs2124500, bivariate GWAS p-value=1.83×10-7, FIG. 2A), as well as FNBMD and HOMA-B (Tables 1, 2 and 4). The locus also showed a bivariate association when tested with two other established methods: MTAG (Turley et al. 2017) (p=3.22×10-9) and eLX (Chen et al. 2017) (p=5.73×10-9) (Tables 5, 6). Additionally, the locus showed bivariate association (CP-ASSOC p=1.35×10-7; eLX p=4.35×10-11; MTAG p=6.03×10-9) in independent data from the UK Biobank for heel BMD (n=194,398) and diagnosed diabetes (n=336,473) (Tables 7, 8). Finally, the 3q21.1 locus has recently been associated with heel BMD (UK Biobank, p=1.15×10-10, n=435,039, (Morris et al. 2018)).

TABLE 4

Detailed CP-ASSOC results for all SNPs at the 3q21.1 locus. For each SNP, the association
Z scores for each trait and the resulting CP-ASSOC pleiotropy p-values are recorded.

| CHR | SNP | CM | BP | Derived | Ancestral | bone | glucose | Z.bmd |
|---|---|---|---|---|---|---|---|---|
| 3 | rs2124500 | 135.66 | 1.23E+08 | T | C | gefos2012bmd_lumbar | magic2012_fg | –2.13722126 |
| 3 | rs2124500 | 135.66 | 1.23E+08 | T | C | gefos2012bmd_lumbar | magic2012_fi | –2.13722126 |
| 3 | rs2124500 | 135.66 | 1.23E+08 | T | C | gefos2012bmd_lumbar | magic2012_homair | –2.13722126 |
| 3 | rs2124500 | 135.66 | 1.23E+08 | T | C | gefos2012bmd_lumbar | magic2012_homab | –2.13722126 |
| 3 | rs2124500 | 135.66 | 1.23E+08 | T | C | gefos2012bmd_femur | magic2012_fg | –3.17818531 |
| 3 | rs2124500 | 135.66 | 1.23E+08 | T | C | gefos2012bmd_femur | magic2012_fi | –3.17818531 |
| 3 | rs2124500 | 135.66 | 1.23E+08 | T | C | gefos2012bmd_femur | magic2012_homab | –3.17818531 |
| 3 | rs2124500 | 135.66 | 1.23E+08 | T | C | gefos2012bmd_femur | magic2012_homair | –3.17818531 |
| 3 | rs2877716 | 135.66 | 1.23E+08 | T | C | gefos2012bmd_lumbar | magic2012_fg | –2.1177057 |

TABLE 4-continued

Detailed CP-ASSOC results for all SNPs at the 3q21.1 locus. For each SNP, the association
Z scores for each trait and the resulting CP-ASSOC pleiotropy p-values are recorded.

| | | | | | | | | | |
|---|---|---|---|---|---|---|---|---|---|
| 3 | rs2877716 | 135.66 | 1.23E+08 | T | C | gefos2012bmd_lumbar | magic2012_fi | | −2.1177057 |
| 3 | rs2877716 | 135.66 | 1.23E+08 | T | C | gefos2012bmd_lumbar | magic2012_homair | | −2.1177057 |
| 3 | rs2877716 | 135.66 | 1.23E+08 | T | C | gefos2012bmd_lumbar | magic2012_homab | | −2.1177057 |
| 3 | rs2877716 | 135.66 | 1.23E+08 | T | C | gefos2012bmd_femur | magic2012_fg | | −3.18872854 |
| 3 | rs2877716 | 135.66 | 1.23E+08 | T | C | gefos2012bmd_femur | magic2012_fi | | −3.18872854 |
| 3 | rs2877716 | 135.66 | 1.23E+08 | T | C | gefos2012bmd_femur | magic2012_homair | | −3.18872854 |
| 3 | rs6798189 | 135.66 | 1.23E+08 | A | G | gefos2012bmd_lumbar | magic2012_fg | | −2.09805825 |
| 3 | rs6798189 | 135.66 | 1.23E+08 | A | G | gefos2012bmd_lumbar | magic2012_fi | | −2.09805825 |
| 3 | rs6798189 | 135.66 | 1.23E+08 | A | G | gefos2012bmd_lumbar | magic2012_homair | | −2.09805825 |
| 3 | rs6798189 | 135.66 | 1.23E+08 | A | G | gefos2012bmd_lumbar | magic2012_homab | | −2.09805825 |
| 3 | rs6798189 | 135.66 | 1.23E+08 | A | G | gefos2012bmd_femur | magic2012_fg | | −3.14674302 |
| 3 | rs6798189 | 135.66 | 1.23E+08 | A | G | gefos2012bmd_femur | magic2012_fi | | −3.14674302 |
| 3 | rs6798189 | 135.66 | 1.23E+08 | A | G | gefos2012bmd_femur | magic2012_homab | | −3.14674302 |
| 3 | rs6798189 | 135.66 | 1.23E+08 | A | G | gefos2012bmd_femur | magic2012_homair | | −3.14674302 |
| 3 | rs9883204 | 135.67 | 1.23E+08 | T | C | gefos2012bmd_lumbar | magic2012_fg | | −1.96296707 |
| 3 | rs9883204 | 135.67 | 1.23E+08 | T | C | gefos2012bmd_lumbar | magic2012_fi | | −1.96296707 |
| 3 | rs9883204 | 135.67 | 1.23E+08 | T | C | gefos2012bmd_lumbar | magic2012_homair | | −1.96296707 |
| 3 | rs9883204 | 135.67 | 1.23E+08 | T | C | gefos2012bmd_lumbar | magic2012_homab | | −1.96296707 |
| 3 | rs9883204 | 135.67 | 1.23E+08 | T | C | gefos2012bmd_femur | magic2012_fg | | −2.89729137 |
| 3 | rs9883204 | 135.67 | 1.23E+08 | T | C | gefos2012bmd_femur | magic2012_fi | | −2.89729137 |
| 3 | rs9883204 | 135.67 | 1.23E+08 | T | C | gefos2012bmd_femur | magic2012_homab | | −2.89729137 |
| 3 | rs9883204 | 135.67 | 1.23E+08 | T | C | gefos2012bmd_femur | magic2012_homair | | −2.89729137 |
| 3 | rs11717195 | 135.66 | 1.23E+08 | C | T | gefos2012bmd_lumbar | magic2012_fg | | 1.64146947 |
| 3 | rs11717195 | 135.66 | 1.23E+08 | C | T | gefos2012bmd_lumbar | magic2012_fi | | 1.64146947 |
| 3 | rs11717195 | 135.66 | 1.23E+08 | C | T | gefos2012bmd_lumbar | magic2012_homair | | 1.64146947 |
| 3 | rs11717195 | 135.66 | 1.23E+08 | C | T | gefos2012bmd_lumbar | magic2012_homab | | 1.64146947 |
| 3 | rs11717195 | 135.66 | 1.23E+08 | C | T | gefos2012bmd_femur | magic2012_fg | | 3.09112451 |
| 3 | rs11717195 | 135.66 | 1.23E+08 | C | T | gefos2012bmd_femur | magic2012_fi | | 3.09112451 |
| 3 | rs11717195 | 135.66 | 1.23E+08 | C | T | gefos2012bmd_femur | magic2012_homab | | 3.09112451 |
| 3 | rs11717195 | 135.66 | 1.23E+08 | C | T | gefos2012bmd_femur | magic2012_homair | | 3.09112451 |
| 3 | rs7613951 | 135.65 | 1.23E+08 | T | C | gefos2012bmd_lumbar | magic2012_fg | | −1.41591634 |
| 3 | rs7613951 | 135.65 | 1.23E+08 | T | C | gefos2012bmd_lumbar | magic2012_fi | | −1.41591634 |
| 3 | rs7613951 | 135.65 | 1.23E+08 | T | C | gefos2012bmd_lumbar | magic2012_homair | | −1.41591634 |
| 3 | rs7613951 | 135.65 | 1.23E+08 | T | C | gefos2012bmd_lumbar | magic2012_homab | | −1.41591634 |
| 3 | rs7613951 | 135.65 | 1.23E+08 | T | C | gefos2012bmd_femur | magic2012_fg | | −2.60119364 |
| 3 | rs7613951 | 135.65 | 1.23E+08 | T | C | gefos2012bmd_femur | magic2012_fi | | −2.60119364 |
| 3 | rs7613951 | 135.65 | 1.23E+08 | T | C | gefos2012bmd_femur | magic2012_homab | | −2.60119364 |
| 3 | rs7613951 | 135.65 | 1.23E+08 | T | C | gefos2012bmd_femur | magic2012_homair | | −2.60119364 |

| CHR | SNP | N.bmd | Z.glucose | N.glucose | stat_SHom | stat_SHet | p_SHom |
|---|---|---|---|---|---|---|---|
| 3 | rs2124500 | 32961 | −4.86753294 | 58074 | 27.7161256 | 27.7161256 | 1.40E−07 |
| 3 | rs2124500 | 32961 | 1.59237709 | 51750 | 0.03741995 | 6.19521509 | 0.84661254 |
| 3 | rs2124500 | 32961 | −1.08844206 | 37037 | 4.9792234 | 4.9792234 | 0.0256535 |
| 3 | rs2124500 | 32961 | 3.56088993 | 36466 | 1.46238349 | 16.5471493 | 0.22655126 |
| 3 | rs2124500 | 32961 | −4.86753294 | 58074 | 33.2270523 | 33.2270523 | 8.20E−09 |
| 3 | rs2124500 | 32961 | 1.59237709 | 51750 | 0.12436856 | 10.1008618 | 0.7243439 |
| 3 | rs2124500 | 32961 | 3.56088993 | 36466 | 0.25989551 | 22.7053616 | 0.61019195 |
| 3 | rs2124500 | 32961 | −1.08844206 | 37037 | 8.48674041 | 10.1008618 | 0.00357744 |
| 3 | rs2877716 | 32961 | −4.62483318 | 58074 | 25.445902 | 25.445902 | 4.55E−07 |
| 3 | rs2877716 | 32961 | 1.44949283 | 51750 | 0.00695489 | 5.56048734 | 0.93353666 |
| 3 | rs2877716 | 32961 | −0.94982732 | 37037 | 4.47321139 | 4.48467742 | 0.03443022 |
| 3 | rs2877716 | 32961 | 3.1789688 | 36466 | 0.88107751 | 14.2267933 | 0.34790673 |
| 3 | rs2877716 | 32961 | −4.62483318 | 58074 | 30.8993395 | 30.8993395 | 2.72E−08 |
| 3 | rs2877716 | 32961 | 1.44949283 | 51750 | 0.22909869 | 10.1679897 | 0.63219294 |
| 3 | rs2877716 | 32961 | 3.1789688 | 36466 | 0.04796171 | 20.1521721 | 0.82664879 |
| 3 | rs2877716 | 32961 | −0.94982732 | 37037 | 7.93517026 | 10.1679897 | 0.00484831 |
| 3 | rs6798189 | 32961 | −4.60645076 | 58074 | 25.1892406 | 25.1892406 | 5.20E−07 |
| 3 | rs6798189 | 32961 | 1.55267834 | 51750 | 0.03276917 | 5.92698054 | 0.85634985 |
| 3 | rs6798189 | 32961 | −1.09869758 | 37037 | 4.89767946 | 4.89767946 | 0.02689281 |
| 3 | rs6798189 | 32961 | 3.40758705 | 36466 | 1.25823955 | 15.4295908 | 0.26198458 |
| 3 | rs6798189 | 32961 | −4.60645076 | 58074 | 30.4972312 | 30.4972312 | 3.34E−08 |
| 3 | rs6798189 | 32961 | 1.55267834 | 51750 | 0.13641303 | 9.9019916 | 0.71187331 |
| 3 | rs6798189 | 32961 | 3.40758705 | 36466 | 0.17392505 | 21.4405653 | 0.67664679 |
| 3 | rs6798189 | 32961 | −1.09869758 | 37037 | 8.41021786 | 9.9019916 | 0.00373118 |
| 3 | rs9883204 | 32961 | −4.86371974 | 58074 | 26.7978228 | 26.7978228 | 2.26E−07 |
| 3 | rs9883204 | 32961 | 1.60225153 | 51750 | 0.08734163 | 5.77866156 | 0.76758432 |
| 3 | rs9883204 | 32961 | −1.23132857 | 37037 | 4.93894737 | 4.93894737 | 0.02625802 |
| 3 | rs9883204 | 32961 | 3.46766568 | 36466 | 1.58038381 | 15.0712356 | 0.20870542 |
| 3 | rs9883204 | 32961 | −4.86371974 | 58074 | 31.6402306 | 31.6402306 | 1.86E−08 |
| 3 | rs9883204 | 32961 | 1.60225153 | 51750 | 0.03787603 | 8.53690462 | 0.84569229 |
| 3 | rs9883204 | 32961 | 3.46766568 | 36466 | 0.39599493 | 20.3218027 | 0.52916492 |
| 3 | rs9883204 | 32961 | −1.23132857 | 37037 | 8.03033428 | 8.39429726 | 0.00460003 |
| 3 | rs11717195 | 32961 | 5.39346966 | 58074 | 30.0357847 | 30.0357847 | 4.24E−08 |
| 3 | rs11717195 | 32961 | −1.68873617 | 51750 | 0.29321451 | 5.31015097 | 0.58816792 |
| 3 | rs11717195 | 32961 | −2.28181948 | 37037 | 0.37617199 | 7.83229743 | 0.53965908 |

TABLE 4-continued

Detailed CP-ASSOC results for all SNPs at the 3q21.1 locus. For each SNP, the association
Z scores for each trait and the resulting CP-ASSOC pleiotropy p-values are recorded.

| 3 | rs11717195 | 32961 | −4.19790129 | 36466 | 4.06311406 | 17.7072788 | 0.0438296 |
|---|---|---|---|---|---|---|---|
| 3 | rs11717195 | 32961 | 5.39346966 | 58074 | 38.1760986 | 38.1760986 | 6.46E−10 |
| 3 | rs11717195 | 32961 | −1.68873617 | 51750 | 0.05066203 | 9.60864595 | 0.82191527 |
| 3 | rs11717195 | 32961 | −4.19790129 | 36466 | 1.08473514 | 26.8188655 | 0.29764068 |
| 3 | rs11717195 | 32961 | −2.28181948 | 37037 | 0.11945114 | 14.2499207 | 0.72963054 |
| 3 | rs7613951 | 32961 | −5.19177378 | 58074 | 26.9963559 | 26.9963559 | 2.04E−07 |
| 3 | rs7613951 | 32961 | 1.63285261 | 51750 | 0.37910074 | 4.56369067 | 0.5380849 |
| 3 | rs7613951 | 32961 | −0.96189968 | 37037 | 2.74916057 | 2.74916057 | 0.0973055 |
| 3 | rs7613951 | 32961 | 2.98111598 | 36466 | 1.59588747 | 9.95855967 | 0.20648699 |
| 3 | rs7613951 | 32961 | −5.19177378 | 58074 | 33.250894 | 33.250894 | 8.10E−09 |
| 3 | rs7613951 | 32961 | 1.63285261 | 51750 | 0.00012127 | 7.76922366 | 0.9912137 |
| 3 | rs7613951 | 32961 | 2.98111598 | 36466 | 0.21789571 | 15.5973753 | 0.64064798 |
| 3 | rs7613951 | 32961 | −0.96189968 | 37037 | 5.94013597 | 6.76620835 | 0.01479988 |

TABLE 5

Associations discovered using the eLX and MTAG bivariate association tools. These follow the format
of Table 1 and detail the bivariate association replications using the eLX and MTAG tools.

| Method | Locus | SNP rs# | Chr | Pos (GRCh37) | Ancestral | Derived | Derived Allele Frequency | Singleton Density Score |
|---|---|---|---|---|---|---|---|---|
| eLX | MEF2C | rs1366594 | 5 | 88376061 | A | C | 0.48 | 142.72 |
| | GCKR | rs780094 | 2 | 27741237 | C | T | 0.41 | 212.82 |
| | | rs1260326 | 2 | 27730940 | C | T | 0.41 | 204.21 |
| | ADCY5 | rs11717195 | 3 | 123082398 | T | C | 0.18 | 74.46 |
| | EYA1 | rs980299 | 8 | 72094119 | T | C | 0.33 | 59.53 |
| | MEPE | rs6845452 | 4 | 88823007 | A | C | 0.46 | 238.24 |
| | CYP19A1 | rs10851498 | 15 | 51537012 | T | C | 0.45 | 211.90 |
| | | rs10459592 | 15 | 51536141 | T | G | 0.45 | 207.58 |
| | ADRA2A | rs17775480 | 10 | 112979082 | G | A | 0.08 | 109.73 |
| | CCDC170 | rs900195 | 6 | 151925377 | C | T | 0.38 | 69.05 |
| | PKDCC | rs988958 | 2 | 42287306 | G | A | 0.28 | 164.51 |
| | SUSD4 | rs17161988 | 1 | 223444263 | G | A | 0.42 | 143.59 |
| | IGF1 | rs2607988 | 12 | 102929883 | A | G | 0.17 | 120.60 |
| | C11orf49 | rs1872896 | 11 | 47160623 | C | T | 0.33 | 941.61 |
| | RUNX1 | rs2834999 | 21 | 36940444 | G | A | 0.03 | 193.96 |
| | SOX6 | rs1994214 | 11 | 15730356 | C | A | 0.48 | 117.03 |
| | RELA | rs11227247 | 11 | 65422853 | C | A | 0.12 | 142.15 |
| | DAG1 | rs3924462 | 3 | 49524236 | T | G | 0.43 | 496.95 |
| | APCDD1 | rs206447 | 18 | 10439986 | G | A | 0.34 | 57.43 |
| MTAG | MEF2C | rs1366594 | 5 | 88376061 | A | C | 0.4751 | C |
| | | rs10037512 | 5 | 88354675 | T | C | 0.4781 | C |
| | DAG1 | rs87938 | 3 | 41137672 | A | G | 0.5388 | G |
| | SUSD4 | rs12742784 | 1 | 22682366 | C | T | 0.1879 | C |
| | GCKR | rs780110 | 2 | 27685388 | G | A | 0.4165 | A |
| | EYA1 | rs980299 | 8 | 72094119 | T | C | 0.3131 | T |
| | | rs4103014 | 8 | 72089172 | C | A | 0.1829 | A |
| | SAMD12 | rs4130891 | 8 | 119921354 | G | A | 0.1402 | G |
| | C11orf49 | rs6485690 | 11 | 46798631 | A | G | 0.675 | A |
| | | rs1872896 | 11 | 47160623 | C | T | 0.6769 | C |
| | SOX6 | rs7935478 | 11 | 15733511 | C | T | 0.4354 | C |
| | | rs7130751 | 11 | 15737746 | C | T | 0.4354 | C |
| | ADCY5 | rs11717195 | 3 | 123082398 | T | C | 0.174 | T |
| | RELA | rs11227247 | 11 | 65422853 | A | C | 0.1252 | C |
| | APCDD1 | rs206447 | 18 | 10439986 | A | G | 0.328 | A |
| | | rs206441 | 18 | 10442221 | C | T | 0.2942 | C |
| | PKIA | rs11990002 | 8 | 79100584 | T | C | 0.4354 | G |
| | SLC25A16 | rs10998249 | 10 | 70286394 | C | A | 0.1054 | — |
| | GRB10 | rs6976501 | 7 | 50760220 | G | A | 0.7992 | G |
| | | rs7791286 | 7 | 50856792 | G | A | 0.825 | G |
| | TEX41 | rs13396091 | 2 | 146371961 | G | T | 0.3907 | T |
| | MACF1 | rs2275188 | 1 | 39748921 | G | A | 0.7167 | G |
| | | rs2275187 | 1 | 39763242 | G | A | 0.7197 | G |
| | APEH | rs4855881 | 3 | 49715446 | G | A | 0.5099 | G |
| | | rs11919311 | 3 | 49656789 | G | T | 0.503 | G |
| | | rs3924462 | 3 | 49524236 | T | G | 0.4334 | T |
| | | rs885592 | 3 | 49497883 | T | G | 0.4334 | T |
| | LGR4 | rs4514364 | 11 | 27456059 | C | T | 0.6789 | T |
| | FYCO1 | rs1873001 | 3 | 46032847 | C | T | 0.6561 | C |
| | PPP1CB | rs2045886 | 2 | 29010517 | A | G | 0.4851 | A |
| | AK097493 | rs2075411 | 19 | 32460790 | G | A | 0.4066 | g |
| | ZBTB20 | rs680947 | 3 | 114598529 | G | A | 0.9473 | A |

TABLE 5-continued

Associations discovered using the eLX and MTAG bivariate association tools. These follow the format
of Table 1 and detail the bivariate association replications usingthe eLX and MTAG tools.

| Method | Locus | SNP rs# | Chr | Pos (GRCh37) | Ancestral | Derived | Derived Allele Frequency | Singleton Density Score |
|---|---|---|---|---|---|---|---|---|
| | PTCH1 | rs4448343 | 9 | 98266370 | A | G | 0.3201 | G |
| | DIS3L2 | rs2679163 | 2 | 232816237 | G | T | 0.3907 | T |
| | BRWD1 | rs2836789 | 21 | 40338995 | C | T | 0.7078 | C |
| | PDGFC | rs10517655 | 4 | 157780909 | T | C | 0.1133 | T |
| | FAM53B | rs2362515 | 10 | 126336158 | G | A | 0.3191 | G |

TABLE 6

| Method | Locus | Bivariate P-value | Trait | Bone Traits (GEFOS) P-value | Effect | Trait | Glycemic Traits (MAGIC) P-value | Effect |
|---|---|---|---|---|---|---|---|---|
| eLX | MEF2C | 4.36E−30 | FNBMD | 5.11E−29 | 11.18 | FI | 8.72E−04 | 0.011 |
| | GCKR | 3.17E−10 | LSBMD | 3.11E−03 | −2.957 | FI | 3.40E−09 | −0.019 |
| | | 4.77E−08 | LSBMD | 1.82E−03 | −3.118 | HOMAIR | 9.15E−07 | −0.02 |
| | ADCY5 | 5.73E−09 | FNBMD | 1.99E−03 | 3.091 | FG | 6.93E−08 | 0.02 |
| | EYA1 | 9.57E−09 | FNBMD | 2.30E−07 | 5.173 | FG | 9.77E−04 | 0.012 |
| | MEPE | 1.10E−08 | FNBMD | 1.11E−07 | 5.307 | FI | 4.37E−03 | −0.009 |
| | CYP19A1 | 2.02E−08 | FNBMD | 4.14E−06 | −4.604 | HOMAIR | 2.02E−04 | 0.015 |
| | | 2.25E−07 | FNBMD | 1.98E−05 | −4.267 | FI | 5.19E−04 | 0.011 |
| | ADRA2A | 2.32E−08 | FNBMD | 2.53E−03 | −3.02 | HOMAB | 3.27E−07 | 0.03 |
| | | 3.00E−08 | LSBMD | 3.25E−03 | −2.943 | HOMAB | 3.27E−07 | 0.03 |
| | CCDC170 | 1.07E−07 | LSBMD | 1.94E−06 | 4.76 | FI | 2.06E−03 | −0.01 |
| | | 1.93E−07 | FNBMD | 4.39E−06 | 4.592 | FI | 2.06E−03 | −0.01 |
| | | 3.80E−07 | FNBMD | 4.39E−06 | 4.592 | HOMAIR | 4.30E−03 | −0.012 |
| | PKDCC | 1.20E−07 | FNBMD | 1.45E−06 | 4.818 | FI | 3.93E−03 | −0.01 |
| | SUSD4 | 2.12E−07 | FNBMD | 3.27E−05 | 4.154 | HOMAB | 2.36E−04 | −0.013 |
| | IGF1 | 2.43E−07 | LSBMD | 3.58E−03 | −2.913 | HOMAIR | 2.90E−06 | 0.025 |
| | C11orf49 | 4.37E−07 | FNBMD | 2.50E−05 | −4.215 | FG | 4.98E−04 | −0.013 |
| | | 8.44E−07 | LSBMD | 5.55E−05 | −4.031 | FG | 4.98E−04 | −0.013 |
| | RUNX1 | 4.56E−07 | LSBMD | 1.37E−05 | −4.349 | HOMAIR | 1.41E−03 | 0.032 |
| | SOX6 | 4.77E−07 | FNBMD | 5.24E−06 | −4.555 | FG | 2.82E−03 | −0.009 |
| | RELA | 5.98E−07 | LSBMD | 6.33E−06 | 4.515 | FG | 3.26E−03 | 0.016 |
| | DAG1 | 8.18E−07 | LSBMD | 4.74E−04 | −3.495 | HOMAIR | 6.64E−05 | −0.016 |
| | APCDD1 | 9.95E−07 | LSBMD | 4.10E−05 | −4.102 | FG | 8.14E−04 | −0.011 |
| MTAG | MEF2C | 1.24E−32 | FNBMD | 5.11E−29 | 11.18 | FI | 8.72E−04 | 0.011 |
| | | 1.84E−31 | FNBMD | 3.91E−28 | 10.998 | HOMAIR | 5.42E−03 | 0.011 |
| | | 2.34E−29 | FNBMD | 3.91E−28 | 10.998 | FG | 1.19E−03 | 0.01 |
| | DAG1 | 4.79E−19 | FNBMD | 2.77E−16 | −8.183 | HOMAIR | 9.54E−03 | −0.01 |
| | | 3.52E−11 | LSBMD | 5.38E−09 | −5.835 | HOMAIR | 9.54E−03 | −0.01 |
| | SUSD4 | 8.00E−19 | FNBMD | 1.28E−16 | 8.275 | FG | 2.04E−03 | 0.012 |
| | | 1.74E−16 | LSBMD | 1.17E−14 | 7.719 | FG | 2.04E−03 | 0.012 |
| | GCKR | 1.26E−15 | LSBMD | 2.25E−05 | 4.239 | FG | 1.42E−12 | 0.022 |
| | | 2.99E−08 | LSBMD | 2.25E−05 | 4.239 | FI | 9.74E−04 | 0.011 |
| | | 7.16E−08 | LSBMD | 2.25E−05 | 4.239 | HOMAIR | 1.94E−03 | 0.012 |
| | EYA1 | 1.76E−10 | FNBMD | 2.30E−07 | 5.173 | FG | 9.77E−04 | 0.012 |
| | | 3.43E−08 | FNBMD | 4.48E−06 | −4.588 | HOMAIR | 9.11E−03 | −0.015 |
| | SAMD12 | 1.15E−09 | LSBMD | 1.49E−07 | −5.254 | FI | 8.05E−03 | −0.012 |
| | | 3.09E−07 | FNBMD | 3.79E−05 | −4.12 | FI | 8.05E−03 | −0.012 |
| | C11orf49 | 1.73E−09 | FNBMD | 2.30E−07 | 5.173 | FG | 6.69E−03 | 0.009 |
| | | 3.61E−08 | LSBMD | 5.55E−05 | −4.031 | FG | 4.98E−04 | −0.013 |
| | SOX6 | 2.70E−09 | FNBMD | 6.56E−07 | 4.974 | FG | 4.16E−03 | 0.009 |
| | | 2.70E−09 | FNBMD | 6.98E−07 | 4.962 | FG | 3.95E−03 | 0.009 |
| | ADCY5 | 3.22E−09 | FNBMD | 1.99E−03 | 3.091 | FG | 6.93E−08 | 0.02 |
| | RELA | 2.81E−08 | LSBMD | 6.33E−06 | 4.515 | FG | 3.26E−03 | 0.016 |
| | APCDD1 | 4.25E−08 | LSBMD | 4.10E−05 | −4.102 | FG | 8.14E−04 | −0.011 |
| | | 2.33E−07 | FNBMD | 6.66E−05 | 3.988 | FG | 3.17E−03 | 0.01 |
| | PKIA | 5.80E−08 | FNBMD | 1.65E−05 | 4.308 | FI | 3.59E−03 | 0.009 |
| | SLC25A16 | 6.48E−08 | LSBMD | 2.36E−05 | −4.228 | FI | 2.18E−03 | −0.021 |
| | GRB10 | 1.24E−07 | FNBMD | 4.34E−03 | −2.852 | FG | 2.68E−06 | −0.017 |
| | | 9.68E−07 | LSBMD | 1.03E−03 | −3.281 | FG | 5.07E−04 | −0.014 |
| | TEX41 | 1.34E−07 | LSBMD | 9.03E−04 | 3.319 | FG | 6.05E−05 | 0.013 |
| | MACF1 | 1.61E−07 | LSBMD | 5.82E−05 | −4.02 | FI | 1.94E−03 | −0.012 |
| | | 3.04E−07 | LSBMD | 3.77E−05 | −4.121 | HOMAIR | 5.64E−03 | −0.012 |
| | | 2.09E−07 | LSBMD | 3.77E−05 | −4.121 | FG | 4.03E−03 | −0.01 |
| | APEH | 1.70E−07 | LSBMD | 2.35E−04 | 3.678 | FG | 4.79E−04 | 0.011 |
| | | 1.99E−07 | FNBMD | 2.31E−04 | 3.682 | FG | 6.38E−04 | 0.01 |
| | | 3.06E−07 | LSBMD | 4.74E−04 | −3.495 | HOMAIR | 6.64E−05 | −0.016 |
| | | 8.97E−07 | FNBMD | 9.23E−04 | −3.313 | HOMAIR | 7.78E−05 | −0.016 |

TABLE 6-continued

| | | Bivariate | | Bone Traits (GEFOS) | | | Glycemic Traits (MAGIC) | | |
|---|---|---|---|---|---|---|---|---|---|
| Method | Locus | P-value | Trait | P-value | Effect | Trait | P-value | Effect | |
| | LGR4 | 1.73E−07 | LSBMD | 2.51E−05 | −4.214 | fg | 4.89E−03 | −0.01 | |
| | FYCO1 | 2.29E−07 | LSBMD | 1.12E−04 | 3.862 | homab | 9.91E−04 | 0.012 | |
| | PPP1CB | 3.31E−07 | FNBMD | 1.11E−04 | 3.865 | fg | 2.60E−03 | 0.009 | |
| | AK097493 | 3.98E−07 | FNBMD | 2.15E−03 | 3.069 | fg | 5.30E−05 | 0.015 | |
| | ZBTB20 | 5.36E−07 | FNBMD | 1.63E−03 | 3.15 | fg | 1.23E−04 | 0.026 | |
| | PTCH1 | 6.73E−07 | LSBMD | 2.49E−04 | 3.663 | homab | 1.19E−03 | 0.011 | |
| | DIS3L2 | 7.01E−07 | LSBMD | 3.57E−03 | 2.914 | fg | 5.46E−05 | 0.013 | |
| | BRWD1 | 7.35E−07 | LSBMD | 1.65E−04 | −3.767 | fg | 3.ISE−03 | −0.01 | |
| | PDGFC | 8.74E−07 | FNBMD | 1.88E−04 | 3.734 | fi | 3.26E−03 | 0.016 | |
| | FAM53B | 9.73E−07 | FNBMD | 1.04E−04 | 3.881 | homab | 7.98E−03 | 0.01 | |

TABLE 7

Associations for all SNPs at the 3q21.1 locus tested by MTAG. Note that MTAGfilters to SNPs in HapMap3 and thus only these three SNPs were tested.

| SNP | CHR | Chr.position | Minor Allele Frequency | LDscore | Ancestral | Derived | Z.diabetes | P.diabetes |
|---|---|---|---|---|---|---|---|---|
| rs6798189 | 3 | 123095312 | 0.19525066 | 76.9177322 | G | A | −6.006 | 1.90E−09 |
| rs2877716 | 3 | 123094451 | 0.19525066 | 76.9177322 | T | C | 5.904 | 3.55E−09 |
| rs11717195 | 3 | 123082398 | 0.18205805 | 74.4630764 | T | C | −6 | 1.97E−09 |

| SNP | Z.bone | P.bone | mtag_beta | mtag_se | mtag_z | mtag_pval |
|---|---|---|---|---|---|---|
| rs6798189 | −3.66 | 0.00025123 | −0.0217436 | 0.00375821 | −5.7856275 | 7.22E−09 |
| rs2877716 | 3.67 | 0.00024255 | 0.02160015 | 0.00375821 | 5.74745704 | 9.06E−09 |
| rs11717195 | −3.7 | 0.0002156 | −0.022452 | 0.00386048 | −5.8158597 | 6.03E−09 |

TABLE 8

| SNP | equal_h2_beta | equal_h2_se | equal_h2_z | equal_h2_pval | dLX_OB | dLX_OB.Pval |
|---|---|---|---|---|---|---|
| rs6798189 | −0.0171846 | 0.00253578 | −6.7768528 | 1.23E−11 | −6.681033 | 2.37E−11 |
| rs2877716 | 0.01699396 | 0.00253578 | 6.70166646 | 2.06E−11 | 6.616759 | 3.67E−11 |
| rs11717195 | −0.0176969 | 0.00260479 | −6.7939991 | 1.09E−11 | −6.70384 | 2.03E−11 |

| SNP | dLC | dLC.Pval | SHom | SHet | p_SHom | p_SHet |
|---|---|---|---|---|---|---|
| rs6798189 | 47.520732 | 4.80E−11 | 23.2716157 | 23.2716157 | 1.41E−06 | ###### |
| rs2877716 | 46.399417 | 8.40E−11 | 4.81659848 | 23.4484258 | 0.02818692 | ###### |
| rs11717195 | 47.716355 | 4.35E−11 | 4.01303562 | 29.089515 | 0.04514979 | ###### |

Figures 2A, 2B:
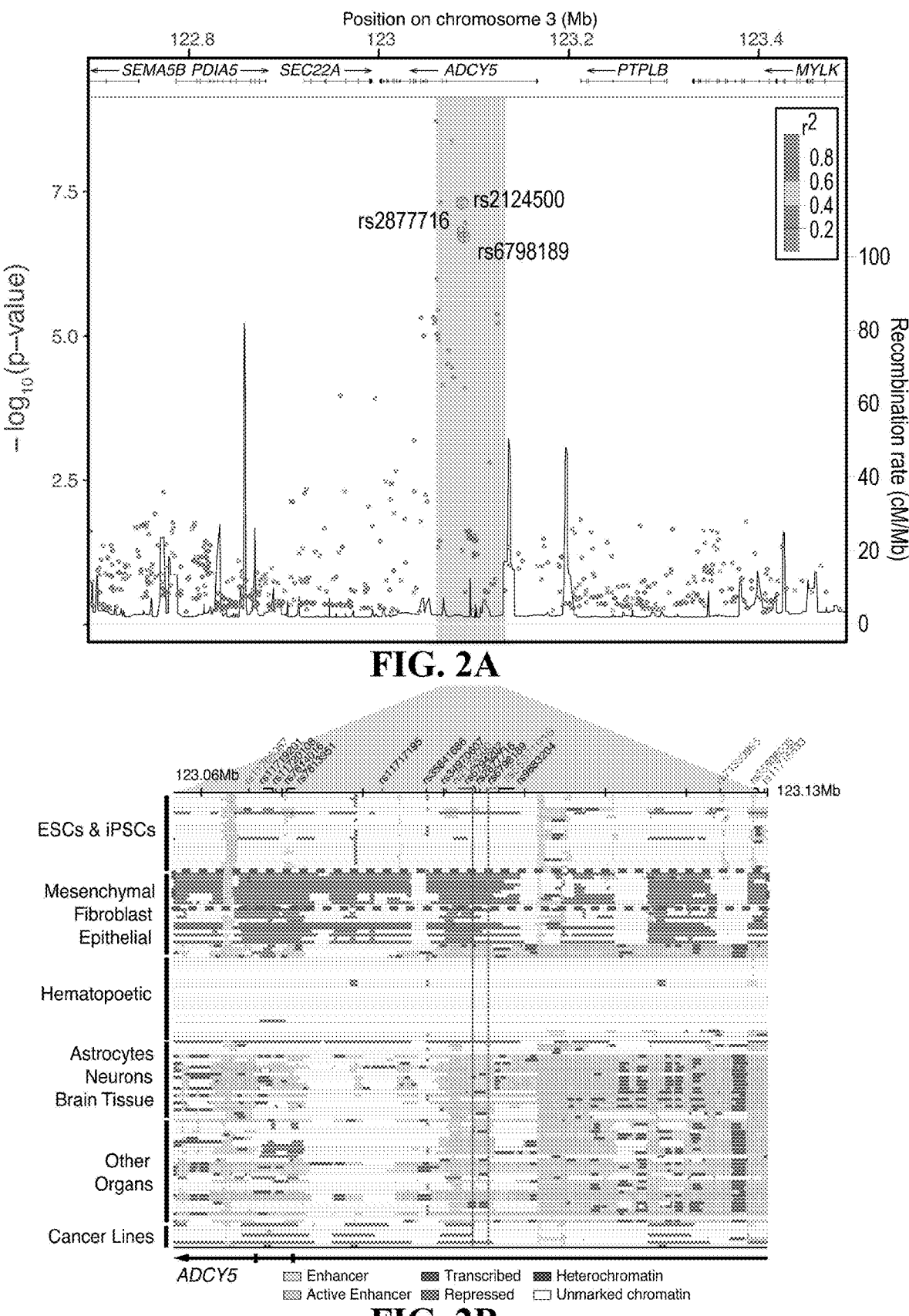
FIG. 2A-2B—The 3q21.1 locus is associated with bone mineral density and fasting glucose levels. (2A) Genetic association with FNBMD and fasting glucose levels for ADCY5 locus variants. Bivariate association (y-axis) and genomic coordinates (x-axis) for all common single nucleotide polymorphisms (SNPs; circles) in a 100 kb window of chromosome 3 centered on the ADCY5 bivariate locus. The region of association localizes to a >65 kb interval in intronic regions of the ADCY5 gene containing 13 variants in high linkage disequilibrium (LD) in Europeans (1000 Genomes r2) with the bivariate tag SNP rs2124500. SNPs that meet bivariate criteria are marked by bolded dots. (2B) Chromatin state annotations for the 65 kb-long-long bivariate locus. Genomic intervals are shown across 127 human cell types and tissues reference epigenomes profiled by the Roadmap Epigenomics projects, based on a 25-state chromatin state model (see FIG. 1) learned from 12 epigenomic marks using imputed signal tracks at 25-nucleotide resolution. Chromatin states considered here include Polycomb repressed states (H3K27me3), weak enhancers (H3K4me1 only), strong enhancers (also H3K27ac), and transcribed enhancers (also H3K36me3). Polycomb-repressed segments in mesenchymal cells are denoted with a dotted box. The tagSNP rs2124500, the predicted causal variant rs56371916 and 11 other variants in high LD with rs2124500 are indicated.

Example 2—Haplotypes at 3q21.1 Differ in Chromatin Accessibility and Regulatory Activity The 3q21.1 locus is contained entirely within the 95 kb-long first intron of ADCY5, spanning 65 kb and harboring a set of 13 non-coding SNPs in strong LD (r2>0.8, 1000 G Phase 1 EUR), (FIG. 2A). These 13 variants (referred to here as the candidate regulatory variants) define two alternative haplotypes: the ancestral haplotype 1 (frequency 77% in European individuals), associated with higher FNBMD and higher fasting glucose levels, and haplotype 2 (frequency 23%), associated with lower FNBMD and lower fasting glucose levels.

Figure 1C:
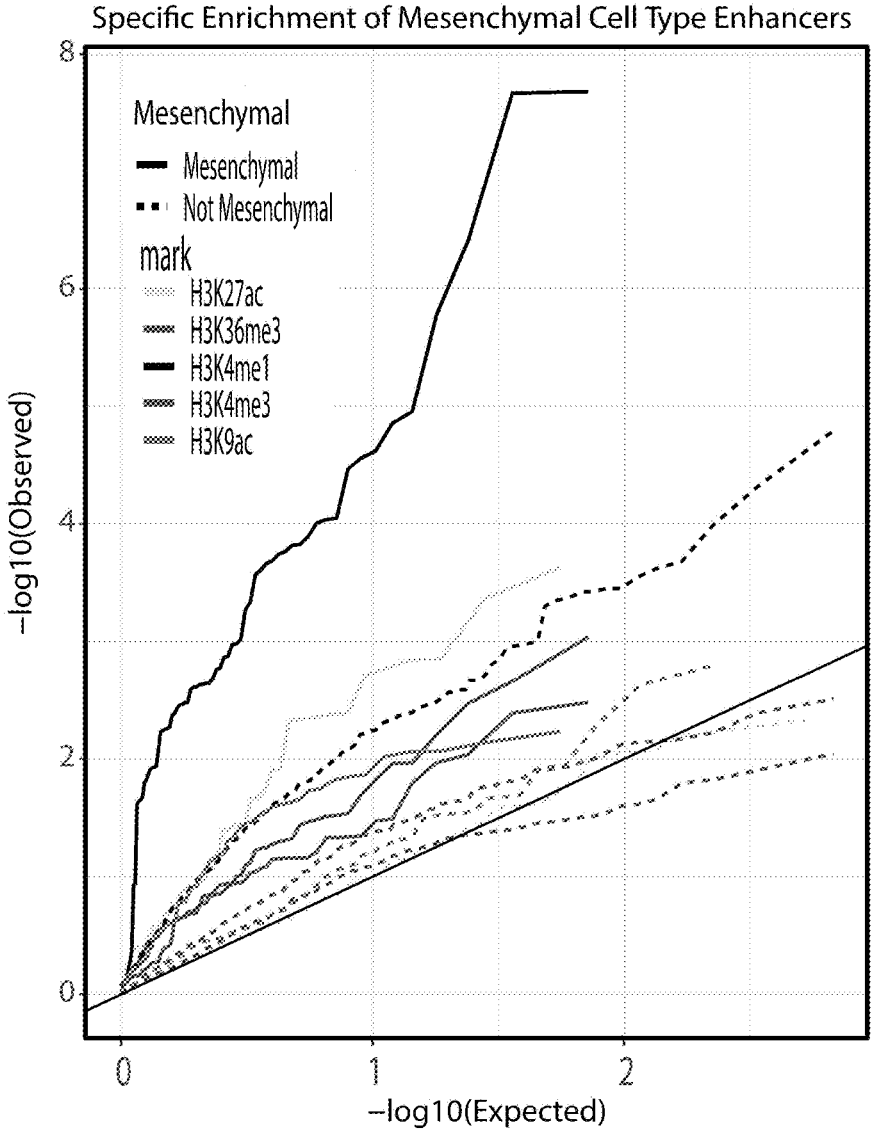

To identify the cell types in which the causal variant(s) may act, Applicants further examined chromatin state maps of the 3q21.1 locus across 127 human cell types (FIGS. 1B, 1D, 2B). The data revealed that the entire locus was spanned by Polycomb-repressed chromatin (marked by H3K27me3) in mesenchymal lineages, while it was unmarked or active in non-mesenchymal cell types. Among the mesenchymal lineages, Applicants focused on adipocytes, osteoblasts, and mesenchymal stem cell (MSC) precursors (which can give rise to adipocytes, osteoblasts, myocytes, and chondrocytes, FIG. 3A); these cell types had among the highest levels of enrichment for Polycomb-repressed chromatin (FIG. 4A).

Figure 1E:
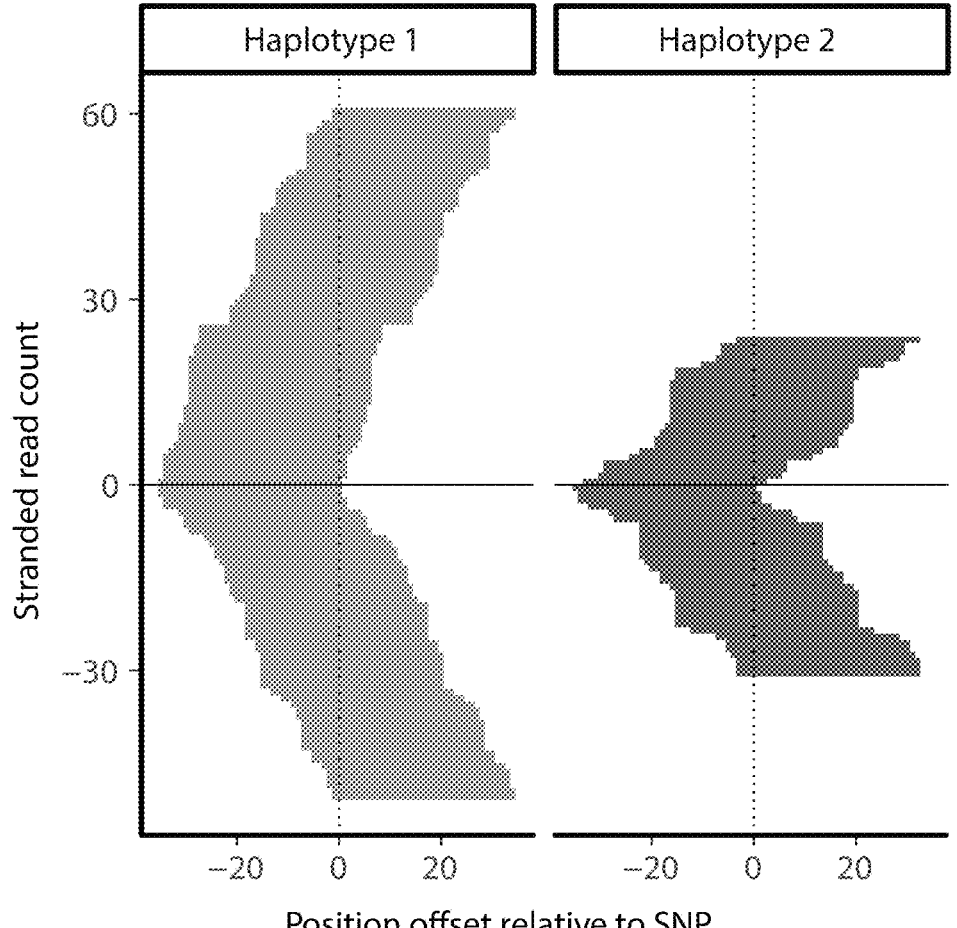

Applicants examined whether the two haplotypes show differences in chromatin structure during adipocyte differentiation. Specifically, Applicants performed assays for Polycomb repression (H3K27me3-seq) and chromatin accessibility (ATAC-seq) on adipose-derived mesenchymal stem cells (AMSCs) from a heterozygous individual across a time course of differentiation (before induction (Day 0), early differentiation (Day 2), and terminal differentiation (Day14)) and compared the numbers of reads from the two haplotypes. The two haplotypes showed no significant differences with respect to Polycomb repression (FIG. 4B, left), but a striking difference in chromatin accessibility, with haplotype 1 being enriched by roughly 1.9-fold at all time points (FIG. 4B, right, Table 9). A similar increase in chromatin accessibility of haplotype 1 is also evident in published DNaseI hypersensitivity data in mesenchymal precursor cells in skeletal muscle-derived MSCs (FIG. 1E) (Maurano et al. 2015). Consistent with recent studies showing that polycomb repression can co-occur with chromatin accessibility (Scharer et al. 2018; Muerdter et al. 2018), these results indicate that haplotype 1 is associated with a poised state, while haplotype 2 is associated with a repressed state.

TABLE 9

Allelic bias through differentiation in ATAC-seq read counts. Replicates
were combined to calculate an allelic ratio and a p-value corresponding
to a binomial test against equal read counts per allele.

| Assay | Time point | Haplotype 1 Reads (rep 1) | Haplotype 1 Reads (rep 2) | Haplotype 2 Reads (rep 1) | Haplotype 2 Reads (rep 2) | Allelic Ratio | P-value |
|---|---|---|---|---|---|---|---|
| ATAC-seq | Day 0 | 25 | 18 | 9 | 14 | 1.87 | 0.02 |
| ATAC-seq | Day 2 | 26 | 18 | 10 | 14 | 1.83 | 0.021 |
| ATAC-seq | Day 14 | 12 | 25 | 4 | 15 | 1.95 | 0.02 |
| H3K27me3 ChIP-seq | Day 0 | 76 | 60 | 82 | 52 | 1.01 | 0.95 |
| H3K27me3 ChIP-seq | Day 2 | 87 | 59 | 53 | 68 | 1.21 | 0.46 |
| H3K27me3 ChIP-seq | Day 14 | 73 | 73 | 56 | 84 | 1.04 | 0.31 |

Further, Applicants functionally tested the two haplotypes for differences in regulatory activity, using plasmid-based luciferase-reporter assays in osteoblasts and adipocytes. Analysis of a 10 kb region containing the 10 candidate regulatory SNPs in tightest LD with rs2124500 (r2>0.9) showed that haplotype 1 had 1.9-fold and 1.8-fold greater transcriptional activity in osteoblasts and adipocytes, respectively. In contrast, Applicants saw no haplotype-specific regulatory differences in hepatocytes, lymphocytes, differentiated muscle cells or pancreatic beta cells (FIG. 4C).

Example 3—Regulatory Region Targets ADCY5

Figures 4D, 4E, 4F, 4G:
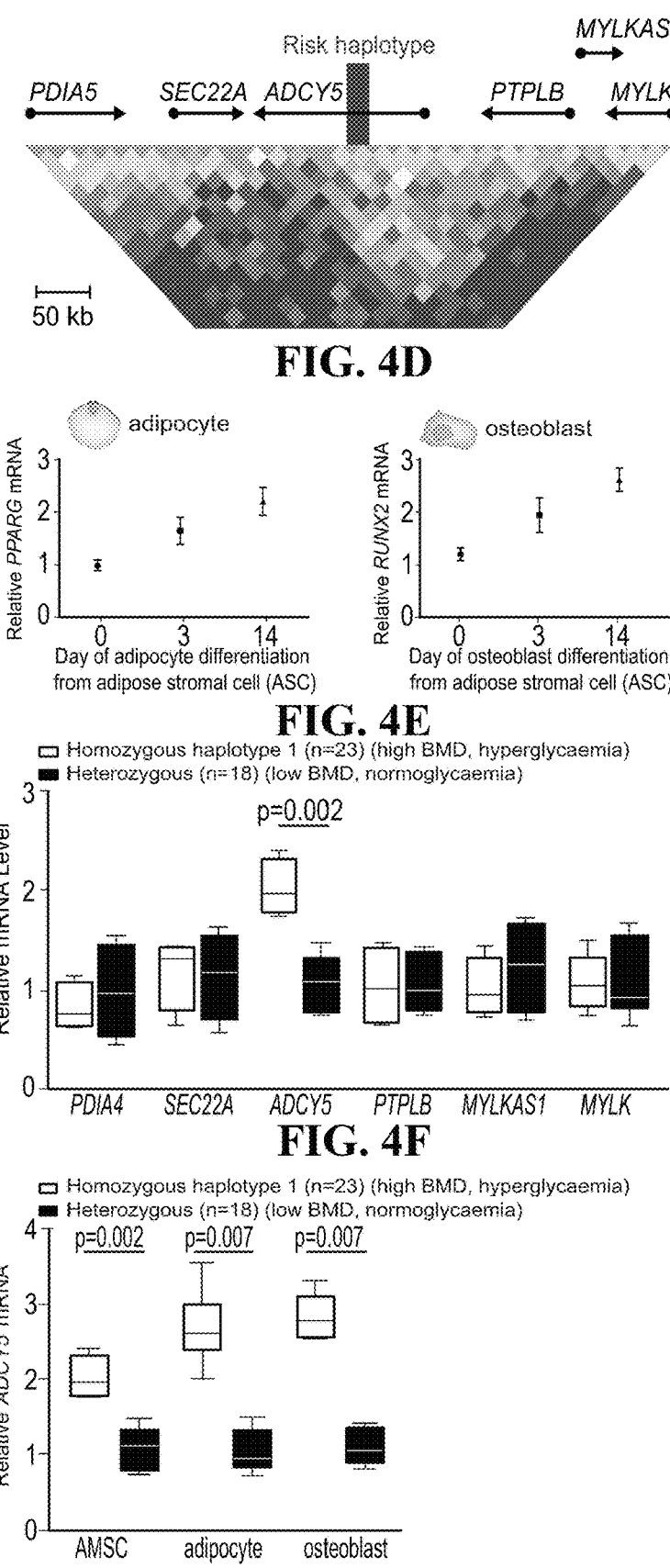

To identify potential regulatory target(s) of the locus, Applicants examined three-dimensional genome folding maps from Hi-C assays in embryonic stem cell-derived MSCs (Dixon et al. 2015). The locus lies in a well-defined 300-kb contact domain containing only two genes: ADCY5 and PTPLB (FIG. 4D). In their assessment, Applicants considered the six genes within a larger 1 Mb region centered on the locus (PDIA5, SEC22A, ADCY5, PTPLB, MYLKAS1, and MYLK).

Figure 3B:
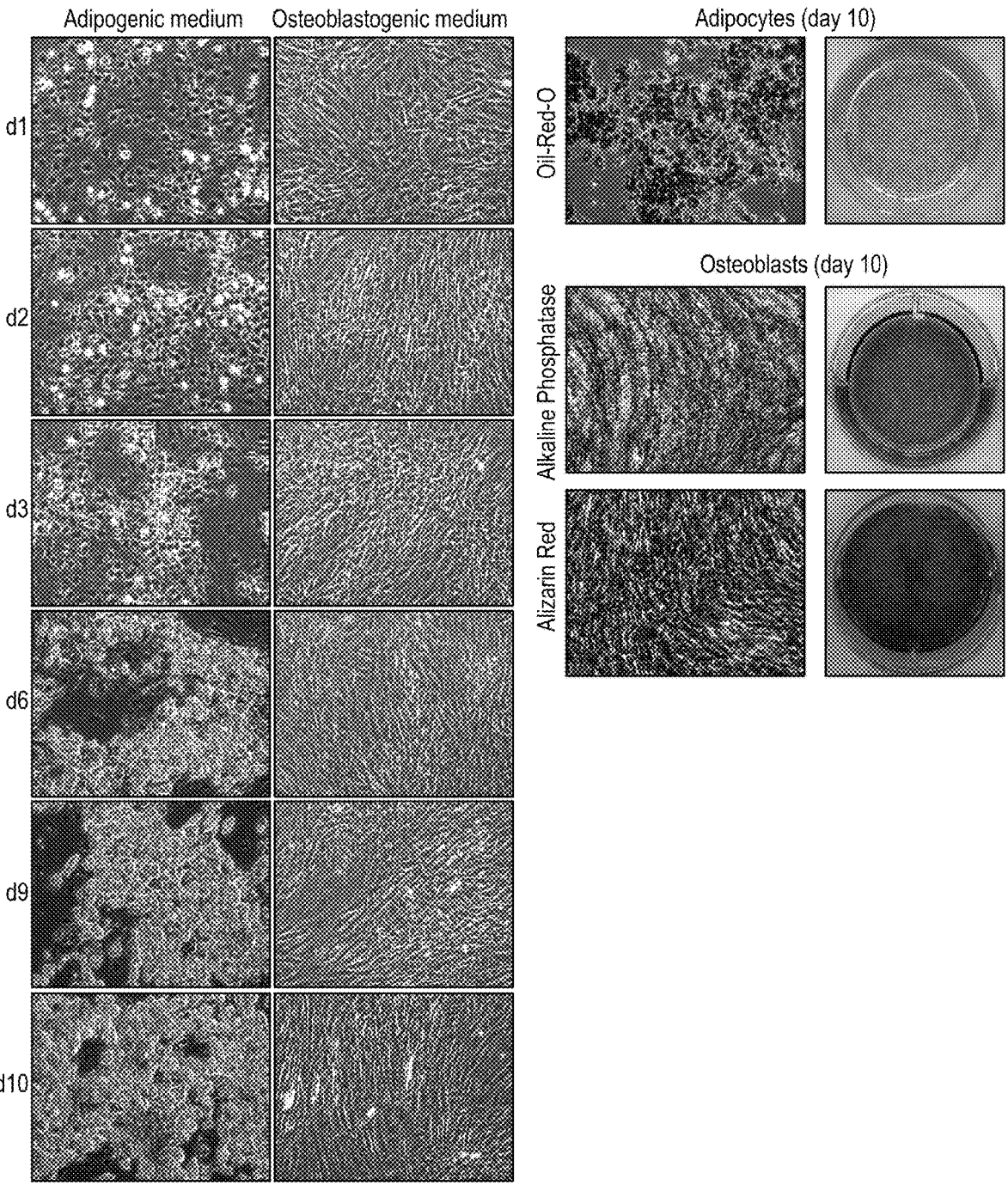

Applicants isolated AMSCs from 41 normal-weight individuals, comprising 18 heterozygous individuals (haplotypes 1/2) and 23 homozygous individuals (haplotypes 1/1) (Cohort 1, see Methods). These AMSCs were then differentiated into mature osteoblasts and adipocytes, as confirmed by marker-gene expression, bright field microscopy, and colorimetric assays (FIG. 4E, Tables 10 and 11, FIG. 3B). Among the six genes, only ADCY5 showed haplotype-specific differences in gene expression (FIG. 4F), with haplotype 1 being associated with 2.7-fold higher expression in both adipocytes and osteoblasts (p=0.007, FIG. 4G). These results implicate ADCY5 as the likely regulatory target of the 3q21.1 locus.

TABLE 10

Relative mRNA levels in AMSCs differentiated
to osteoblasts (n = 5)

| Marker Gene | Diff day 0 | Diff day 6 | Diff day 14 |
|---|---|---|---|
| RUNX2 | 1.1 ± 0.03 | 1.6 ± 0.09 | 3.4 ± 0.08 |
| OCN | 1.1 ± 0.12 | 1.0 ± 0.15 | 2.9 ± 0.38 |
| OSX | 1.0 ± 0.01 | 1.3 ± 0.07 | 2.2 ± 0.08 |

TABLE 11

Relative mRNA levels in AMSCs differentiated
to adipocytes (n = 5)

| Marker Gene | Diff day 0 | Diff day 6 | Diff day 14 |
|---|---|---|---|
| CEBPA | 0.9 ± 01 | 3.1 ± 0.03 | 3.2 ± 0.2 |
| PPARG | 1.1 ± 0.07 | 2.8 ± 0.15 | 3.5 ± 0.05 |
| ADIPOQ | 1.0 ± 0.2 | 1.3 ± 0.07 | 5.2 ± 0.2 |

Figure 5B:
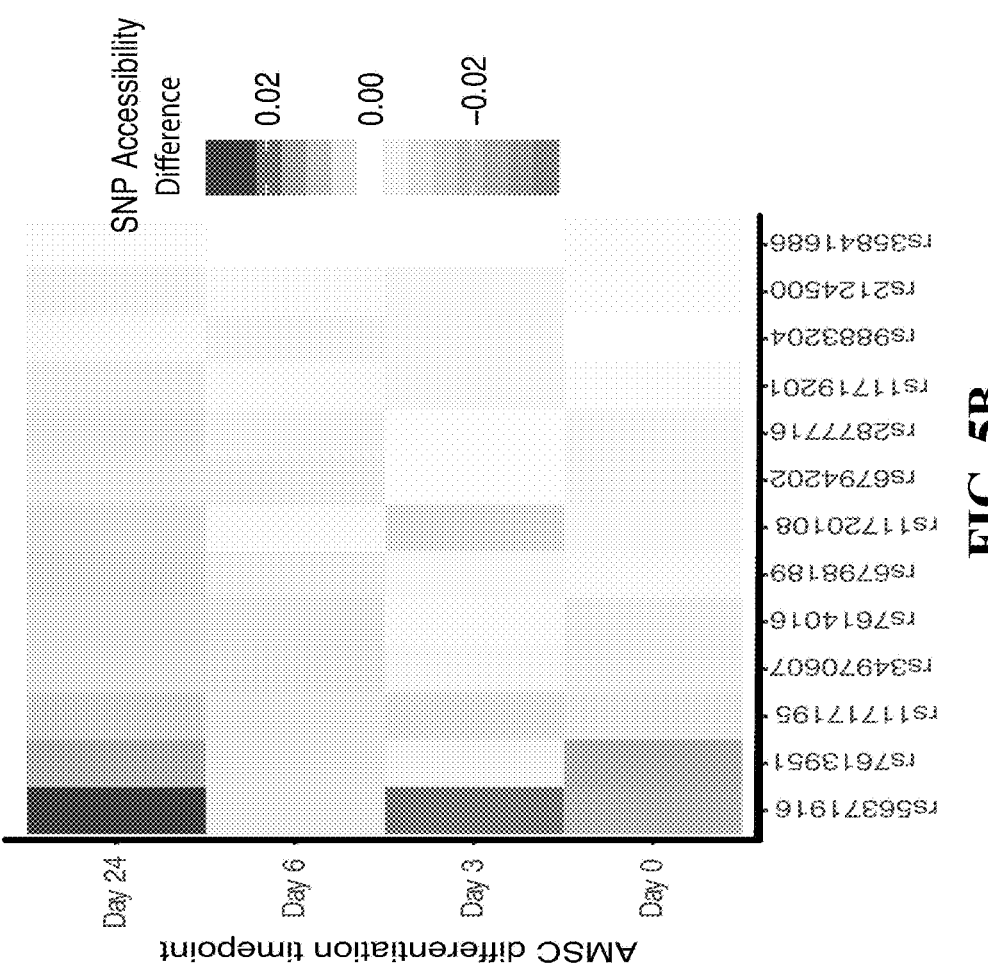
FIG. 5A-5B—Computational methods predict rs56371916 as a likely causal variant at the 3q21.1 locus. (5A) Phylogenetic conservation analysis and deep-based prediction of chromatin accessibility for 13 highly correlated SNPs at the 3q21.1 locus. X axis: Phylogenetic conservation scores of jointly conserved motifs using PMCA (Claussnitzer et al. 2014). PMCA was used to identify orthologous regions in 21 vertebrate species and to scan the 120 bp sequence context around each variant in high LD with rs2124500 for groups of transcription factor binding site motifs whose order and distance range is cross-species conserved. The scores have a minimum of 0 (no conserved motif modules), with scores indicating the count of non-overlapping jointly conserved transcription factor binding site motifs whose relative positions within the window are conserved. Y axis: for groups of transcription factor binding site motifs whose order and distance range is cross-species conserved. The scores have a minimum of 0 (no conserved motif modules), with scores indicating the count of non-overlapping jointly conserved transcription factor binding site motifs whose relative positions within the window are conserved. Y axis: Predicted relative change in chromatin accessibility (SNP accessibility difference SAD scores) in adipocytes for each SNP comparing alleles on each SNP comparing alleles on haplotype 1 and haplotype 2. A deep CNN Basset (Kelley et al. 2016) was trained on genome-wide ATAC-seq data assayed in AMSC-derived mature adipocytes. Alleles were assigned to each SNP in high LD with rs2124500 and evaluated for predicted accessibility using Basset, in which more positive numbers indicate more predicted accessibility on the alternative allele compared to the reference allele. Both PMCA and Basset highlight rs56371916 as the likely causal variant at the 3q21.1 locus, and predict that rs56371916 T allele increases chromatin accessibility. (5B) Time course of predicted SAD scores throughout differentiation of AMSC into mature adipocytes for all 13 highly correlated SNPs using Basset. AMSCs were differentiated and ATAC-seq was performed at days 0, 3, 6, and 24 of differentiation. Basset was trained on a 20 bp window within open chromatin regions jointly for the four timepoints. Accessibility of the haplotype 1 and haplotype 2 was inferred by centering the SNP under 30 bp window with both haplotypes and taking the difference of the predicted probabilities as a measure of effect.
Figure 5A:
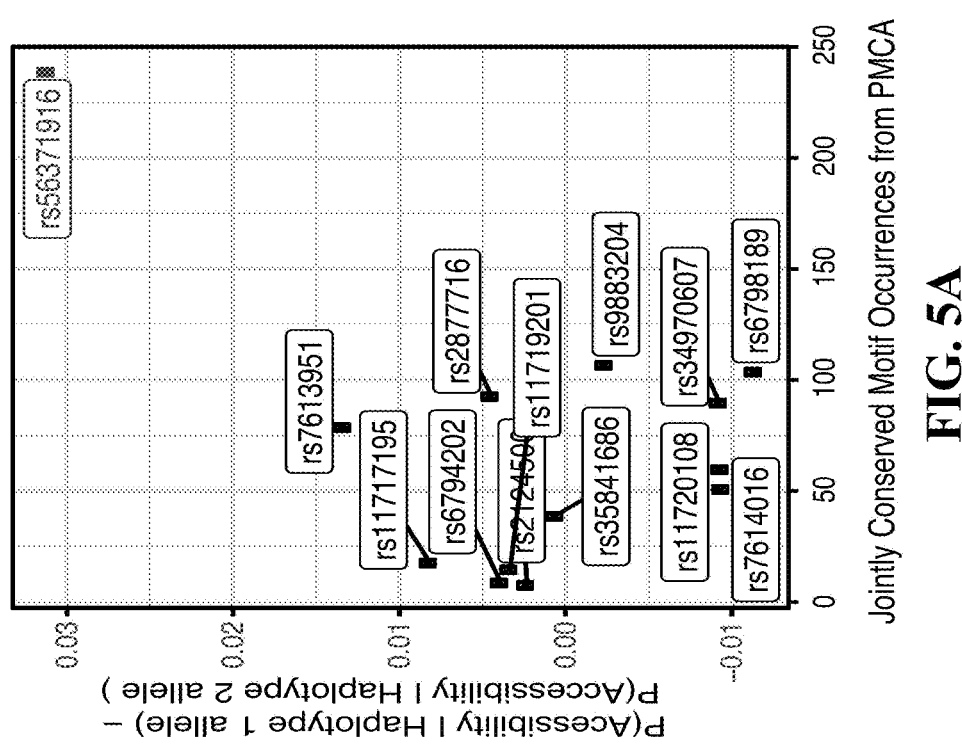

Example 4—Computational Analysis Implicates Rs56371916 as the Likely Causal Variants Applicants next sought to identify which of the 13 candidate regulatory variants was likely to be responsible for the differential expression of ADCY5. Applicants used two orthogonal computational approaches to prioritize variants; both highlighted the same SNP, rs56371916. The first method, Phylogenetic Module Complexity Analysis (PMCA) (Claussnitzer et al. 2014) looks for groups of at least three transcription factor binding motifs within a 120 bp-region that show good evolutionary conservation of sequence, order and distance (in human and at least one other vertebrate species). One variant, rs56371916, stood out as showing the highest score (Table 12, FIG. 5A). The second method, Basset (Kelley et al. 2016), uses a sequence-based deep convolutional neural network (CNN) approach to predict effects of non-coding variants, by training on the sequence content of genomic regions strongly enriched for a given epigenomic mark in a tissue or cell type of interest. After training on genome-wide chromatin accessibility (ATAC-Seq) data across a time-course of immortalized AMSC differentiation (before induction (D0), early differentiation (D3), advanced differentiation (D6), and terminal differentiation (D24)), the Basset method identified rs56371916 as being associated with the highest difference in chromatin accessibility between the alleles (Table 12, FIG. 5A), with the T allele on haplotype 1 increasing chromatin accessibility relative to the C allele on haplotype 2 in fully differentiated adipocytes (FIG. 5B, FIG. 6A). The allelic difference was in the 99th percentile for all SNPs in the GWAS catalog (MacArthur et al. 2017) (empirical p-value=0.0061) (FIG. 3B). A third method commonly used for variant prioritization, deltaSVM (Lee et al. 2015), also highlighted the same SNP in mesenchymal cells (Table 13).

TABLE 12

Prioritization of the variants at the 3q21.1 locus using PMCA and
Basset. Motif conservation and accessibility predictions were used.

| snp | $r^2$ with rs2124500 | PMCA conservation score number of jointly conserved motif occurrences | estimated p-value | Basset accessibility score (trained on ATAC-seq data in AMSC (day 24)) p(accessible \| haplotype 1 allele) | p(accessible \| haplotype 2 allele) | p(accessible \| haplotype 1 allele) − p(accessible \| haplotype 2 allele) |
|---|---|---|---|---|---|---|
| rs6794202 | 0.98 | 0 | 1 | 0.22201 | 0.2181 | 0.00391 |
| rs9883204 | 0.97 | 67 | 0.0536 | 0.2132 | 0.21558 | −0.00238 |
| rs2124500 | 1 | 2 | 0.0013 | 0.2131 | 0.21543 | 0.00233 |
| rs11720108 | 0.84 | 40 | 0.0002 | 0.18567 | 0.19503 | −0.00936 |
| rs11719201 | 0.84 | 10 | 0.001 | 0.21545 | 0.2121 | 0.00334 |
| rs35841686 | 0.96 | 24 | 0.0016 | 0.22071 | 0.22016 | −0.00056 |
| rs11717195 | 0.87 | 12 | 0.0002 | 0.20349 | 0.19531 | 0.00818 |
| rs7614016 | 0.86 | 44 | <0.0001 | 0.21623 | 0.22565 | −0.00942 |
| rs34970607 | 0.96 | 52 | <0.0001 | 0.20129 | 0.21054 | −0.00925 |
| rs7613951 | 0.86 | 54 | <0.0001 | 0.19648 | 0.18315 | 0.01333 |
| rs2877716 | 0.98 | 67 | <0.0001 | 0.217 | 0.22147 | 0.00447 |
| rs6798189 | 0.98 | 72 | <0.0001 | 0.19747 | 0.20886 | −0.01139 |
| rs56371916 | 0.98 | 189 | <0.0001 | 0.19873 | 0.16755 | 0.03118 |

TABLE 13

Estimated effect sizes of the extended 3q21.1 haplotype
using deltaSVM. Permutations are computed by shuffling
nucleotides in the 21bp window centered on the SNP.

| SNP | largestEffect | NumTissues | Permuta-tionsMean | Permutat-ionsMax |
|---|---|---|---|---|
| rs71330995_G_A | −2.87271 | 11 | 1209 | 748 |
| rs34970607_G_A | 21.3527 | 11 | 2019 | 53 |
| rs11715633_G_A | −2.25558 | 11 | 1234 | 1054 |
| rs6794202_C_T | −12.8069 | 11 | 874 | 122 |
| rs2877716_T_C | −8.75267 | 11 | 965 | 537 |
| rs11720108_C_T | −14.7495 | 11 | 743 | 642 |
| rs9883204_T_C | −14.3762 | 11 | 741 | 334 |
| rs34642857_T_C | −15.4117 | 11 | 828 | 46 |
| rs17361324_C_T | 3.72534 | 11 | 1519 | 2116 |
| rs7614016_G_A | −10.507 | 11 | 875 | 655 |
| rs6798189_G_A | 13.7421 | 11 | 1895 | 281 |
| rs56371916_T_C | 17.9303 | 11 | 1966 | 70 |
| rs72964564_A_C | −27.1141 | 11 | 549 | 23 |
| rs11708067_A_G | −1.17336 | 11 | 1299 | 1228 |
| rs10934647_C_T | 20.3032 | 11 | 2051 | 211 |
| rs11719201_C_T | 7.16918 | 11 | 1667 | 1032 |
| rs35606005_C_T | −36.732 | 11 | 308 | 15 |
| rs7613951_C_T | 14.5136 | 11 | 1913 | 252 |
| rs35841686_T_A | −3.67856 | 11 | 1156 | 1065 |
| rs11717195_T_C | 10.5904 | 11 | 1780 | 287 |
| rs2124500_T_C | −3.04982 | 11 | 1205 | 1007 |

Example 5—SNP Rs56371916 Affects an SREBP1 Binding Site

Figure 7A:
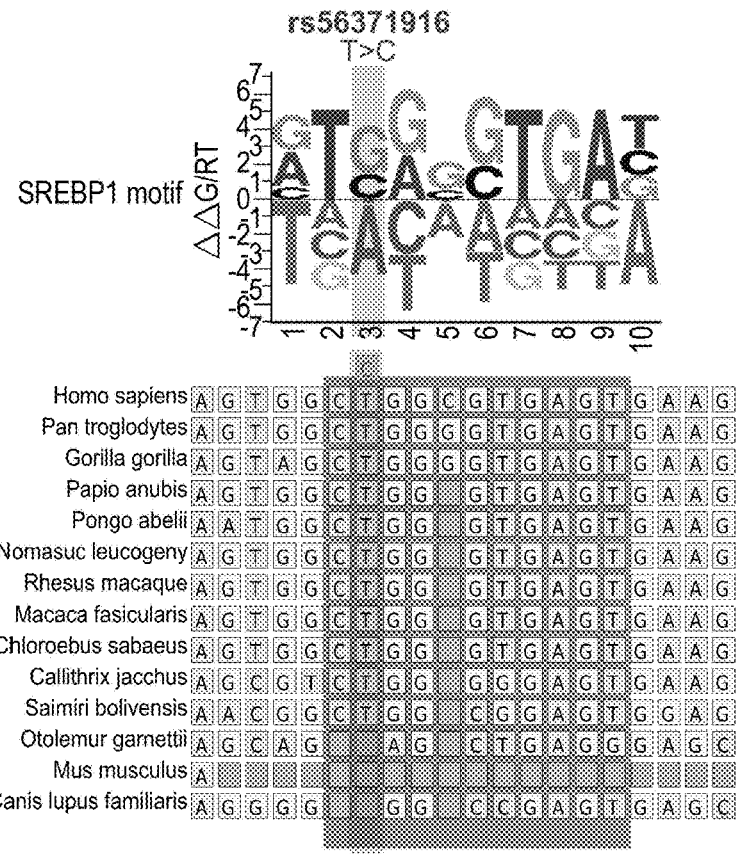
FIG. 7A-7G—rs56371916 alters an SREBP1 binding site. (7A) rs56371916 occurs within a canonical binding site for sterol-response element binding protein 1 (SREBP1) activator within a highly conserved cis-regulatory module (CRM) predicted by PMCA. UCSC multi-way multiz alignment to hg38 at UCSC (Blanchette et al. 2004) was used to define orthologous regions in different species. Each region's sequence was extracted and these were aligned to each other using CLUSTAL W. TF positions were selected based on matches of the given motifs to the hg38 sequence. (7B) and (7C) rs56371916 nucleotide importance on predicted chromatin accessibility during adipocyte differentiation (day 0, before differentiation and day 24, terminal differentiation) highlights SREBP1 as the likely binding regulator. The CNN-based-based method Basset predicts the change in accessibility resulting from mutation at every position to each alternative nucleotide, which highlights the individual nucleotides most critical to a sequence's activity. In silico mutagenesis produces heatmaps that display the change in predicted accessibility for any of the four possible nucleotides. The loss score measures the largest possible decrease while the gain score measures the largest possible increase for mutation to any other non-reference nucleotide at a given position. At day 0 of AMSC differentiation, the rs56371916 T allele, carried on haplotype 1, has little effect and there is no substantial predicted change in accessibility. By day 24, however, the accessibility has increased substantially with the rs56371916 T allele, carried on haplotype 1 as the most critical nucleotide for 20 bp sequence accessibility in terminally differentiated AMSC. Changes at rs56371916 are likely to reduce this accessibility, particularly if the T allele is changed to C, carried on haplotype 2 (Panel B). (7B) This is consistent with the overlapping SREBP1 motif, which is conserved across species. The alternate C allele, carried on haplotype 2, decreases accessibility by disrupting a SREBP1 motif. The region of potential accessibility gain is centered on the SREBP1 motif, and specifically includes the T allele present in the ancestral state (7C). (7D) Electrophoretic mobility shift assays (EMSA) for 40 bp oligonucleotides centered on rs56371916 using MC3T3 osteoblast (upper panel) and AMSC-derived adipocytes (lower panel) nuclear extract at different stages of differentiation (day 0, day 4, day 7, day 10). (7E) Electrophoretic mobility shift assays (EMSA) for 40 bp oligonucleotides centered on rs56371916 using MC3T3 osteoblast (upper panel) and AMSC-derived adipocytes (lower panel) nuclear extract at different stages of differentiation (day 0, day 4, day 7, day 10) (7E). Average affinity of highest affinity T allele sequence of length 8 (tggcgtga) and highest affinity C allele sequence (cacgccgg; reverse complemented) overlapping rs56371916 within a +/−1 kb region. The peak associated with a strong binding to the reference allele is clearly visible, and the difference between the two alleles was determined to be highly significant according to Intragenomic Replicate Method (IGR, two-tailed t-test p=$10^{-5.66}$; fold change in affinity ~1.903; (Cowper-Sal-lari et al. 2012). A total of 1073 instances for the T allele and 2142 instances for the C allele were averaged to create the profiles. (7F) and (7G). ADCY5 gene expression in primary differentiating osteoblasts treated with siRNAs targeting SREBP1 (siSREBP1, Panel F), EZH2 (siEZH2, 7G) or non-targeting control siRNAs (siNT). Bar plots depict relative gene expression+SD using HPRT for normalization. Assays were performed in cells from 18 heterozygous individuals (haplotypes 1/2) and 23 homozygous individuals (haplotypes 1/1) at day 3 of osteoblast differentiation.
Figure 7B:
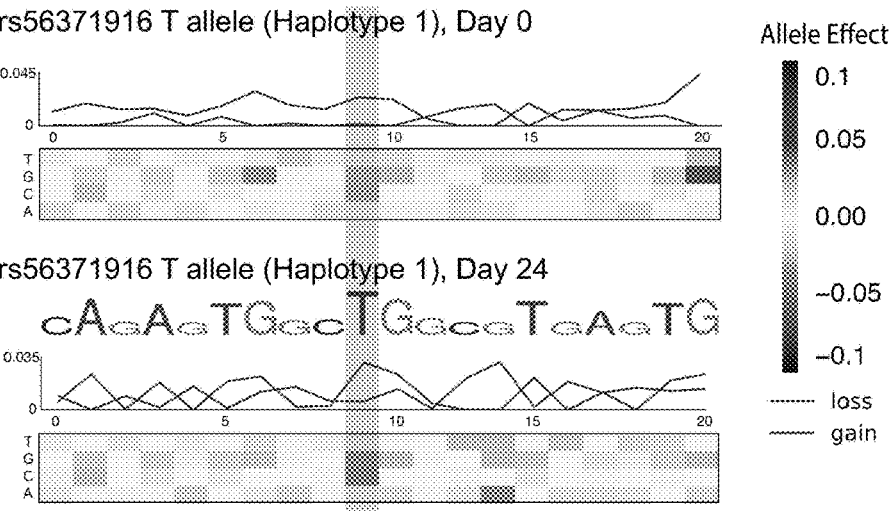
Figure 7C:
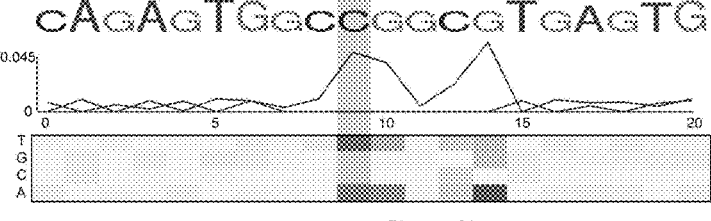
Figure 7D:
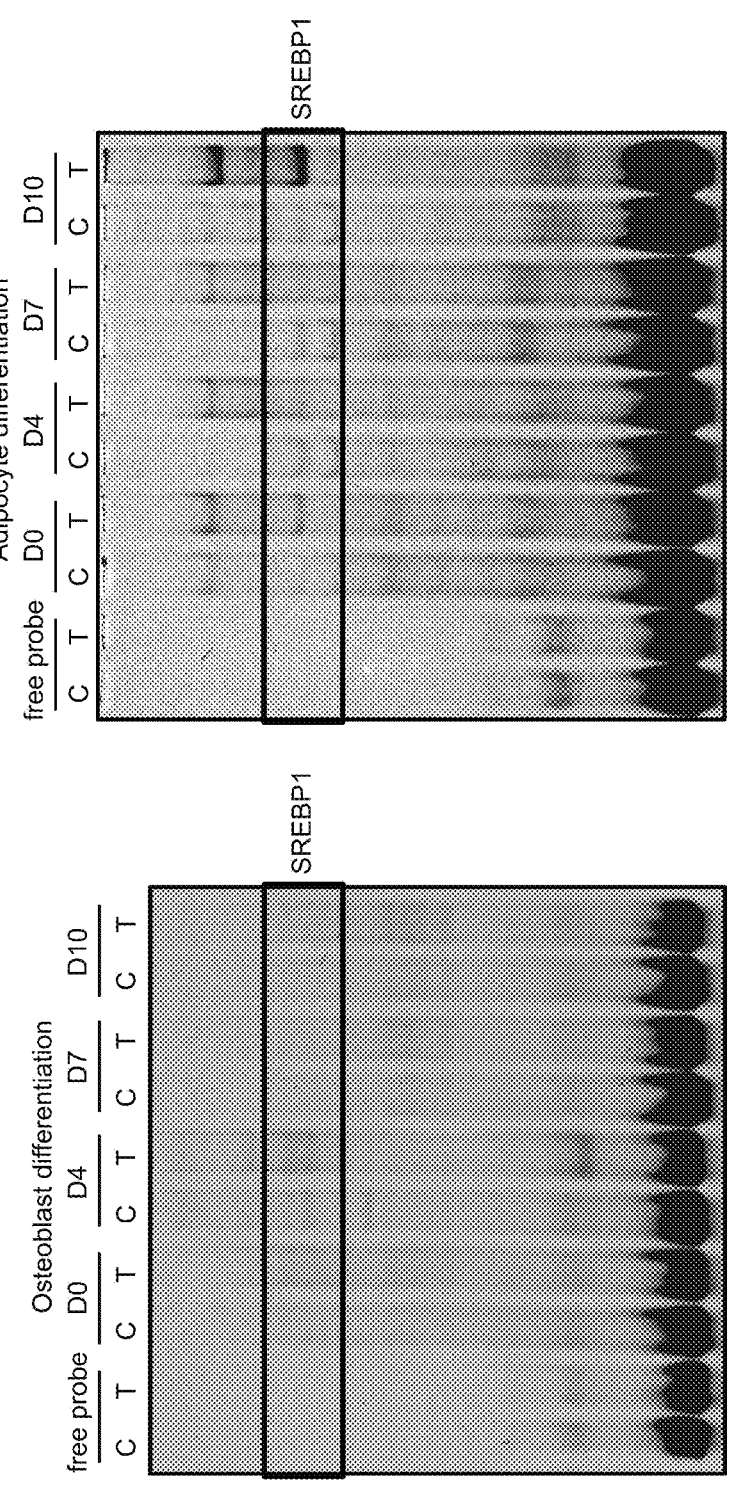

To identify the regulatory elements in the neighborhood of rs56371916, Applicants used the Basset CNN model to analyze the effect of altering each base within a 20 bp window centered on the SNP. Applicants found that rs56371916 itself was predicted to have the greatest effect, with the T-to-C substitution predicted to disrupt a highly conserved second position in an SREBP motif in fully differentiated adipocytes (Weirauch et al. 2014) (FIG. 7A-C).

SREBPs are transcription factors known to play a role in cholesterol and fatty acid biosynthesis. Because SREBPs are known to play activating roles (Edwards 2000), Applicants tested whether the C allele at rs56371916 decreased expression in their luciferase assay. Applicants found that it indeed decreased enhancer activity by 2.3-fold in both SGBS adipocytes (Fischer-Posovszky et al. 2007) (a frequently used in vitro pre-adipocyte model originated from adipose tissue from a patient with Simpson-Golabi-Behmel syndrome (SGBS)) (SGBS)) and MC3T3 osteoblasts (FIG. 6C, See Methods). Using electrophoretic mobility shift assays (EMSAs), Applicants also found that rs56371916 affected protein binding to the surrounding DNA sequence, with the C allele showing decreased protein binding (FIG. 7E), consistent with its disruption of the predicted SREBP motif. Moreover, protein-binding to the DNA sequence could be out-competed by an excess of probe containing a consensus binding sequence for SREBP (FIG. 6D). To confirm differential binding of SREBP1 to the T allele, Applicants used the IGR method (Cowper-Sal-lari et al. 2012) which compares the frequency of k-mers matching the rs56371916 T allele versus the C allele, based on publicly available SREBP1 ChIP-seq data, to estimate preferential binding affinity of SREBP1. Applicants confirmed that SREBP1 preferentially binds to the T allele with ~1.9-fold higher frequency (two-tailed t-test $p<2.2\times10^{-6}$) (FIG. 7E).

Figure 6B:
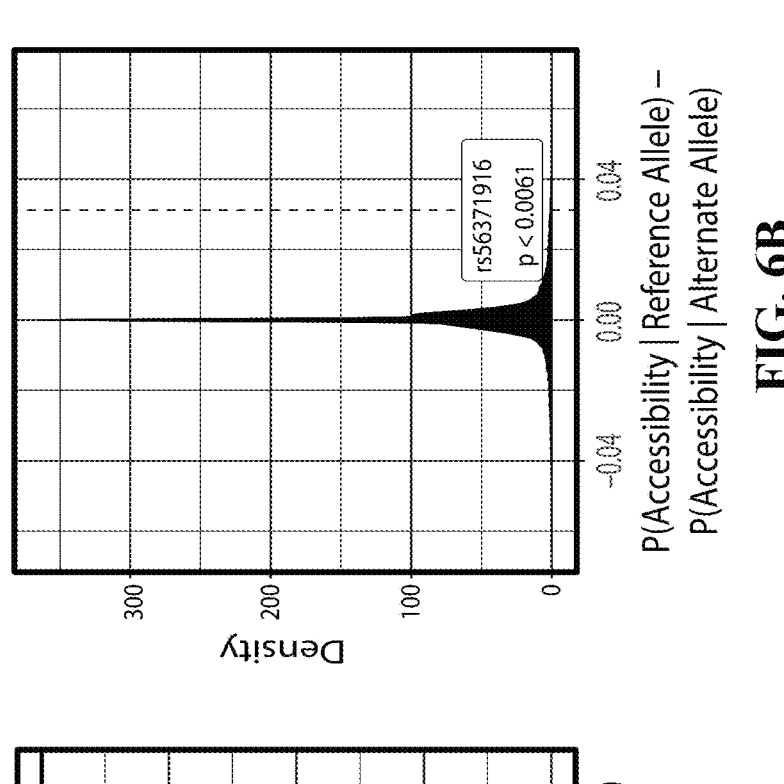
Figure 6A:
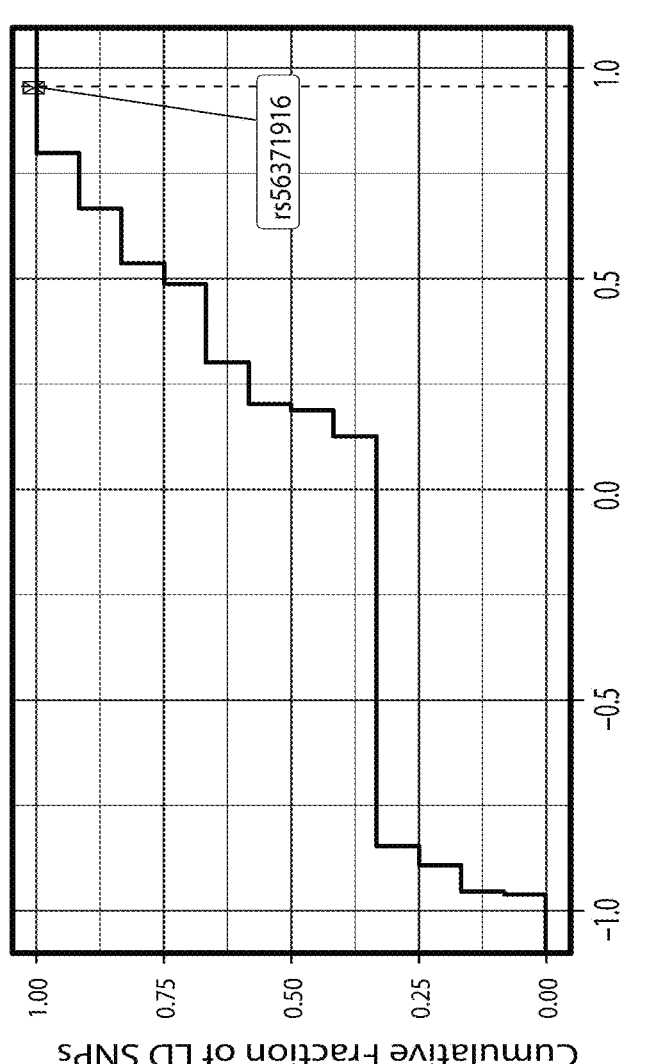
Figures 6C, 6D, 6E, 6F:
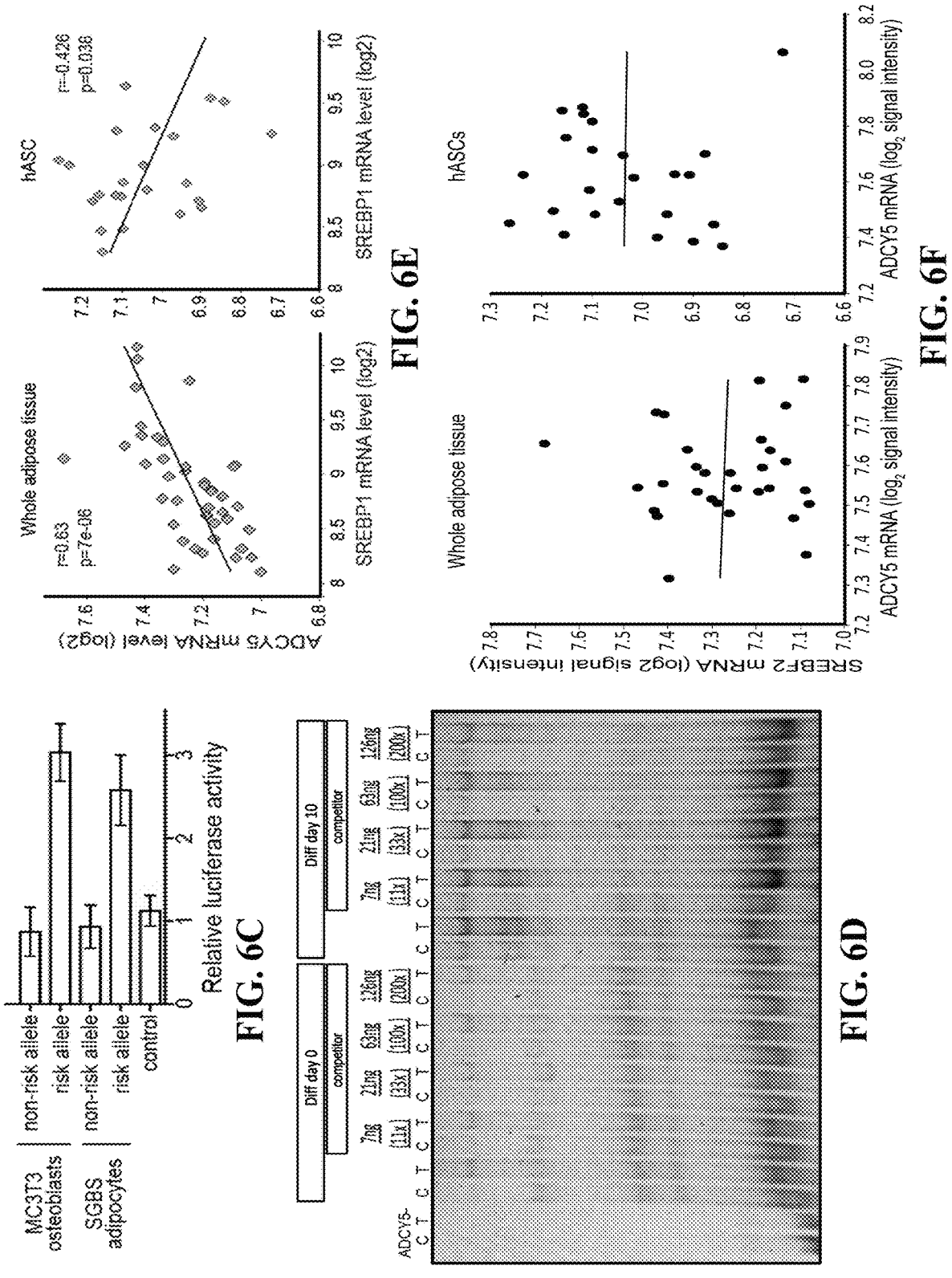
Figure 7E:
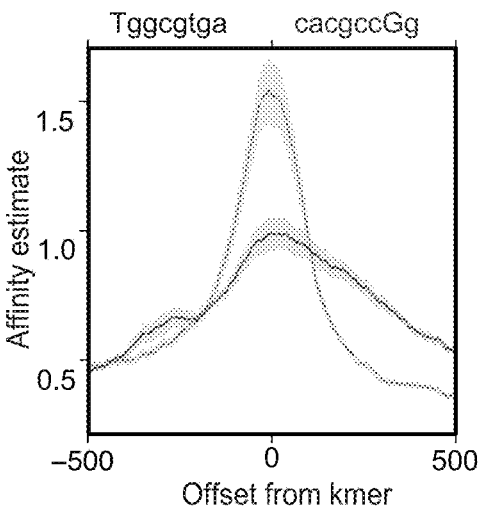

Of the two mammalian sterol regulatory element binding proteins, SREBP1 showed high expression levels in differentiated mesenchymal cells (FIG. 6E-G). Expression of ADCY5 was positively correlated with expression of SREBP1 in subcutaneous adipose tissue harboring differentiated adipocytes from 30 individuals (r=0.567, p=0.001), but not in adipocyte progenitor cells from 24 individuals (FIG. 6E, Cohort 2, see Methods). SREBP2 showed no correlation (FIG. 3F). ADCY5 and SREBP1 both showed increased expression over the course of adipocyte differentiation, while SREBP2 expression decreased (FIG. 3G yellow background). These results indicate that the relevant activating protein in adipocytes is SREBP1.

Figure 7F:
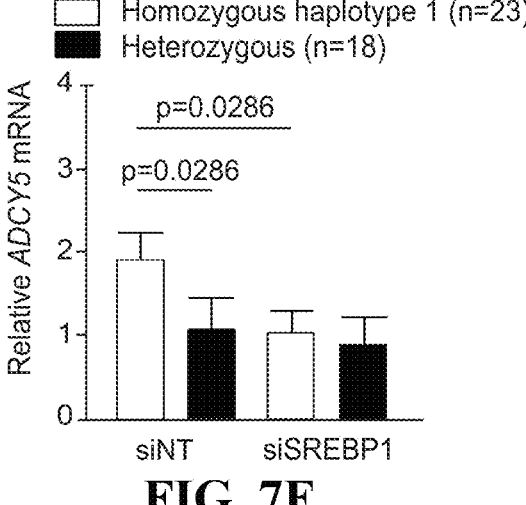

Applicants examined the effect of siRNA-mediated knockdown of SREBP1 on ADCY5 gene expression in the 41 cell lines from Cohort 1, consisting of 23 haplotype 1/1 homozygotes and 18 haplotype 1/2 heterozygotes. Consistent with the notion that SREBP1 binds the T allele more strongly than the C allele, Applicants found that SREBP1 knockdown had greater effects on ADCY5 expression in haplotype 1/1 homozygotes than haplotype 1/2 heterozygotes in both primary adipocytes (mean fold-decrease of 1.5±0.1 [[s.e.m.].] vs. 1.2±0.1)) and osteoblasts (1.9±0.1 vs. 1.1±0.2) (FIG. 7F). These data indicate an activating effect of SREBP1 binding to the major T allele on haplotype 1.

Figure 7G:
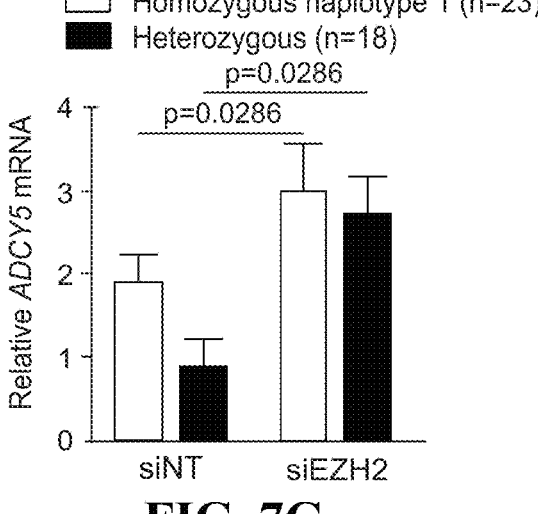

In addition to studying the effect of knocking down SREBP1 on ADCY5 expression, Applicants also examined the effect of depleting EZH2, the enzyme that catalyzes H3K27-trimethylation. Applicants found that siRNA-mediated knockdown of EZH2 increased ADCY5 expression by ~3-fold for haplotype 1/2 heterozygotes (p=0.02) and ~1.6 fold for haplotype 1 homozygotes (p=0.02) (FIG. 7G). This confirms that both haplotypes are under some degree of polycomb repression, with greater repression of haplotype 2 (FIG. 6H).

Example 6—SNP Rs56371916 and ADCY5 Expression are Associated with Changes in Lipid Oxidation in Primary Human Adipocytes and Osteoblasts To identify cellular processes affected by altered ADCY5 expression in adipocytes and osteoblasts, Applicants identified co-regulated genes in genome-wide expression data from primary human AMSCs in a cohort of 12 healthy, non-obese individuals (Cohort 3; see Methods). The co-expressed genes were highly enriched in biological processes related to fatty acid metabolism, including fatty acid oxidation and lipolysis (Table 14), suggesting that ADCY5 might play a role in lipid oxidation processes. Positively co-regulated genes include regulators of fatty acid oxidation—including the alcohol dehydrogenases ADH1A and ADH1B; the fatty acid transporters CPT2 and SLC27A2; the acyl-CoA dehydrogenase ACADM; the acetyl-CoA acetyltransferase enzyme ACAT1; and the fatty acid oxidation enzymes HADH and HADHB (Tables 15 and 16). Additional co-regulated genes encoded the rate-limiting enzyme of lipolysis LIPE and the lipid droplet-associated protein PLIN1. Applicants also noted several co-expressed genes relevant to bone, including SOD1, KLF15, ZNF74, ZNF133 and ZNF485, which are all involved in osteoblast differentiation and/or bone-related functions (Table 15). The gene with the strongest negative correlation with ADCY5 expression levels was LIF, a well-known inhibitor of osteoblast differentiation (Falconi and Aubin 2007).

TABLE 14

Enriched gene ontology (GO) terms for ADCY5 co-expressed mRNAs in human adipose stromal cells (hASC) isolated from 12 healthy non-obese patients (Pearson's r > 0.7).

| GO term (Pathways, humanmine.org accessed May 29, 2018) | Enrichment p-value | # matches | % of co-expressed genes |
|---|---|---|---|
| Co-expressed (203 recognized genes) | | | |
| Fatty acid metabolism | 0.001 | 7 | 3.4 |
| Valine, leucine and isoleucine degradation | 0.027 | 6 | 3.0 |
| Beta oxidation of octanoyl-CoA to hexanoyl-CoA | 0.035 | 3 | 1.5 |

* P-values are Holm-Bonferroni corrected

TABLE 15

Selected mRNAs correlated with ADCY5 mRNA in human adipose stromal cells (hASC) and mature adipocytes isolated from 12 healthy non-obese patients.

| Gene | Probe ID | ID | Definition | Pearson's r hASC | Adipocytes |
|---|---|---|---|---|---|
| Co-expressed with ADCY5 (Fatty acid metabolism) | | | | | |
| ACADM | ILMN_2053679 | 34 | acyl-Coenzyme A dehydrogenase, C-4 to C-12 straight chain (ACADM), nuclear gene encoding mitochondrial protein | 0.764 | 0.288 |
| ACAT1 | ILMN_1800008 | 38 | acetyl-Coenzyme A acetyltransferase 1 (acetoacetyl Coenzyme A thiolase) (ACAT1), nuclear gene encoding mitochondrial protein | 0.756 | 0.380 |
| ADH1A | ILMN_1764309 | 124 | alcohol dehydrogenase 1A (class I), alpha polypeptide (ADH1A) | 0.862 | 0.096 |
| ADH1B | ILMN_1811598 | 125 | alcohol dehydrogenase IB (class I), beta polypeptide (ADH1B) | 0.718 | 0.208 |
| CPT2 | ILMN_1678579 | 1376 | carnitine palmitoyltransferase II (CPT2), nuclear gene encoding mitochondrial protein | 0.761 | 0.061 |
| HADH | ILMN_1719906 | 3033 | hydroxyacyl-Coenzyme A dehydrogenase (HADH), nuclear gene encoding mitochondrial protein | 0.796 | 0.137 |
| HADHB | ILMN_2197846 | 3032 | hydroxyacyl-Coenzyme A dehydrogenase/3-ketoacyl-Coenzyme A thiolase/enoyl-Coenzyme A hydratase (trifunctional protein), beta subunit (HADHB), nuclear gene encoding mitochondrial protein | 0.707 | −0.211 |
| Fatty acid metabolism (marker genes) | | | | | |
| ACACA | ILMN_1772123 | 31 | acetyl-Coenzyme A carboxylase alpha (ACACA), transcript variant 2 | 0.426 | 0.151 |
| ACACB | ILMN_1763852 | 32 | acetyl-Coenzyme A carboxylase beta (ACACB) | 0.475 | 0.597 |
| ADFP/PLIN2 | ILMN_1801077 | 123 | adipose differentiation-related protein (ADFP) | 0.207 | 0.409 |
| ADIPOQ | ILMN_1775045 | 9370 | adiponectin, C1Q and collagen domain containing (ADIPOQ) | 0.677 | 0.497 |
| CD36 | ILMN_1665132 | 948 | CD36 molecule (thrombospondin receptor) (CD36), transcript variant 2 | 0.444 | 0.185 |
| CEBPA | ILMN_1715715 | 1050 | CCAAT/enhancer binding protein (C/EBP), alpha (CEBPA) | 0.571 | 0.012 |
| LIPE | ILMN_1670693 | 3991 | lipase, hormone-sensitive (LIPE) | 0.556 | 0.234 |
| MGLL | ILMN_1707310 | 11343 | monoglyceride lipase (MGLL), transcript variant 2 | 0.275 | 0.339 |

TABLE 15-continued

Selected mRNAs correlated with ADCY5 mRNA in human adipose stromal cells
(hASC) and mature adipocytes isolated from 12 healthy non-obese patients.

| Gene | Probe ID | ID | Definition | hASC | Adipocytes |
|---|---|---|---|---|---|
| | | | Gene | Pearson's r | |
| PLIN | ILMN_1665562 | 5346 | perilipin (PLIN) | 0.607 | 0.557 |
| PNPLA2 | ILMN_1787923 | 57104 | patatin-like phospholipase domain containing 2 (PNPLA2) | 0.321 | 0.421 |
| PPARG | ILMN_1800225 | 5468 | peroxisome proliferator-activated receptor gamma (PPARG), transcript variant 2 | 0.694 | 0.210 |
| SLC27A1 | ILMN_1787718 | 376497 | solute carrier family 27 (fatty acid transporter), member 1 (SLC27A1) | 0.143 | 0.513 |
| | | | Osteoblast differentiation and function (marker genes) | | |
| KLF15 | ILMN_1683133 | 28999 | Kruppel-like factor 15 (KLF15) | 0.761 | 0.179 |
| LIF | ILMN_1738725 | 3976 | leukemia inhibitory factor (cholinergic differentiation factor) (LIF) | −0.854 | −0.235 |
| OCX/SP7 | ILMN_1689461 | 121340 | Sp7 transcription factor (SP7) | −0.089 | 0.229 |
| OSN/BGLAP | ILMN_1755818 | 632 | bone gamma-carboxyglutamate (gla) protein (osteocalcin) (BGLAP) | 0.070 | −0.156 |
| RUNX2 | ILMN_2377746 | 860 | runt-related transcription factor 2 (RUNX2), transcript variant 2 | −0.487 | −0.463 |
| ZNF26 | ILMN_1691798 | 7574 | zinc finger protein 26 (ZNF26) | −0.713 | −0.062 |
| ZNF74 | ILMN_2383871 | 7625 | zinc finger protein 74 (ZNF74) | 0.640 | 0.302 |
| ZNF133 | ILMN_2174081 | 7692 | zinc finger protein 133 (ZNF133) | 0.750 | 0.336 |
| ZNF319 | ILMN_1711361 | 57567 | zinc finger protein 319 (ZNF319) | 0.799 | 0.149 |
| ZNF485 | ILMN_1664034 | 220992 | zinc finger protein 485 (ZNF485) | 0.710 | 0.013 |
| | | | | 1 | −1 |

Applicants next assessed whether rs56371916, which is associated with expression levels of ADCY5, is also associated with expression of the putative ADCY5-regulated genes involved in lipolysis, fatty acid oxidation and osteoblast differentiation. Applicants used qPCR to measure expression levels of key marker genes in adipocytes and osteoblasts in Cohort 1 (23 TH homozygotes and 18 CT heterozygotes). In adipocytes, Applicants observed higher gene expression in homozygotes than heterozygotes for marker genes for lipolysis (ATGL (1.3-fold), LIPE (2.1-fold) and PLIN2 (1.4-fold)) (Table 16). In osteoblasts, Applicants similarly saw higher gene expression in homozygotes than heterozygotes for marker genes for fatty acid oxidation (ACACB (1.1-fold), ACAT1 (1.5-fold), and CPT1A (1.7-fold)) and master regulators of osteoblast differentiation (RUNX2 (1.9-fold), OCN (1.4-fold), and OSX (1.2-fold)) (Table 16). These results indicate haplotype-specific control of genes involved in lipid oxidation and osteoblast formation.

TABLE 16

Fold change and significance (p-value) of expression changes in primary human osteoblasts and adipocytes (haplotype 1 and haplotype 2). p-values were calculated by Mann Whitney U test.

| | Gene | Fold change (±SE) | p-value |
|---|---|---|---|
| | | Homozygous/Heterozygous | |
| Osteoblasts | RUNX2 | 1.9 ± 0.42 | 0.06 |
| | OCN | 1.4 + 0.32 | 0.04 |
| | OSX | 1.2 + 0.27 | 0.001 |
| | ACCB | 1.1 + 0.13 | 0.04 |
| | ACAT1 | 1.5 + 0.31 | 0.05 |
| | CPT1 | 1.7 + 0.22 | 0.001 |
| Adipocytes | ATGL | 1.3 ± 0.35 | 0.02 |
| | LIPE | 2.1 + 0.56 | 0.01 |
| | PLIN2 | 1.4 + 0.25 | 0.05 |

These differences in gene expression were associated with cellular signatures relevant to hyperglycaemia and bone density. In adipocytes, adrenergic lipolysis rate and fatty acid release as measured by catecholamine-stimulated glycerol release were 1.9-fold higher in haplotype 1 homozygotes than heterozygotes (p-value=0.0012, FIG. 8A). Increased release of fatty acids from fat tissue is a hallmark of hyperglycemia (Girousse et al. 2013; Guilherme et al. 2008; Shulman 2014). In osteoblasts, Applicants found increased osteoblast differentiation in haplotype 1 homozygotes compared to heterozygotes (3-fold change, p-value=0.0014, FIG. 9A, Cohort 1) using ALP activity, a surrogate of increased bone formation (Farley and Baylink 1986). Furthermore, Applicants observed increased fatty acid oxidation in osteoblasts from 4 haplotype 1 homozygotes compared to 4 heterozygotes using radiolabeled palmitic acid oxidation assays (3-fold change, p=0.003, FIG. 9B, Cohort 4). This effect on fatty acid oxidation was increased specifically during early stages of osteoblast differentiation (Day 3 of osteoblast differentiation, FIG. 8B).

To better understand the role of lipid oxidation in osteoblasts, Applicants performed osteoblast differentiation assays in AMSCs from Cohort 1, treating the cells with etomoxir, which inhibits the rate-limiting enzyme in fatty acid oxidation carnitine palmitoyltransferase 1 (CPT-1) during early differentiation. The inhibitor revealed a dramatic reduction in osteoblast differentiation for the haplotype 1 homozygotes (p-value=0.005, FIG. 9A), while no effect was observed in heterozygotes.

Figures 8C, 8D, 8E:
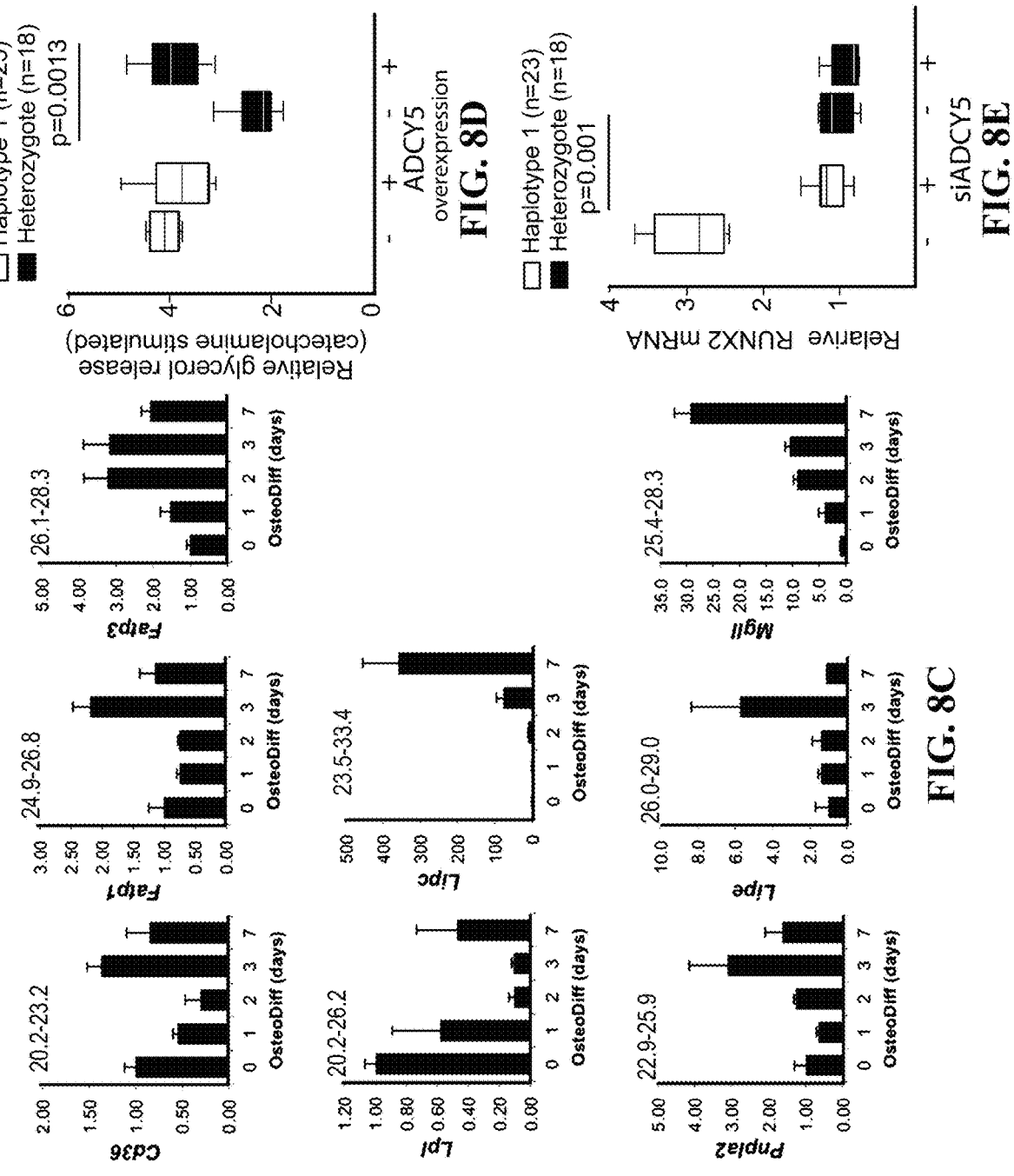
Figures 9A, 9B, 9C, 9D, 9E:
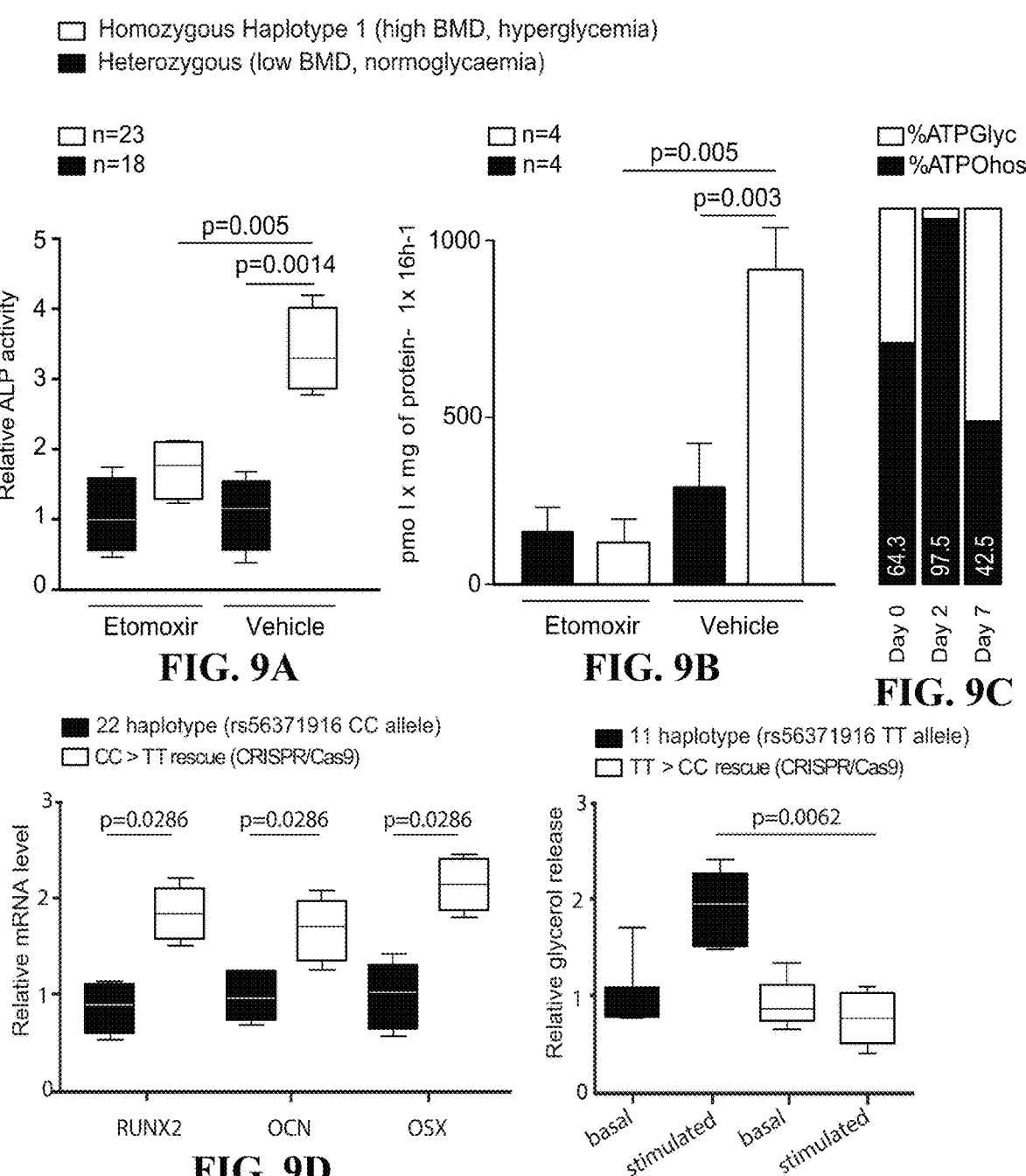

These data suggest that increased osteoblast differentiation depends on fatty acid oxidation at some stage in differentiation. While fatty acid utilization has previously been identified as an important process to support osteoblastogenesis, Applicants sought to further test whether the metabolic phenotype changed throughout the differentiation profile. Applicants found that ATP was primarily being generated via oxidative phosphorylation at day 0 (64.3%) and day 2 (97.5%) of differentiation, which are time points consistent with early osteo-progenitor cells. Interestingly, later in the osteoblast differentiation, the more mature osteoblasts (day 7) demonstrated a more glycolytic phenotype. Applicants then employed a more sophisticated assay to determine whether the osteoblasts exhibited substrate preference for mitochondrial oxidation at different stages of osteoblast differentiation. Indeed these data further confirm a strong shift from higher capacity to oxidize fatty acids in early differentiation (79% at day 0) which decreases towards late differentiation (45% by day 7) (FIG. 9C). The switch was accompanied by increased expression by day 2 of genes encoding fatty-acid transporters, including CD36, SLC27A1 (aka FATP1), and SLC27A3 (aka FATP3), and cytoplasmic lipases, including ATGL (aka PNPLA2), LIPE (aka HSL), and MGLL (FIG. 8C). Taken together these data indicate that during the early stages of osteoblast differentiation, osteo-progenitor cells depend on the use of fatty acids as an energy source, however, their metabolic profile switches towards glycolysis in the more mature osteoblast.

Example 7—Changing ADCY5 Expression Affects Lipid Oxidation in Primary Adipocytes and Osteoblasts To show directly that ADCY5 levels regulate lipolysis in adipocytes and lipid oxidation-dependent differentiation processes in osteoblasts, Applicants altered ADCY5 expression. In adipocytes, Applicants found that using lentiviral expression to increase ADCY5 levels (by 60%) led to elevated rates of catecholamine-stimulated lipolysis and fatty acid release, as measured by glycerol release in 4 heterozygotes compared to levels in 4 homozygotes for haplotype 1 (1.9-fold, SD=0.8, FIG. 8D, Cohort 4). In osteoblasts, Applicants found that using pooled siRNAs to decrease ADCY5 expression (by 56%) led to a major decrease in osteoblast differentiation as assessed by marker genes. Larger effects were seen in the same 4 haplotype 1-homozygotes than 4 heterozygotes (RUNX2 2.9- vs. 1.3-fold, OCN 3.2- vs. 1.3-fold, and OSX 3.7- vs 1.5-fold, s.e.m.=0.1), consistent with the notion that higher levels of elevated ADCY5 expression increase osteoblast differentiation in haplotype 1 carriers (FIG. 8E).

Example 8—Genome Editing of Rs56371916 Confirms that it Affects ADCY5 Expression, Lipid Oxidation and Osteoblast Differentiation To confirm directly that the haplotype-specific effects on ADCY5 gene expression and cellular properties described above are mediated by rs56371916, Applicants performed CRISPR-based genome editing to make isogenic changes at this SNP. Applicants edited AMSCs from a homozygote for haplotype 2 (genotype CC at rs56371916) to create isogenic AMSCs with genotype TT. Following osteoblast induction, TT homozygous cells showed higher ADCY5 expression levels ((1.6-fold)) (Table 17) and higher expression of osteoblast differentiation marker genes (RUNX2, osteocalcin (OCN) and osterix (OSX); 1.5-, 1.8- and 2.1-fold, respectively, FIG. 9D).

TABLE 17

Single-nucleotide editing reverses osteoblast differentiation and adipocyte lipid metabolism marker genes, confirming pleiotropy.

Relative mRNA levels in osteoblasts (ratio TT/CC)

| Gene | Fold change | p-value | Fold change (±SE) | p-value |
|---|---|---|---|---|
| ADCY5 | 1.6 + 0.4 | 0.0286 | 1.1 + 0.2 | n.s. |

TABLE 17-continued

Single-nucleotide editing reverses osteoblast differentiation and adipocyte lipid metabolism marker genes, confirming pleiotropy.

Relative AP activity levels in osteoblasts (ratio TT/CC)

| Diff day 14 Fold change | p-value |
|---|---|
| 1.6 + 0.2 | 0.01 |

Relative mRNA levels in adipocytes (ratio CC/TT)

| Gene | Fold change | p-value | Fold change | p-value |
|---|---|---|---|---|
| ADCY5 | 0.7 + 0.3 | 0.0286 | 1.03 + 0.3 | n.s. |

Relative mRNA levels in adipocytes (ratio TT/CC)

| Gene | Diff day 0 Fold change | p-value | Diff day 14 Fold change | p-value |
|---|---|---|---|---|
| ATGL | 1.3 + 0.4 | 0.02 | 1.5 + 0.9 | 0.07 |
| HSL | 1.8 + 0.63 | 0.09 | 1.8 + 0.4 | 0.03 |
| PLIN2 | 1.9 + 0.42 | 0.05 | 1.9 + 1.2 | 0.05 |

Applicants also edited AMSCs from a homozygote for haplotype 1 (genotype TT at rs56371916) to create isogenic AMSCs with genotype CC. Following adipocyte induction, CC homozygous cells showed reduced expression of ADCY5 (1.4-fold) and lipolysis marker genes (1.5- to 1.9-fold), as measured by qPCR (Table 17), as well as a reduced rate of catecholamine-stimulated lipolysis (2.1-fold, FIG. 9E). Applicants' genome-editing results in primary adipocytes and osteoblasts prove that rs56371916 has a direct effect on ADCY5 gene expression and cellular phenotypes relevant to FNBMD and glucose homeostasis. It cannot be ruled out, however, that rs56371916 may also affect other additional cell types or that additional variants at the 3q.21.1 locus may also have effects on bone- and glycemic traits. For example, variants in ADCY5 associated with two-hour glucose challenge (Saxena et al. 2010) and fasting glucose and Type 2 Diabetes (Dupuis et al. 2010; Fuchsberger et al. 2016) have recently been reported to affect ADCY5 expression in islets (Thurner et al. 2017; Roman et al. 2017; Hodson et al. 2014).

DISCUSSION

While GWAS have largely focused on individual phenotypes, there is growing evidence that many loci have pleiotropic effects, being associated with multiple traits (Bulik-Sullivan et al. 2015; Pickrell et al. 2016). Studying pleiotropic effects of loci across cell types and tissues is thus important and may also be useful for discovering the causal variants and their mechanism of action. In this study, Applicants focused on shared genetics between BMD and glycemic traits to help explain the molecular underpinnings of a clinically recognized link between type 2 diabetes and bone health (Leslie et al. 2012). Briefly, using GWAS summary statistics for BMD and glycemic traits, Applicants found a pleiotropic locus at 3q21.1, associated with FNBMD and fasting glucose levels. Applicants showed that the variant rs56371916, a strongly associated SNP in an intronic region of ADCY5, plays a causal role in processes related to these phenotypes by affecting the binding affinity of Sterol Regulatory Element Binding Protein 1 (SREBP1), shifting the balance between poised and repressed chromatin in mesenchymal cells. Applicants further showed that the genotype rs56371916 affects ADCY5 expression in both adipocytes and osteoblasts, which results in altered lipid metabolism. Applicants validated results by directly manipulating the upstream regulator SREBP1 and the target gene ADCY5 by siRNA-mediated knockdown and overexpression experiments, and by performing CRISPR-mediated genome editing on rs56371916 in primary human adipocytes and osteoblasts.

ADCY5 is a member of the membrane-bound adenylyl cyclase family of enzymes that mediates G protein-coupled receptor signaling through the synthesis of the metabolic messenger cAMP (Defer et al. 2000). Among other roles, cAMP plays a key role in lipolysis in adipocytes during fasting and stress, controlling the release of free fatty acids into the bloodstream. ADCY5 is among several adenylyl cyclases expressed at high levels in mesenchymal cells (Mabbott et al. 2013). Applicants' work implicates that ADCY5 is a member of the membrane-bound adenylyl cyclase family of enzymes that mediates G protein-coupled receptor signaling through the synthesis of the metabolic messenger cAMP (Defer et al. 2000). Among other roles, cAMP plays a key role in lipolysis in adipocytes during fasting and stress, controlling the release of free fatty acids into the bloodstream. ADCY5 is among several adenylyl cyclases expressed at high levels in mesenchymal cells (Mabbott et al. 2013). Applicants' work implicates adenylyl cyclase 5 in bone and glycemia-related phenotypes. Applicants examined the list of other bivariate loci for these phenotypes in the GEFOS and MAGIC consortium data, as well as loci with pleiotropic effects on bone and adipose-related traits in the UK Biobank database (http://big.stats.ox.ac.uk). Intriguingly, Applicants noted that the low-frequency missense variant, rs3730071, in another adenyl cyclase, ADCY6, showed genome-wide significant effects on both BMD ($p=2.2\times10^{-19}$) and fat mass ($p=1.6\times10^{-09}$) (http://big.stats.ox.ac.uk/variant/12-49168798-C-A). This observation provides additional support for the role of adenylyl cyclases on pleiotropy of bone and adipose.

This study sheds light on a critical role of ADCY5 in fatty acid oxidation in adipocytes and osteoblasts. While the physiological impact of lipid oxidation in adipocytes has been investigated in earlier studies, little research has focused on the role of fatty acid oxidation in osteoblasts, and how this might impact osteoblast differentiation. Acquisition of peak BMD is dependent on extensive osteoblast progenitor differentiation and is metabolically demanding. This work shows for the first time that osteoprogenitor cells preferentially metabolize fatty acids, and that inhibition of fatty acid oxidation during early stages of differentiation is sufficient to stall osteoblast differentiation programs. This context-specific feature of osteoblast bioenergetics supports the notion that adenylyl cyclase activity, which is essential for lipolysis, is central in osteoblast differentiation and ultimately BMD regulation. Consistent with these findings, partial loss-of-function of the GNAS complex (G protein alpha subunit), which directly stimulates adenylyl cyclases, results in low bone mass and a lack of adipose tissue (Balasubramanian et al. 2015).

The results from genetic association in human populations and experimental studies of adipocytes and osteoblasts in vitro provide strong evidence that expression levels of ADCY5 affect T2D and BMD, including offering a possible explanation for increased BMD in individuals with T2D. Extending these findings beyond osteoblast differentiation may also shed light on why the higher density bone in T2D is associated with greater fragility, and may have implications for developing treatment regimens for either trait without adverse effects on the other. Future studies, however, will be needed to carefully study organismal physiology in both humans and genetically engineered animal models.

Methods

Cohorts.

Cohort 1: primary AMSC, n=41 (TT: 23, CT: 18) (Technical University Munich and University Hohenheim, Germany)

Cohort 2: subcutaneous adipose tissue, n=30 and AMSC n=24 (not genotyped, University Bergen, Norway)

Cohort 3: subcutaneous adipose tissue, n=12 (TT: 8, CT: 1, CC: 2, NA: 1) (University Bergen, Norway)

Cohort 4 (subcohort of Cohort 1): primary AMSC, n=8 (TT: 4, CT: 4) (Technical University Munich and University Hohenheim, Germany)

Cohort 5: adipose tissue, n=237 obese and n=85 non-obese (not genotyped), pairwise subcutaneous and visceral samples (University Bergen, Norway)

Participant Samples.

Subjects and primary tissues and cell culture. Human adipose tissue was obtained with informed, written consent from each subject, and approval by the local ethics committee of the Faculty of Medicine of the Technical University of Munich, Germany, or the Regional Committee for Medical Research Ethics (REK) of Haukeland University Hospital, Bergen, Norway. Primary human adipose-derived progenitor cell cultures were obtained from subcutaneous adipose tissue of healthy European subjects 20 to 50 years of age and with a normal body-mass index (BMI) (20 to 24 kg/m2). Progenitor cells were isolated from whole subcutaneous adipose tissue from in total 23 homozygous haplotype 1 carriers and 18 heterozygous haplotype 2 carriers. Cells were isolated as previously described (Claussnitzer et al. 2014) with some modifications (see below). Genotyping was done by MassARRAY (Sequenom), Omni express (Illumina) or Sanger Sequencing. In addition, for direct RNA isolation and gene expression analysis, Applicants obtained whole adipose tissue and adipose-derived progenitor cells from non-genotyped healthy non-obese subjects undergoing elective surgeries (BMI 18 to 28 kg/m2) or severely obese European subjects undergoing bariatric surgery (BMI 35 to 52 kg/m2) (25 to 67 years of age), as described previously (Veum et al. 2011). The subjects were genotyped for both the identified GWAS index SNP (rs2124500) (rs2124500) and the identified causal variant rs56371916.

Genotyping. Genomic DNA was isolated from blood using the DNeasy Blood&Tissue Kit from Qiagen according to the manufacturer's protocol. A 250 bp fragment surrounding rs56371916 and rs2124500 was generated by PCR using the primers indicated below. The PCR product was sequenced using the Sanger sequencing services from GENEWIZ using the indicated primers.

TABLE 18

| PCR amplification primers. | |
| --- | --- |
| rs56371916_for | CTGAGTGGAAATCACCGCCA (SEQ ID NO: 3) |
| rs56371916_rev | GTGAAAAGTAATCTTCCTGCCTGG (SEQ ID NO: 4) |
| rs2124500_for | GTAGTGGCACTGGAACTTGA (SEQ ID NO: 5) |
| rs2124500_rev | GTGGGTCAGTCCCAAATCTT (SEQ ID NO: 6) |

TABLE 19

Sequencing primers.

| rs56371916_seq_for | AGTGGAAATCACCGCCAG (SEQ ID NO: 7) |
| rs2124500_seq_for | AGTGGCACTGGAACTTGAAC (SEQ ID NO: 8) |

Culture and differentiation of primary human AMSCs. Human liposuction material used for isolation of AMSCs was obtained from a collaborating private plastic surgery clinic Medaesthetic Privatklinik Hoffmann & Hoffmann in Munich, Germany. Harvested subcutaneous liposuction material was filled into sterile 1 L laboratory bottles and immediately transported to the laboratory in a secure transportation box. The fat was aliquoted into sterile straight-sided wide-mouth jars, excluding the transfer of liposuction fluid. The fat was stored in cold Adipocyte Basal medium (AC-BM) at a 1:1 ratio of fat to medium at 4° C. to be processed the following day. Additionally, small quantities of the original liposuction material would be aliquoted into T-25 flasks at a 1:1 ratio of fat to medium as controls to check for contamination. These control flasks were stored in the 37° C. incubator and were not processed. Krebs-Ringer Phosphate (KRP) buffer was prepared containing 200 U/ml of collagenase and 4% heat shock fraction BSA and sterilized by filtration using a BottleTop Filter 0.22 μM. When the fat reached room temperature (room temperature (RT)), 12.5 ml of liposuction material was aliquoted into sterile 50-ml tubes with plug seal caps. The tubes were filled to 47.5 ml with warm KRP-BSA-collagenase buffer and the caps were securely tightened and wrapped in Parafilm to avoid leakage. The tubes were incubated in a shaking water bath for 30 minutes at 37° C. with strong shaking. After 30 minutes, the oil on top was discarded and the supernatant was initially filtered through a 2000-μm nylon mesh. The supernatant of all tubes was combined after filtration and centrifuged at 200×g for 10 minutes. The supernatant was discarded and each pellet was resuspended with 3 ml of erythrocyte lysis buffer, then all the pellets were pooled and incubated for 10 minutes at RT. The cell suspension was filtered through a 250 μm Filter and then through 150 μm Filter, followed by centrifugation at 200 g for 10 minutes. The supernatant was discarded and the pellet containing pre-adipocytes was resuspended in an appropriate amount of DMEM/F12 with 1% penicillin/streptomycin (P/S) penicillin/streptomycin (P/S) and 10% FCS and seeded in T75 cell culture flasks and stored in the incubator (37° C., 5% CO2). The next day the medium was changed to expansion medium (DMEM/F12 medium supplemented with 2.5% FCS, 1% penicillin/streptomycin, 33 μM biotin, 17 μM pantothenic acid, 132 nM insulin, 10 ng/ml EGF, and 1 ng/ml FGF) until confluence. Adipogenic differentiation was then induced by supplementing with 66 nM insulin, 100 nM cortisol, 10 μg/ml transferrin, 1 nM triiodo-L-thyronin (T3), 2 μM rosiglitazone, 25 nM dexamethasone and 0.5 mM IBMX. Osteogenic differentiation was induced by aMEM with 10% FCS, 1% P/S, 10 mM b-glycerophosphate and 400 nM hydrocortisone.

Bivariate GWAS Analyses:

CPASSOC. CP-ASSOC combines GWAS summary statistics in one of two modes, that of homogeneous effects between GWAS (SHom) and that of heterogeneous effects between GWAS (SHet). These statistics are described in more detail elsewhere (Zhu et al. 2015): in brief, under the null expectation of no traits having an effect, SHom is the highest power omnibus test for any trait having an effect under an assumption of homogeneity, while SHet is a powerful statistic that does not assume homogeneity through the use of a truncated test statistic (in which only the traits with an effect above some threshold are considered, and this threshold is optimized). The SHet statistics are fit genome wide to a gamma distribution and evaluated to estimate the p-value.

Applicants used summary statistics from a large FNBMD GWAS study performed by the GEFOS Consortium (Estrada et al. 2012); n(FNBMD)=32,961 and n(LSBMD)=31,800, and from large GWAS studies from the MAGIC GWAS Consortium, glycaemic trait sample (Manning et al. 2012; Dupuis et al. 2010) n(FASTING GLUCOSE)=46,186, n(FASTING INSULIN)=38,238, n(HOMAIR)=37,037, n(HOMAB)=36,466. P-values and minor allele frequencies from the discovery samples were included in the analyses. β coefficients and SEs from the univariate association analyses were used to perform bivariate genome-wide association analyses. Applicants reported potential pleiotropic SNPs based on a suggestive significance level of (1) p-value≤5*10≤5*10-6 from the bivariate GWAS analyses; (2) the bivariate p-value divided by the univariate p-value is less than 0.05; and (3) univariate p-values≤0.05 for both phenotypes.

MTAG. MTAG (Multi-Trait Analysis of GWAS) is a method to combine summary statistics from related traits in a flexible framework which takes into account the genetic correlation of the traits (Turley et al. 2018). This is particularly helpful in the case of sample overlap in individuals without population structure, as the intercept term of the genetic correlation is associated with phenotypic association while the slope is an unbiased estimator of the shared genetic effects. Under this model, there is an estimated trait covariance matrix which produces the expected effects, and various constraints on that covariance can optimize for specific assumptions of the model. Summary statistics for all traits were filtered to HapMap3 SNPs and MTAG was applied with the following command line options:

python mtag.py- -ld_ref_panel ld_ref_panel/eur_w_ld_chr/- -sumstats <bone>,<glycaemic>- -perfect_gen-cov- -make_full_path- -snp_name SNP- -z_name Z- -stream_stdout- -verbose- -a1_name A1- -a2_name A2- -eaf_name MAF- -z_name Z- -n_name N- -chr_name CHR- -bpos_name BP Results with the additional option "- -equal_h2" were qualitatively similar (data not shown), but given that the lack of this parameter makes fewer assumptions about the covariance structure (Turley et al. 2017), Applicants opted for that model for downstream analysis. β coefficients and SEs from the univariate association analyses were used to perform bivariate genome-wide association analyses. Applicants reported potential pleiotropic SNPs based on the same criteria as CP-ASSOC above.

eLX. Bivariate GWAS analysis was performed using by the empirical-weighted linear-combined test statistics method (eLC) implemented in the eLX package using summary statistics from univariate GWAS meta-analyses (Chen and Hsu 2017). The eLC directly combines correlated test statistics (or p-values) obtained from variant-phenotype association or GWAS analyses with a weighted sum of univariate test statistics. eLC maximizes the overall association signals by accounting for the correlation between phenotypes. The weighting is estimated empirically using the Monte Carlo simulation. Unfiltered summary statistics for all traits were merged by SNP name. The eLX tool was applied with the -s 1-e<number of SNPs>–n 1 options and the dLC parametric estimate was used as the test statistic for calculating the effect, with an assumed distribution of Chi-square with two degrees of freedom (Chen et al. 2017). β coefficients and SEs from the univariate association analyses were used to perform bivariate genome-wide association analyses. Applicants reported potential pleiotropic SNPs based on the same criteria as CP-ASSOC above.

Culture and differentiation of immortalized human pre-adipocytes. Human primary supra-vascular-fraction (SVF) cells were received from Prof Yu-Hua Tseng (Harvard Medical School, Joslin Diabetes Center). The cells were previously isolated and immortalized from human subcutaneous white adipose tissue (hWAT) of a female subject, aged 56 with a BMI of 30.8. Culture and differentiation were performed following the protocol from the originating lab as described in (Xue et al. 2015). Briefly, pre-adipocytes were cultured in DMEM GlutaMax (Gibco, 10569010) supplemented with 10% Fetal Bovine Serum (Gibco 10082-147) and 1% P/SP/S (5,000 U/mL) (Gibco, 15070063) at 37° C. and 5% CO2. For differentiation, cells were treated with 0.25% trypsin (Gibco), counted using an automatic cell counter and 100K cells per well were seeded in a 12-well plate. Once cells reached confluency, differentiation was induced by adding freshly prepared adipogenic induction medium to cells (DMDM/High Glucose supplemented with 10% FBS, 1% Pen/Strep, 33 μM Biotin, 0.5 μM Human Insulin, 17 μM Pantothenate, 0.1 μM Dexamethasone, 2 nM 3,3',5-Triiodo-L-thyronine (T3), 500 μM Isobutyl methyl-xanthine (IBMX), and 30 μM Indomethacin). Induction media were replaced every three days for 24 days, until fully differentiated.

RNA preparation and qPCR. Total RNA was extracted with TRIzol (Invitrogen) or RNeasy Lipid Tissue Kit (Qiagen). cDNA was synthesized with High-Capacity cDNA Reverse Transcription Kit (Applied Biosystems). qPCR was performed using SYBR Green with 60° C. annealing temperature. Relative gene expression was calculated by the delta delta Ct method. Target gene expression was normalized to expression of HPRT (human) (de Kok et al. 2005) or TBP (human).

Oil Red-O (ORO)(ORO) staining. Lipid droplets (LDs) are lipid-storage organelles predominantly present in differentiated adipocytes. OROORO selectively stains neutral lipids, such as cholesteryl esters, triglycerides, and fatty acids, in cultured differentiated adipocytes, serving as a good measurement for the degree of differentiation. At day 10 of differentiation, the culture medium was removed and cells were carefully washed with PBS. The cellular monolayer was then covered with 3.7% Formaldehyde to fix the cells. After 1 hour, the formaldehyde was removed and cells were stained with ORO staining solution (0.3% Oil-Red-O in 60 ml Isopropanol and 40 ml H2O, filtered before use) and left to incubate for 1 hour. Afterwards, the ORO solution was removed and cells were washed twice and kept in PBS. Differentiated adipocytes full with lipid droplets will show a strong red color.

Transfection in cell cultures. Human Huh7 hepatoma, mouse C2C12 myoblasts, HT22 neuronal cells, Clonetics™ Normal Human Articular Chondrocytes (NHAC-kn), and human K562 lymphoblastoid cell lines were cultured in DMEM medium (supplemented with P/SP/S and 10% FBS). The human pre-adipocyte SGBS (Simpson-Golabi-Behmel Syndrome) cell line was cultured as previously described (Claussnitzer et al. 2014) in DMEM/Ham's F12 (1:1) medium (supplemented with 10% FCS, 17 μM biotin, 33 μM pantothenic acid and 1% P/S). To promote adipose differentiation of the SGBS cell line, cells were grown to confluence. For induction of adipocyte differentiation cells were cultured in serum free MCDB-131/DMEM/Ham's F12 (1:2) medium supplemented with 11 μM biotin, 22 μM pantothenic acid, 1% P/SP/S, 10 μg/ml human transferrin, 66 nM insulin, 100 nM cortisol, 1 nM triiodothyronine, 20 nM dexamethasone, 500 μM 3-isobutyl-1-methyl-xanthine (Serva, Germany) and 2 μM rosiglitazone (Alexis, Germany). All cells were maintained at 37° C. and 5% CO2. Huh7 cells (96-well plate, 1.1×104/well) were transfected one day after plating with approximately 90% confluence, K562 cells (12-well plate, 8×104/well) were transfected three days after plating with approximately 90% confluence, SGBS adipocytes (12-well plate, 8×104/well) were transfected at day eight after the induction of differentiation with approximately 80% confluence and C2C12 cells (12-well plate, 2×105/well) were transfected at day four after induction of differentiation with approximately 90% confluence. MC3T3 osteoblasts were seeded (seeding density: 250,000 cells/well) in) in a 6-well plate. Cells were differentiated using αMEMmedium supplemented with 10% FBS, 100 U/ml penicillin, 100 ug/ml streptomycin, 50 ug/ml ascorbic acid, and 10 mM beta-glycerophosphate. Huh7 were transfected with 0.5 μg of the respective firefly luciferase reporter vector and 1 μl Lipofectamine 2000 transfection reagent (Invitrogen, Darmstadt, Darmstadt, Germany), differentiated C2C12 myocytes were transfected with 1 μg of the respective pGL4.22-TK construct and 2 μl Lipofectamine reagent, and both K562-cells and differentiated SGBS adipocytes were transfected with 2 μg of the respective pGL4.22-TK construct and 2 μl Lipofectamine reagent. The firefly luciferase constructs were co-transfected with the ubiquitin promoter-driven Renilla luciferase reporter vector pRL-Ubi to normalize the transfection efficiency. Twenty-four hours after transfection, the cells were washed with PBS and lysed in 1× passive lysis buffer (Promega, Germany) on a rocking platform for 30 min at room temperature. Firefly and Renilla luciferase activity were measured (substrates D-luciferin and Coelenterazine from PJK, Germany) using a Luminoscan Ascent microplate luminometer (Thermo) and a Sirius tube luminometer (Berthold), respectively. The ratios of firefly luciferase expression to Renilla luciferase expression were calculated and normalized to the TK promoter control vector, i.e. enhancer activity. For overexpression ADCY5 cDNAs derived from SGBS total cDNA were inserted into the doxycycline-inducible Tet-On® Advanced Inducible Gene Expression System (BD Biosciences, Clontech, San Diego, CA). P-values comparing luciferase expression from risk and non-risk alleles were calculated using paired t-test.

Electrophoretic mobility shift assays (EMSA). EMSA was performed with Cy5-labelled oligonucleotide probes. rs56371916-flanking region oligonucleotides were commercially synthesized containing either the risk or the protective allele (Eurofins Genomics, EbersbergEurofins Genomics, Ebersberg, Germany). Cy5-labelled forward strands were annealed with non-labelled reverse strands, and the double-stranded probes were separated from single-stranded oligonucleotides on a 12% polyacrylamide gel. Complete separation was visualized by DNA shading. The efficiency of the labeling was tested by a dot plot, which confirmed that all of the primers were labeled similarly.

Primary human pre-adipocytes were induced to differentiate into adipocytes and osteoblasts for nuclear protein harvest. Adipogenic differentiation was induced by supplementing with 66 nM insulin, 100 nM cortisol, 10 μg/ml transferrin, 1 nM triiodo-L-thyronin (T3), 2 μM rosiglitazone, 25 nM dexamethasone and 0.5 mM IBMX. Osteogenic differentiation was induced by aMEM with 10% FCS, 1% P/S, 10 mM b-glycerophosphate and 400 nM hydrocortisone. Nuclear protein extracts from primary human pre-adipocytes were prepared with adapted protocols as described elsewhere (Claussnitzer et al. 2014). The supernatant was recovered and stored at −80° C. DNA-protein binding reactions were conducted in 50 mM Tris-HCl, 250 mM NaCl, 5 mM MgCl2, 2.5 mM EDTA, 2.5 mM DTT, 20% v/v glycerol and the appropriate concentrations of poly (dI-dC). For DNA-protein interactions, 2.5-7 μg of nuclear protein extract from the respective cell line was incubated for 10 min on ice, and Cy-5-labelled genotype-specific DNA probe was added for another 20 min. For competition experiments 50-, 100-, and 200 fold molar excess of unlabeled probe as competitor was included with the reaction prior to addition of Cy5-labeled DNA probes. Binding reactions were incubated for 20 min at 4° C. The DNA-protein complexes were resolved on a nondenaturation 5.3% polyacrylamide gel in 0.5× Tris/borate/EDTA buffer. Fluorescence was visualized with a Typhoon TRIO+ imager (GE Healthcare, Munich, Munich, Germany).

TABLE 20

EMSA probes.

| rs56371916_C_for | Cy5-TGGCCCCAGAGCAGAGTGG CCGGCGTGAGTGAAGATGATGA-3' (SEQ ID NO: 9) |
| rs56371916_C_rev | 5'-TCATCATCTTCACTCACGCCG GCCACTCTGCTCTGGGGCCA-3' (SEQ ID NO: 10) |
| rs56371916_T_for | Cy5-TGGCCCCAGAGCAGAGTGGC TGGCGTGAGTGAAGATGATGA-3' (SEQ ID NO: 11) |
| rs56371916_T_rev | 5'-TCATCATCTTCACTCACGCCA GCCACTCTGCTCTGGGGCCA-3' (SEQ ID NO: 12) |
| Srebp1-competitor-for | 5'-GTGGCCCCAGAGCAGGTGGGG TGATGAAGATGATGAACTGG-3' (SEQ ID NO: 13) |
| Srebp1-competitor-rev | 5'-CCAGTTCATCATCTTCATCAC CCCACCTGCTCTGGGGCCAC-3' (SEQ ID NO: 14) |

CRISPR/Cas9 genome editing. Plasmids: hCas9 and the gRNA cloning vector were purchased from Addgene (Plasmid ID #41815 and #41824, respectively). Genomic DNA was amplified from one rs56371916 CC allele carrier and one TT allele carrier. Site-directed mutagenesis was performed using the Q5® Site-Directed Mutagenesis Kit (New England Biolabs) using the mutagenesis primer 5'-XXXX-3'. The guide RNAs (gRNAs) were designed using the CRISPR design online tool from the Zhang lab (http://crispr.mit.edu/). 2 guide RNAs were used: 5' TAGAGGTCT-CACCCCACTCA-3' (SEQ ID NO: 15), 5'-GAGGGGACACCTATTCCTAG-3' (SEQ ID NO: 16). Cells were sorted using the MACSelect™ Transfected Cell Selection cell sorting kit (Miltenyi). Sorted cells were cultured for 3-5 days and clones propagated from single cell were picked out. Nucleotide exchange was confirmed by DNA sequencing.

Microarrays. Global gene expression in whole abdominal subcutaneous adipose tissue from 13 lean and 17 obese subjects was measured using Illumina HumanRef-8 v.3 BeadChip microarrays, as described previously (Dankel et al. 2010). Signal intensities were quantile normalized.

Lipolysis assay. Glycerol was measured in the medium after the 18-h incubation. Glycerol was measured spectrophotometrically using a glycerol 3-phosphate oxidase trinder kit (Sigma). For stimulated lipolysis measurements, 1 μmol/l isoproterenol (Sigma) was added for 1 hour.

Palmitate oxidation assay in osteoblasts. Palmitic acid oxidation rates were determined in differentiated osteoblasts using modifications of protocols previously described (Frey et al. 2015; Garcia-Martinez et al. 2005; Wende et al. 2005). Fatty acid oxidation were measured in flasks with stoppers equipped with center wells. Cultures were differentiated for 0, 3, 7 days prior to analysis. The cells were rinsed with PBS and incubated with MEM supplemented with 0.5% HS and 500 μM palmitic acid for 16 h. Cells were then incubated for an additional 3 h with fresh DMEM/0.5% HS that was supplemented with $[1-^{14}C]$palmitic acid (3.0 mCi/mmol). The oxidation reactions were terminated and $CO_2$ was released from the media by the addition of 3 M perchloric acid and 1 M NaOH to the center well containing Whatman filter paper. The acidified reaction mixture was incubated overnight at 4° C. and centrifuged at 4,000 rpm for 30 min before aliquots of the supernatant were counted for 14C-labeled acid soluble metabolites by scintillation counting of the filter paper. Each experiment was performed in triplicate and the results were normalized to total protein.

Alkaline Phosphatase staining. Proliferating Osteoblasts show alkaline phosphatase (ALP) activity, which is greatly enhanced during in vitro bone formation. ALP activity is therefore a sensitive marker for osteoblast differentiation. ALP can easily be detected using BCIP (5-bromo-4-chloro-3-indolyl-phosphate) in conjunction with NBT (nitro blue tetrazolium) as a substrate, which stains cells blue-violet when ALP is present. At day 10 of differentiation, culture medium was removed and cells were carefully washed with PBS. The cellular monolayer was covered with neutral buffered formalin 10% for 60 seconds, then washed with 0.05% Tween 20 in PBS without $Ca^{2+}$ or $Mg^{2+}$ (washing buffer). Cells were incubated with BCIP/NBT substrate solution (1 tablet dissolved in 10 ml distilled water) at room temperature in the dark for 5 to 10 minutes, checking the staining progress every 2 to 3 minutes. Afterwards, the substrate solution was removed, cells were washed with washing buffer and finally kept in PBS. ALP positive cells present a dark blue-violet color, whereas AP negative cells are colorless or faintly blue.

Alizarin Red S staining. Osteoblasts can be induced to produce vast extracellular calcium deposits in vitro, a process called mineralization. Calcium deposits are an indication of successful in vitro bone formation and can specifically be stained bright orange-red using Alizarin Red S. The Alizarin Red S staining solution was prepared by dissolving 2 g of Alizarin Red S in 100 ml distilled water and adjusting the pH to 4.1-4.3 with 0.1% $NH_4OH$. After filtration, the solution was stored in the dark. At day 10 of differentiation, culture medium was removed and cells were carefully washed with PBS without $Ca^{2+}$ or $Mg^{2+}$. The cellular monolayer was covered with neutral buffered formalin 10% for at least 30 minutes, then washed with distilled water and incubated with Alizarin Red S staining solution at room temperature in the dark for 45 minutes. Afterwards, the substrate solution was removed, cells were washed 4 times with 1 ml distilled water and finally kept in PBS. Undifferentiated cells, without extracellular calcium deposits, are slightly red, whereas mineralized osteoblasts, with extracellular calcium deposits, are bright orange-red.

Seahorse XF24 Flux analyzer. Primary bone marrow stromal cells (BMSCs) were isolated from C57BL/6J male and female mice at 8-10 weeks of age as previously reported. Briefly, BMSCs were plated $2.5 \times 10^4$ cells/well in the standard 96-well Agilent Seahorse plates. BMSCs were then treated with osteogenic differentiation medium (alpha MEM, 10 FBS, 1 Pen/Strep, supplemented with 25 ug/mL ascorbic acid and 5 mM β-glycerolphosphate) for 0, 2, or 7 days (Guntur et al. 2018). Agilent Bioanalyzer was used to determine changes in oxygen consumption rates (OCR) and extracellular acidification rates (ECAR) and values are normalized to total protein (ug). ATP production rates were estimated using OCR and ECAR data (Mookerjee et al. 2015). Applicants corrected ECAR by separating out contribution from $CO_2$ acidification and calculated the glycolytic ATP production rate. ATP production rates from oxidative phosphorylation was then estimated from OCR by subtracting out non mitochondrial respiration and multiplying by oligomycin sensitive fraction of respiration. Total ATP production rates were obtained after adding both glycolytic and oxidative phosphorylation ATP production rates. Data are represented as % Glycolytic and oxidative phosphorylation ATP production rates. To determine the cells capacity to use free fatty acids, cells were preferentially 'forced' to use fatty acids (0.6 mM oleic acid) by inhibiting glucose/pyruvate (2 uM UK5099) or glutamine (3 uM BPTES) utilization, followed by fatty acid oxidation etomoxir (4 uM etomoxir). Changes in OCR relative to substrate inhibition were then calculated.

Statistics. Statistical analyses were performed using two-tailed Student's t-test or ANOVA for comparing the means of two or multiple groups, respectively. Nonparametric testing (U-Mann-Whitney test) was used where appropriate, that is, when normal distribution of sample sets was not evident.

ATAC-seg in human pre-adipocytes and differentiating adipocytes. ATAC-seq was performed by adapting the protocol from Buenrostro et al. 2015 by adding a nuclei preparation step. Differentiating cells were lysed directly in cell culture plate at four time-points during differentiation (before adipogenesis was induced (DO hWAT and PAC), during early (D3 hWAT; D2 PAC) and advanced differentiation (D6 hWAT and PAC), as well as at terminal differentiation (D24 hWAT; D14 PAC)). Ice-cold lysis buffer was added directly onto cells grown in a 12-well plate. Plates were incubated on ice for 10 min until cells were permeabilized and nuclei released. Cells in lysis buffer were gently scraped off the well and transferred into a chilled 1.5 ml tube to create crude nuclei. Nuclei were spun down at 600×g for 10 min at 4° C. Nuclei pellets were then re-suspended in 40 μl Tagmentation DNA (TD) Buffer (Nextera, FC-121-1031) and quality of nuclei assessed using trypan blue. Volume of 50K nuclei was determined using a haemocytometer. Transposition reaction was performed as previously described (Buenrostro et al. 2015). All tagmented DNA was PCR amplified for 8 cycles using the following PCR conditions: 72° C. for 5 minutes, 98° C. for 30 seconds, followed by thermocycling at 98° C. for 10 seconds, 63° C. for 30 seconds and 72° C. for 1 minute. Quality of ATAC-seq libraries was assessed using a Bioanalyzer High Sensitivity ChIP (Applied Biosystems). The profiles showed that all libraries had a mean fragment size of ~200 bp and characteristic nucleosome patterning, indicating good quality. Libraries were pooled and sequenced on a HiSeq4000 Illumina, generating 50 mio reads/sample, 75 bp paired end. To reduce bias due to PCR amplification of libraries, duplicate reads were removed. Sequencing reads were aligned to hs37d5 and BWA-MEM was used for mapping. All experiments were performed in technical duplicates.

TABLE 21

| hWAT | | | barcode |
| --- | --- | --- | --- |
| day | rep | # | full sequence |
| D0 | 1 | 5 | CAAGCAGAAGACGGCATACGAGATAGGAGTCC GTCTCGTGGGCTCGGAGATGT (SEQ ID NO: 17) |
| | 2 | 6 | CAAGCAGAAGACGGCATACGAGATCATGCCTA GTCTCGTGGGCTCGGAGATGT (SEQ ID NO: 18) |
| D3 | 1 | 7 | CAAGCAGAAGACGGCATACGAGATGTAGAGAG GTCTCGTGGGCTCGGAGATGT (SEQ ID NO: 19) |
| | 2 | 8 | CAAGCAGAAGACGGCATACGAGATCCTCTCTG GTCTCGTGGGCTCGGAGATGT (SEQ ID NO: 20) |
| D6 | 1 | 9 | CAAGCAGAAGACGGCATACGAGATAGCGTAGC GTCTCGTGGGCTCGGAGATGT (SEQ ID NO: 21) |
| | 2 | 10 | CAAGCAGAAGACGGCATACGAGATCAGCCTCG TCTCGTGGGCTCGGAGATGT (SEQ ID NO: 22) |
| D24 | 1 | 13 | CAAGCAGAAGACGGCATACGAGATATCACGAC CGTCTCGTGGGCTCGGAGATGT (SEQ ID NO: 23) |
| | 2 | 14 | CAAGCAGAAGACGGCATACGAGATGCAGTGGT GTCTCGTGGGCTCGGAGATGT (SEQ ID NO: 24) |

TABLE 22

| PAC | | | barcode |
| --- | --- | --- | --- |
| day | rep | # | full sequence |
| D0 | 1 | 5 | CAAGCAGAAGACGGCATACGAGATAGGAGTCC GTCTCGTGGGCTCGGAGATGT (SEQ ID NO: 25) |
| | 2 | 6 | CAAGCAGAAGACGGCATACGAGATCATGCCTA GTCTCGTGGGCTCGGAGATGT (SEQ ID NO: 26) |
| D2 | 1 | 8 | CAAGCAGAAGACGGCATACGAGATCCTCTCTG GTCTCGTGGGCTCGGAGATGT (SEQ ID NO: 27) |
| | 2 | 9 | CAAGCAGAAGACGGCATACGAGATAGCGTAGC GTCTCGTGGGCTCGGAGATGT (SEQ ID NO: 28) |
| D6 | 1 | 10 | CAAGCAGAAGACGGCATACGAGATCAGCCTCG GTCTCGTGGGCTCGGAGATGT (SEQ ID NO: 29) |
| | 2 | 11 | CAAGCAGAAGACGGCATACGAGATTGCCTCTT GTCTCGTGGGCTCGGAGATGT (SEQ ID NO: 30) |
| D14 | 1 | 12 | CAAGCAGAAGACGGCATACGAGATTCCTCTAC GTCTCGTGGGCTCGGAGATGT (SEQ ID NO: 31) |
| | 2 | 13 | CAAGCAGAAGACGGCATACGAGATATCACGAC GTCTCGTGGGCTCGGAGATGT (SEQ ID NO: 32) |

Native ChIP-seg in primary pre-adipocytes. Native Chromatin Immunoprecipitation-Sequencing (ChIP-seq) in adipocytes was performed by adapting the protocol from Ribarska and Gilfillan 2018. In short, cells were lysed directly in cell culture plate at four time-points during differentiation (before adipogenesis was induced (D0), and during early (D2), mid (D6) and terminal differentiation (D14)). Ice-cold lysis buffer (containing 10 mM Tris-HCl (pH7.4), 10 mM NaCl, 3 mM MgCl2, 0.1% Igepal CA-630, supplemented with Protease Inhibitor Cocktail (Sigma P8340) and Sodium butyrate (Sigma B5887)) was added directly onto cells in culture plates. Following a 10 min incubation on ice, cells were scraped off plates using a cell scraper and spun down at 600×g for 10 min at 4° C. The resulting nuclei pellets were resuspended in MNase Digestion buffer (50 mM Tris-HCl, pH 8.0, 1 mM CaCl2), 0.2% Triton X-100, supplemented with Protease Inhibitor Cocktail and Sodium butyrate). Nuclei were then counted using trypan blue and incubated with 2×105 U/ml MNase-based Enzymatic Shearing Cocktail (Active Motif, 103295) for 10 min at 37° C. Subsequent steps were performed as previously described (Ribarska and Gilfillan 2018). Native chromatin was incubated overnight at 4° C. with antibodies against H3K27me3 (Diagenode, C15410069) and H3K27ac (Abcam, ab4729) using an end-to-end rotator. ChIP-seq library preparation and sequencing was performed by the Welcome Centre for Human Genetics at the University of Oxford. Libraries were pooled and sequenced on a HiSeq4000 Illumina generating approximately 50mio reads/sample, 75 bp paired end. To reduce bias due to PCR amplification of libraries, duplicate reads were removed. Sequencing reads were aligned to hg19 and Bowtie 2 was used for mapping. All experiments were performed in technical duplicates. Three input control samples corresponding to the different experimental timepoints (D0, D2, D6, D14) were processed and sequenced in parallel.

Chromatin state segmentation and visualization. Chromatin state segmentations were obtained from the Roadmap Epigenomics Project (Claussnitzer et al. 2014) and visualized in the WashU Epigenome Browser (Zhou et al. 2011). Specifically, imputed chromatin state calls from a 25-state model based on imputed datasets from 12 chromatin marks were used (Zhou et al. 2011; Ernst and Kellis 2012). Split panels were constructed using the epigenome browser's JSON-based configuration system. Shown are chromatin state calls across all epigenomes, as well as putative regulatory region delineations from the Roadmap Epigenomics Project.

Clustering of epigenomes based on H3K27me3 enrichment. Linkage cluster trees from Roadmap (http://egg2.wustl.edu/roadmap/web_portal/epg_clustering.html) for the H3K27me3 chromatin mark were filtered to non-immortal cell lines (all consolidated epigenomes other than cancer cell lines and GM12878 from the ENCODE project). Observed H3K27me3 fold enrichment over input ("H3K27me3 signal") was averaged over the entire risk locus for each of the epigenomes. Then, for each clade of the linkage cluster tree, a relative enrichment in H3K27me3 signal was calculated as the ratio between the average signal across epigenomes within the clade and the average signal across epigenomes outside the clade.

Repressor annotations. To identify putative stretch enhancers with cell lineage specific repression, Applicants focused on repressed states (state 24), defined by high levels of H3 lysine 27 trimethylation (H3K27me3), associated with Polycomb repression and lower levels of promoter-associated marks (H3K4me3, H3K4me2, H3K9ac) and enhancer-associated marks (H3K4me1 and H3k27ac). To recognize master regulatory loci, Applicants combined consecutive Polycomb-repressed elements into clusters by joining pairs of elements that were 200 bp apart or less (one quarter of the median length of repressors), and evaluated total cluster length.

Hi-C data processing and visualization. Hi-C data from human H1-hESC derived mesenchymal stem cell cultured cells (Dixon et al. 2015) were downloaded from SRA (SRR1030739-SRR1030744) and reprocessed using hiclib, including iterative mapping to hg19 and iterative correction (Imakaev et al. 2012), at 10 kb resolution. Processing was done with both separate and combined replicates; owing to replicate similarity, the combined replicates were used for final display. Experiments from the ENCODE (DNase & CTCF) and Roadmap (chromatin state) projects were visualized using the WashU Epigenome Gateway (Zhou et al. 2012; interactive session 2apalcl6nH).

Phylogenetic Module Complexity Analysis (PMCA. Applicants used the PMCA method described in (Claussnitzer et al. 2014) with several modifications. Briefly, 972 position weight matrices from the Catalog of Inferred Sequences of Binding Preferences (the Catalog of Inferred Sequences of Binding Preferences (CIS-BP)) were grouped in 192 motif matrix families using TomTom, as previously described (Maurano et al. 2015), and families were further overlapped by motif name to create a many-to-many mapping where individual TFs had multiple motifs annotated. MOODS (Korhonen et al. 2009) was used to scan a variant-flanking regions of the human reference genome (variant at mid-position) and its orthologous regions for cross-species conserved groups of transcription factor binding site motifs, so called groups of transcription factor binding site motifs, so called motif modules. A module is defined as a set of binding site motifs, whose order and distance range is conserved across species (Claussnitzer et al. 2014). The PMCA method counts instances of conserved motifs within conserved modules within the 120 bp sequence context of a given variant. Enrichments of motifs in conserved modules are computed 10,000 permutations of orthologous sets. The PMCA method counts instances of conserved motifs within conserved modules within the 120 bp sequence context of a given variant. Enrichments of motifs in conserved modules are computed 10,000 permutations of orthologous sets.

Basset convolutional neural network (CNN) trained on genome-wide chromatin accessibility (ATAC-seq) data throughout AMSC differentiation. ATAC-seq IDR reproducible peaks for day 0, day 3, day 6, and day 24 of differentiation of hWATs (see Methods), along with peaks of DNase hypersensitivity of Osteoblasts (ENCODE file ENCFF573CUG), were collated and normalized to 20 bp. A Basset model was trained with two convolutional layers (512 and 128 filters; 9 and 5 filter sizes; 0.1 dropout, 1 width pooling) and two fully connected hidden layers with 128 units and 0.5 dropout, using weight normalization, a learning rate of 0.01, and momentum of 0.97. The best validation accuracy model was used for downstream analysis.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of modulating fatty acid oxidation rate or osteoblast differentiation in a cell in vivo or in vitro, the method comprising:

contacting the cell with an agent that increases or decreases the expression or activity of ADCY5 in the cell, thereby modulating fatty acid oxidation rate or osteoblast differentiation in the cell.

2. The method of claim 1, wherein the cell is an adipocyte, and the method increases the expression or activity of ADCY5 in the cell.

3. The method of claim 1, wherein the cell is an osteoblast, and the method decreases the expression or activity of ADCY5 in the cell.

4. The method of claim 3, wherein decreasing the expression or activity of ADCY5 in a cell in vivo treats Type 2 Diabetes.

5. The method of claim 1, wherein decreasing the expression or activity of ADCY5 in adipocytes of the subject decreases fasting glucose level.

6. The method of claim 1, wherein increasing the expression or activity of ADCY5 in adipocytes in vivo increases fasting glucose levels.

7. The method of claim 1, wherein increasing the expression or activity of ADCY5 in osteoblasts of the subject promotes bone growth.

8. The method of claim 1, wherein decreasing the expression or activity of ADCY5 in osteoblasts in vivo reduces or inhibits bone growth.

9. The method of claim 8, wherein decreasing the expression or activity of ADCY5 in the osteoblasts of a subject is achieved using a therapeutic antibody, antibody fragment, antibody-like protein scaffold, aptamer, protein, CRISPR system or small molecule, or a combination thereof, as a modulating agent.

10. The method of claim 9, wherein the small molecule is etomoxir.

11. A method of increasing or decreasing the expression or activity of adenylyl cyclase 5 (ADCY5) in a cell of a patient in need thereof to treat a metabolic disorder in the patient, the method comprising:

identifying or having identified the patient as being homozygous at the 3q21.1 locus for a haplotype characteristic of high bone mineral density and increased hyperglycemia; and contacting the cell with an agent that increases or decreases the expression or activity of adenylyl cyclase 5 (ADCY5) in the cell.

12. The method of claim 1, wherein the expression or activity of ADCY5 is increased or decreased by introducing a mutation or base edit that modulates ADCY5 expression in the cell of the subject.

13. The method of claim 12, wherein the base edit is made to genomic DNA or expressed RNA in the cell of the subject using a CRISPR-Cas system.

14. The method of claim 1, wherein the cell is an adipocyte, an osteoblast, or both an adipocyte and an osteoblast.

15. The method of claim 2, wherein the metabolic disorder comprises high bone mineral density and hyperglycemia.

16. The method of claim 3, wherein the metabolic disorder comprises high bone mineral density and hyperglycemia.

17. The method of claim 1, wherein the one or more modulating agents comprises a therapeutic antibody, antibody fragment, antibody-like protein scaffold, aptamer, polypeptide, protein, genetic modifying agent, small molecule, small molecule degrader, or combination thereof.

18. The method of claim 12, wherein the mutation or base edit is introduced using a CRISPR-Cas system, RNAi system, a TALEN, a Zn-finger nuclease, or a meganuclease.

19. The method of claim 12, wherein the mutation or base edit changes a C to T at rs56371916 to increase ADCY5 expression.

20. The method of claim 12, wherein the mutation or base edit changes a T to C at rs56371916 to decrease ADCY5 expression.

21. A method of modulating expression or activity of adenylyl cyclase 5 (ADCY5) in a cell of a subject in need thereof, wherein said modulating is capable of treating a metabolic disorder, regulating fasting glucose levels, or regulating bone growth rates, or any combination thereof, the method comprising contacting a mesenchymal stem cell (MSC)-derived cell of the subject with one or more modulating agents that modulate the expression or activity of ADCY5 in the cell of the subject; and wherein said modulating comprises increasing the expression or activity of ADCY5 in the cell or decreasing the expression or activity of ADCY5 in the cell.

22. The method of claim 21, wherein the cell is an adipocyte, and wherein modulating the expression or activity of ADCY5 comprises increasing the expression or activity of ADCY5.

23. The method of claim 21, wherein the cell is an osteoblast, and wherein modulating the expression or activity of ADCY5 comprises decreasing the expression or activity of ADCY5.

24. The method of claim 21, wherein the metabolic disorder comprises high bone mineral density and hyperglycemia.

25. The method of claim 21, wherein the metabolic disorder is Type 2 Diabetes.

26. The method of claim 21, wherein the one or more modulating agents comprises a therapeutic antibody, antibody fragment, antibody-like protein scaffold, aptamer, polypeptide, protein, genetic modifying agent, small molecule, small molecule degrader, or combination thereof.

27. The method of claim 26, wherein the small molecule is etomoxir.

28. The method of claim 11, wherein the metabolic disorder comprises high bone mineral density and hyperglycemia.

29. The method of claim 11, wherein the metabolic disorder is Type 2 Diabetes.

30. The method of claim 11, wherein the agent comprises a therapeutic antibody, antibody fragment, antibody-like protein scaffold, aptamer, polypeptide, protein, genetic modifying agent, small molecule, small molecule degrader, or combination thereof.

31. The method of claim 30, wherein the small molecule is etomoxir.

* * * * *